United States Patent [19]

Yaver et al.

[11] Patent Number: 5,770,418
[45] Date of Patent: Jun. 23, 1998

US005770418A

[54] PURIFIED POLYPORUS LACCASES AND NUCLEIC ACIDS ENCODING SAME

[75] Inventors: Debbie Sue Yaver, Davis; Feng Xu, Woodland, both of Calif.; Henrik Dalbøge, Virum, Denmark; Palle Schneider, Bellerup, Denmark; Dorrit A. Aælyng, Vaerloese, Denmark

[73] Assignees: Novo Nordisk A/S, Begsvaard, Denmark; Novo Nordisk Biotech. Inc., Davis, Calif.

[21] Appl. No.: 441,147

[22] Filed: May 15, 1995

Related U.S. Application Data

[63] Continuation-in-part of Ser. No. 265,534, Jun. 24, 1994, abandoned.

[51] Int. Cl.$^6$ .............................. C12N 15/53; C12N 9/02; C12N 15/63; C12N 1/15
[52] U.S. Cl. ................... 435/189; 435/320.1; 435/252.3; 435/325; 435/172.3; 435/254.11; 435/254.3; 935/14; 935/27; 935/34; 935/56; 935/68; 536/23.2
[58] Field of Search ............................... 435/189, 320.1, 435/252.3, 240.2, 172.3, 254.11, 254.3, 325; 536/23.2; 935/14, 27, 34, 56, 68

[56] References Cited

U.S. PATENT DOCUMENTS 3,251,742 5/1966 Soloway ..................................... 167/88

FOREIGN PATENT DOCUMENTS

| | | |
|---|---|---|
| 0 504 005 A1 | 3/1992 | European Pat. Off. . |
| 3634761 C1 | 10/1986 | Germany . |
| 4033246 C1 | 10/1990 | Germany . |
| 92-01046 | 1/1992 | WIPO . |
| 93-12259 | 6/1993 | WIPO . |
| WO 95/01426 | 1/1995 | WIPO . |

OTHER PUBLICATIONS

Chet et al., Microbios Letters, vol. 29, pp. 37–43, 1985.
Bollag et al., Applied and Environemntal Microbiology, vol. 48., No. 4, pp. 849–854, 1984.
Yaver et al., Gen. Tech. Rep. NC, pp. 115–118, 1994.
Trojanowski et al., Lignin Enzymic and Nicrobial Degradation, pp. 223–227, 1987.
S.J. Gould et al., "Use of the Polymerase Chain Reaction For Homology Probing: Isolation of Partial cDNA of Genomic Clones Encoding the Iron–Sulfur Protein as Succinate Dehydrogenase From Several Species", Proc. Natl. Acad. Sci. 86: 1934–1938, Mar. 1989.
C.R. Perry et al., "Identification of Two Laccase Genes in the Cultivated Mushroom Agaricus bisporus", J. Gen. Microbiol. 139 (Pt 6) 1209–1218, Sep. 1993.
P.M. Coll et al., "Characterization and Stuctural Analysis of the Laccase I Gene From the Newly Isolated Ligninolytic Basidiomycete PM1 (CECT 2971)", Appl. Environ. Microbiol. 59(12) 4129–4135, Dec. 1993.
M. Devchand et al., Expression of Heterologous Proteins in Aspergillus, J. Biotechnol. 17: 3–10, 1991.

*Primary Examiner*—Rebecca E. Prouty
*Attorney, Agent, or Firm*—Steve T. Zelson; Elias J. Lambiris

[57] ABSTRACT

The present invention relates to isolated nucleic acid constructs containing a sequence encoding a Polyporus laccase, and the laccase proteins encoded thereby.

28 Claims, 44 Drawing Sheets

```
         10          20          30          40          50          60          70
AGATTTCTGA CACCGGTGCA ATCTTGACAC TGTACCAACC GGGCAAGTCT CGTCCTTGGT TCTCGGGGAC
         80          90         100         110         120         130         140
TGGCGCCGGT CGCTACCCCT TGGTCATTCA CTCTACCAGA GCGCTGGCTT CGCCGAGGTA TAAAGGATGT
        150         160         170         180         190         200         210
TGCGCGACAC CCTCAACACC CCAACTCAAG CCCCACTTGA GCTTTTGCGA GATCCTCCAC ATACCACTCA
        220         230         239    248        257    266
CTACTTTCAA GTTCTTCAAC ATG TCG AGG TTT CAC TCT CTT CTC GTC GTT
                         Met Ser Arg Phe His Ser Leu Leu Val Val
 275         284         293         302         311         320
GCT TCC CTT ACG GCT GTG GCC CAC GCC GGT ATC GGT CCC GTC GCC GAC CTA ACC
Ala Ser Leu Thr Ala Val Ala His Ala Gly Ile Gly Pro Val Ala Asp Leu Thr
 329         338         347         356         365         374
ATC ACC AAC GCA GCG GTC AGC CCC GAC GGG TTT TCT CGC CAG GCC GTC GTC GTG
Ile Thr Asn Ala Ala Val Ser Pro Asp Gly Phe Ser Arg Gln Ala Val Val Val
 383         392         401         410         423         433
AAC GGC ACC CCT GGC CTC ATC ACG GGT AAC ATG GTTCGTCTCG GCTCGCACTA
Asn Gly Thr Pro Gly Leu Ile Thr Gly Asn Met
```

Fig. 1A

```
                    443           453              463                473           482          491
              GGGGGTTGTA TCGTTCCTGA CGTTGTTGGA G GGG GAT CGC TTC CAG CTC AAT GTC ATC
                                                  Gly Asp Arg Phe Gln Leu Asn Val Ile 500              509           518              527                543                553
GAC AAC CTT ACC AAC CAC ACG ATG AAG AGC ACG AGT ATT GTGAGCTGCT ATTTCTCCGG
Asp Asn Leu Thr Asn His Thr Met Val Lys Ser Thr Ser Ile 563              573           583               592              601           610
ACGGGGCTTC ATTGTGCTAA TAATCGTCGT GTGCAG CAC TGG CAC GGT TTC TTC CAG AAG
                                        His Trp His Gly Phe Phe Gln Lys 619           628              637               646              655              664
GGT ACC AAC TGG GCC GAC GGT CCC GCC GAC TTC ATC AAC CAG TGC CCG ATC TCA TCT
Gly Thr Asn Trp Ala Asp Gly Pro Ala Phe Ile Asn Gln Cys Pro Ile Ser Ser 673              682              691           700              709              720
GGT CAC TCG TTC CTG TAC GAC TTC CAG GTT CAG CCT GAC CAG GCT G GTAAGTACGG
Gly His Ser Phe Leu Tyr Asp Phe Gln Val Gln Pro Asp Gln Ala Gly 730              740              750              760              770           779
TCGTTATGGA GTATACTGCG CATTGCTAAA CCACATGGTG AACAG GT ACC TTC TGG TAT
                                                      Thr Phe Trp Tyr 788              797              806              815              824           833
CAC AGT CAC TTG TCT ACG CAG TAC TGT GAT GGT TTG AGG GGT TTC CCG TTC GTT
His Ser His Leu Ser Thr Gln Tyr Cys Asp Gly Leu Arg Gly Pro Phe Val Val
```

Fig. 1B

```
           842           851           860           869           878           889
 TAC GAC CCG AAT GAC CCG GCC GCC GAC CTG TAC GAC GTC GAC AAC G   GTAAGGACGA
 Tyr Asp Pro Asn Asp Pro Ala Ala Asp Leu Tyr Asp Val Asp Asn Asp 899           909           919           929           940           949
 ATTCGAACCG TAAATACTTG CTTACTGATA CTTCTCGATG AATTAG AC GAC ACT GTC ATT
                                                        Asp Thr Val Ile 958           967           976           985           994          1009
 ACC CTT GTG GAT TGG TAC CAC GTC GCC GCG AAG CTG GGC CCC GCA TTC CC   GTAAGTCCAT
 Thr Leu Val Asp Trp Tyr His Val Ala Ala Lys Leu Gly Pro Ala Phe Pro 1019          1029          1039                     1049          1060          1069
 GAGTATTCTG CTGTTGAAATC TGTCTTAACT GTGCATATCA G T CTC GGC GAC GCC ACC
                                                  Leu Gly Ala Asp Ala Thr 1078          1087          1096          1105          1114          1123
 CTC ATC AAC GGT AAG GGA CGC TCC CCC AGC ACG ACC GCG GAC CTC TCA GTT
 Leu Ile Asn Gly Lys Gly Arg Ser Pro Ser Thr Thr Ala Asp Leu Ser Val 1132          1141                      1156          1166          1176          1186
 ATC AGC GTC ACC CCG GGT AAA CG GTATGCTATA TCTTATCTTA TCTGATGGCA TTTCTCTGAG
 Ile Ser Val Thr Pro Gly Lys Arg 1196           1207          1216          1225          1234
 ACATTCTCCA G C TAC CGT TTC CGC CTG TCC GTG TCG TGC GAC CCC AAC TAC
              Tyr Arg Phe Arg Leu Ser Val Ser Cys Asp Pro Asn Tyr
```

Fig. 1C

```
1243                  1252             1261                  1270                  1279                  1288
ACG TTC AGC ATC GAT GGT CAC AAC ATG ACG ATC ATC GAG ACC GAC TCA ATC AAC
Thr Phe Ser Ile Asp Gly His Asn Met Thr Ile Ile Glu Thr Asp Ser Ile Asn 1297                  1306             1315                  1324                  1333                  1342
ACG GCG CCC CTC GTC GAC TCC ATT CAG ATC TTC GCC GCC CAG CGT TAC TCC
Thr Ala Pro Leu Val Val Asp Ser Ile Gln Ile Phe Ala Ala Gln Arg Tyr Ser 1351                  1364             1374                  1384                  1394                  1404
TTC GTG GTAAGTTCGA TTCATCCTCT AACGTTGGTC GCTGTTAGTG ATCGTATGGT CATGTAG
Phe Val 1414                  1423             1432                  1441                  1450                  1459
CTC GAG GCC AAC CAG GCC GTC GAC AAC TAC TGG ATT CGC GCC AAC CCG AAC TTC
Leu Glu Ala Asn Gln Ala Val Asp Asn Tyr Trp Ile Arg Ala Asn Pro Asn Phe 1468                  1477             1486                  1495                  1504                  1513
GGT AAC GTC GGG TTC ACC GGC ATT GGC ATC AAC TCG GCT ATC CTC CGC TAC GAT GGT
Gly Asn Val Gly Phe Thr Gly Ile Gly Ile Asn Ser Ala Ile Leu Arg Tyr Asp Gly 1522                  1531             1540                  1549                  1558                  1567
GCC GCT GCC GTG GAG CCC ACC ACA ACG CAA ACC ACG TCG ACT GCG CCG CTC AAC
Ala Ala Ala Val Glu Pro Thr Thr Thr Gln Thr Thr Ser Thr Ala Pro Leu Asn 1576                  1585             1594                  1603             1619             1629
GAG GTC AAC CTG CAC CCG GTT ACC ACC GCT GTG GTATGTAATA TTGTCGGTAA
Glu Val Asn Leu His Pro Val Thr Thr Ala Val

Fig. 1D
```

```
1639        1649       1659       1669       1678       1687
TGTAATACAT TGTTGCTGAC CTCGACCCCC ACAG CCT GGC TCG CCC GTC GCT GGT GGT
                                      Pro Gly Ser Pro Val Ala Gly Gly 1696       1705       1714       1723       1732       1741
GTC GAC CTG GCC ATC AAC ATG GCG TTC AAC GGC ACC AAC TTC TTC ATC
Val Asp Leu Ala Ile Asn Met Ala Phe Asn Gly Thr Asn Phe Phe Ile 1750       1759       1768       1777       1786       1795
AAC GGC ACG TCT TTC ACG CCC CCG CCG ACC GTG CTC CTG CTG CAG ATC ATC AGC
Asn Gly Thr Ser Phe Thr Pro Pro Pro Thr Val Pro Val Leu Leu Gln Ile Ile Ser 1804       1813       1822       1831       1840       1849
GGC GCG CAG AAC GCG CAG GAC CTC CTG CCC TCC GGT AGC GTC TAC TCG CTT CCC
Gly Ala Gln Asn Ala Gln Asp Leu Leu Pro Ser Gly Ser Val Tyr Ser Leu Pro 1858       1867       1876       1885       1894       1903
TCG AAC GCC GAC ATC GAG ATC TCC TTC CCC GCC ACC GCC GCC GCC CCC GGT GCG
Ser Asn Ala Asp Ile Glu Ile Ser Phe Pro Ala Thr Ala Ala Ala Pro Gly Ala 1912       1921       1930       1939       1948       1957
CCC CAC CCC TTC CAC TTG CAC GGG CAC GCG TTC GCG GTC GTC CGC AGC GCC GGC
Pro His Pro Phe His Leu His Gly His Ala Phe Ala Val Val Arg Ser Ala Gly 1966       1975       1984       1993       2002       2011
AGC ACG GTT TAC AAC TAC GAC AAC CCC ATC TTC CGC GAC GTC AGC ACG GGG
Ser Thr Val Tyr Asn Tyr Asp Asn Pro Ile Phe Arg Asp Val Ser Thr Gly
```

Fig. 1E

```
        2020              2029              2038              2047              2056              2065
ACG CCT GCG GCC GGT GAC AAC GTC ACC ATC CGC TTC CGC ACC GAC AAC CCC GGC
Thr Pro Ala Ala Gly Asp Asn Val Thr Ile Arg Phe Arg Thr Asp Asn Pro Gly 2074              2083              2092              2101              2110              2119
CCG TGG TTC CTC CAC TGC CAC ATC GAC TTC CAC GAG GCC GGC TTC GCC GTC
Pro Trp Phe Leu His Cys His Ile Asp Phe His Leu Glu Ala Gly Phe Ala Val 2128              2137              2146              2155              2164              2173
GTG TTC GCG GAG GAC ATC CCC GAC GTC GCG TCG AAC CCC GTC CCC CAG GCG
Val Phe Ala Glu Asp Ile Pro Asp Val Ala Ser Ala Asn Pro Val Pro Gln Ala 2182              2191              2200              2209              2218              2231
TGG TCC GAC CTC TGT CCG ACC TAC GAC GCG CTC GAC CCG AGC GAC CAG TAAATGGCTT
Trp Ser Asp Leu Cys Pro Thr Tyr Asp Ala Leu Asp Pro Ser Asp Gln 2241       2251       2261       2271       2281       2291       2301
GCGCCGGTCG ATGATAGGAT ATGGACGGTG AGTTCGCACT TGCAATACGG ACTCTCGCCT CATTATGGTT 2311       2321       2331       2341       2351       2361       2371
ACACACTCGC TCTGGATCTC TCGCCTGTCG ACAGAACAAA CTTGTATAAT TCGCTTAATG GTTGAAACAA 2381       2391       2401       2411
ATGGAATATT GGGGTACTAT GCACGCATCT CGCTGGGTGA GCTTTCGT
```

Fig. 1F

```
                10                  20                  30                  40                  50                  60                  70
GCGGGCGCACA AACCGTGGGA GCCAACACAC TCCCGTCCAC TCTCACACTG GCCAGATTCG CGGGACCGCC 80                  90                 100                 110                 120                 130                 140
GCCTTTCAGG CCCAAACAGA TCTGGCAGGT TTCGATGGCG CACGCCGCCG TGCCTGCCGG ATTCAATTGT 150                 160                 170                 180                 190                 200                 210
GCGCCAGTCG GGCATCCGGA TGGCTCTACC AGCGCGGTTG ACTGGAAGAG AACACCGAGG TCATGCATTC 220                 230                 240                 250                 260                 270                 280
TGGCCAAGTG CGGCCAAAGG ACCGCTCGCT GGTGCCGGATA CTTAAAGGGC GGGGCGGGGA GGCCTGTCTA 290                 300                 310                 320                 330                 340                 350
CCAAGCTCAA GCTCGCCTTG GGTTCCCAGT CTCCGCCACC CTCCCTCTTCC CCCACACAGT CGCTCCATAG 360       369       378       387       396       405
                   CACCGTCGGC GCC ATG GGT CTG CAG CGA TTC AGC TTC TTC GTC ACC CTC GCG CTC
                              Met Gly Leu Gln Arg Phe Ser Phe Phe Val Thr Leu Ala Leu 414       423       432       441       450       459
GTC GCT CGC TCT CTT GCA GCC ATC GGG GCG CCG GTG AGC CTC GTC GTC GCG AAC
Val Ala Arg Ser Leu Ala Ala Ile Gly Ala Pro Val Ser Leu Val Val Ala Asn 468       477       486       495       504       513
GCC CCC GTC TCG CCC GAC GGC TTC CTT CGG GAT GCC ATC GTG GTC AAC GGC GTG
Ala Pro Val Ser Pro Asp Gly Phe Leu Arg Asp Ala Ile Val Val Asn Gly Val
```

Fig. 2A

```
        522           531          540                      553                 563         573
GTC CCT TCC CCG CTC ATC ACC GGG AAG AAG GTCGGGCGTGT TCGTCGTCGT CCTACTCCTT
Val Pro Ser Pro Leu Ile Thr Gly Lys Lys 583          592          601          610          619          628
TGCTGACAGC GATCTACAG GGA GAC CGC TTC CAG CTC AAC GTC GTC GAC ACC TTG
                     Gly Asp Arg Phe Gln Leu Asn Val Val Asp Thr Leu 637          646          655                      671          681          691
ACC AAC AGC ATG CTC AAG TCC ACT AGT ATC GTAAGTGTGA CGATCCGAAT GTGACATCAA
Thr Asn Ser Met Leu Lys Ser Thr Ser Ile 701          711          721          730          739          748
TCGGGGCTAA TTAACCGCGC ACAG CAC TGG CAC GGC TTC TTC CAG GCA GGC ACC AAC
                           His Trp His Gly Phe Phe Gln Ala Gly Thr Asn 757          766          775          784          793          802
TGG GCA GAA GGA CCC GCG TTC GTC AAC CAG TGC CCT ATT GCT TCC GGG CAT TCA
Trp Ala Glu Gly Pro Ala Phe Val Asn Gln Cys Pro Ile Ala Ser Gly His Ser 811          820          829                      846          856
TTC CTG TAC GAC TTC CAT GTG CCC GAC CAG GCA G GTAAGCAGGA TTTTCTGGGG
Phe Leu Tyr Asp Phe His Val Pro Asp Gln Ala Gly 866          876          886          896          905          914
TCCCCGTGTG ATGCAATGTT CTCATGCTCC GACGTGATCG ACAG GG ACG TTC TGG TAC CAC
                                                  Thr Phe Trp Tyr His
```

Fig. 2B

```
      923              932              941              950              959              968
AGT CAT CTG TCT ACG CAG TAC TGT GAC GGG CTG CGG GGG CCG TTC GTC GTG TAC
Ser His Leu Ser Thr Gln Tyr Cys Asp Gly Leu Arg Gly Pro Phe Val Val Tyr 977              986              995             1004             1013             1024
GAC CCC AAG GAC CCG CAC GCC AGC CGT TAC AGC CGT TAC GAT GTT GAC AAT G   GTACGTGCGC
Asp Pro Lys Asp Pro His Ala Ser Arg Tyr Asp Val Asp Asn Glu 1034             1044             1054             1064             1075             1084
CACGGAGTAT ATCACACAGC ATGGCGTTGAC GTCGGGCCAA CAG AG AGC ACG GTC ATC ACG
                                                 Ser Thr Val Ile Thr 1093             1102             1111             1120             1129             1141
TTG ACC GAC TGG TAC CAC ACC GCT GCC CGG CTC GGT CCC AAG TTC CC  GTAAGCTCGC
Leu Thr Asp Trp Tyr His Thr Ala Ala Arg Leu Gly Pro Lys Phe Pro 1151             1161             1171             1181             1190             1199
AATGGCTTAG TGTTCACAGG TTCTTTGCTT ATGTTGCTTC GATAG A CTC GGC GCG GAC GCC
                                                  Leu Gly Ala Asp Ala 1208             1217             1226             1235             1244             1253
ACG CTC ATC AAC GGT CTG GGG CGG TCG GCC TCG ACT CCC ACC GCT GCG CTT GCC
Thr Leu Ile Asn Gly Leu Gly Arg Ser Ala Ser Thr Pro Thr Ala Ala Leu Ala 1262             1271             1280             1292             1302             1312
GTG ATC AAC GTC CAG CAC GGA AAG CG  GTGAGCATTC TCTTGTATGC CATTTCAATG
Val Ile Asn Val Gln His Gly Lys Arg
```

Fig. 2C

```
      1322            1332            1341            1351            1360            1369
CTTTGTGCTG ACCTATCGGA ACCGGCGCAG C TAC CGC TTC CGT CTC GTT TCG ATC TCG
                                     Tyr Arg Phe Arg Leu Val Ser Ile Ser 1378            1387            1396            1405            1414            1423
TGT GAC CCG AAC TAC ACG TTC AGC ATC GAC GGG CAC AAC CTG ACC GTC ATC GAG
Cys Asp Pro Asn Tyr Thr Phe Ser Ile Asp Gly His Asn Leu Thr Val Ile Glu 1432            1441            1450            1459            1468            1477
GTC GAC GGC ATC AAT AGC CAG CCT CTC CTT GTC GAC TCT ATC CAG ATC TTC GCC
Val Asp Gly Ile Asn Ser Gln Pro Leu Leu Val Asp Ser Ile Gln Ile Phe Ala 1486            1495            1508            1518            1528            1538
GCA CAG CGC TAC TCC TTC GTG GTAAGTCCTG GCTTGTCGAT GCTCCAAAGT GGCCTCACTC
Ala Gln Arg Tyr Ser Phe Val 1548            1559            1568            1577            1586
ATATACTTTC GTTAG TTG AAT GCG AAT CAA ACG GTG GGC AAC TAC TGG GTT CGT
                 Leu Asn Ala Asn Gln Thr Val Gly Asn Tyr Trp Val Arg 1595            1604            1613            1622            1631            1640
GCG AAC CCG AAC TTC GGA ACG GTT GGG TTC GCC GGG GGG ATC AAC TCC GCC ATC
Ala Asn Pro Asn Phe Gly Thr Val Gly Phe Ala Gly Gly Ile Asn Ser Ala Ile 1649            1658            1667            1676            1685            1694
TTG CGC TAC CAG GGC GTC GCC GCA CCG GTC GCC GAG CCT ACC ACG ACC CAG ACG CCG TCG
Leu Arg Tyr Gln Gly Val Ala Pro Val Ala Glu Pro Thr Thr Thr Gln Thr Pro Ser
```

Fig. 2D

```
1703                 1712             1721             1730              1739                      1748               1761
GTG ATC CCG CTC ATC GAG ACG AAC TTG CAC CCG CTC GCG CGC ATG CCA GTG GTATGTCTCT
Val Ile Pro Leu Ile Glu Thr Asn Leu His Pro Leu Ala Arg Met Pro Val 1771             1781             1791             1801              1811                      1821
TTTTCTGATC ATCTGAGTTG CCCGTTGTTG ACCGCATTAT GTGTTACTAT CTAG CCT GGC AGC          1882
                                                                Pro Gly Ser 1830             1839             1848             1857              1866                      1882
CCG ACA CCC GGG GGC GTC GAC AAG GCG CTC AAC CTC GCG TTT AAC TTC GTAAGTATCT
Pro Thr Pro Gly Gly Val Asp Lys Ala Leu Asn Leu Ala Phe Asn Phe 1892             1902             1912             1922              1931                      1940
CTACTACTTA GGCTGGAGGC TCGTCGCTGA TCATACGGTG CTTCAG AAC GGC ACC AAC TTC
                                                     Asn Gly Thr Asn Phe 1949             1958             1967             1976              1985                      1994
TTC ATC AAC AAC GCG ACT TTC ACG CCG ACC GTC CCG ACC GTA CTC CTC CAG ATT
Phe Ile Asn Asn Ala Thr Phe Thr Pro Thr Val Pro Thr Val Leu Leu Gln Ile 2003             2012             2021             2030              2039                      2048
CTG AGC GGT GCG CAG ACC GCA CAA GAC CTG CTC CCC GCA GGC TCT GTC TAC CCG
Leu Ser Gly Ala Gln Thr Ala Gln Asp Leu Leu Pro Ala Gly Ser Val Tyr Pro 2057             2066             2075             2084              2093                      2102
CTC CCG GCC CAC TCC ACC ATC GAG ATC ACG CCC GCG ACC GCC TTG GCC CCG
Leu Pro Ala His Ser Thr Ile Glu Ile Thr Leu Pro Ala Thr Ala Leu Ala Pro
```

Fig. 2E

```
     2111           2120           2129           2145           2155      2165
GGT GCA CCG CAC CCC TTC CAC CTG CAC GGT GTATGTTCCC CTGCCTTCCC TTCTTATCCC
Gly Ala Pro His Pro Phe His Leu His Gly 2175           2185           2195           2204           2213      2222
CGAACCAGTG CTCACGTCCG TCCCATCTAG CAC GCC TTC GCG GTC GTT CGC AGC GCG
                                 His Ala Phe Ala Val Val Arg Ser Ala 2231           2240           2249           2258           2267      2276
GGG AGC ACC ACG TAT AAC GAC CCG ATC TTC CGC GAC GTC GTG AGC ACG
Gly Ser Thr Thr Tyr Asn Asp Pro Ile Phe Arg Asp Val Val Ser Thr 2285           2294           2303           2312           2321      2330
GGC ACG CCC GCC GCG GGC GAC AAC GTC ACG ATC CGC TTC CAG ACG GAC AAC CCC
Gly Thr Pro Ala Ala Gly Asp Asn Val Thr Ile Arg Phe Gln Thr Asp Asn Pro 2339           2348           2357           2366           2375      2384
GGG CCG TGG TTC CTC CTC CAC TGC CAC ATC GAC TTC CAC CTC GAC GCA GGC TTC GCG
Gly Pro Trp Phe Leu His Cys His Ile Asp Phe His Leu Asp Ala Gly Phe Ala 2393           2402           2411           2420           2429      2438
ATC GTG TTC GCA GAG GAC GTT GCG GAC GTG AAG GCG AAC CCG GTT CCG AAG
Ile Val Phe Ala Glu Asp Val Ala Asp Val Lys Ala Asn Pro Val Pro Lys 2447           2456           2465           2474           2483      2499
GCG TGG TCG GAC CTG TGC CCG ATC TAC GAC GGG CTG AGC GAG GCT AAC CAG TGAGCGGAGG
Ala Trp Ser Asp Leu Cys Pro Ile Tyr Asp Gly Leu Ser Glu Ala Asn Gln
```

Fig. 2F

```
        2509       2519       2529       2539       2549       2559       2569
GCGTGGTGTT GAGCGTAAAG CTCGGGCGTC GACCTGGGGG GTTGAAGGTG TTCTGATTGA AATGGTCTTT
        2579       2589       2599       2609       2619       2629       2639
GGGTTTATTT GTTGTTATTC TAACTCGGTT CTCTACGCAA GGACCGAGGA TTGTATAGGA TGAAGTAACT
        2649       2659       2669       2679       2689
TTCCTAATGT ATTATGATAT CAATTGACGG AGGCATGGAC TGCGAAGTGT
```

Fig. 2G

```
         10          20          30          40          50          60          70
TTTCCCGACT AAACCAATCT CAGNCCGCTT CCTCCTAGGG AACCGAGCGA TGTGGCGGCC CTCTCTATCC 80          90         100         110         120         130         140
AAGCTGTCCA TAAGAAGACG TTCAAATGCC GCAGCAAGCG AGGAAATAAG CATCTAACAG TGTTTTTCCC 150         160         170         180         190         200         210
ATAGTCGCAT TTGCGCCGCC TGTCGGACCG ACGCCCCTAG AGCGCTTTGG GAAACGTCGC AAGTGGCGGG 220         230         240         250         260         270         280
TGTTATTCGT GTAGACGAGA CGGTATTTGT CTCATCATTC CCGTGCTTCA GGTTGACACA GCCCAAAGGT 290         300         310         320         330         340         350
CTATGTACGG CCCTTCACAT TCCCTGACAC ATTGACGCAA CCCTCGGTGC GCCTCCGACA GTGCCTCGGT 360         370         380         390         400         410         420
TGTAGTATCG GGACGCCCTA GGATGCAAGA TTGGAAGTCA CCAAGGCCCG AAGGGTATAA AATACCGAGA 430         440         450         460         470         480
GGTCCTACCA CTTCTGCATC TCCAGTCGCA GAGTTCCTCT CCCTTGCCAG CCACAGCTCG AG 491         500         509         518         527         536
ATG TCC TTC TCT AGC CTT CGC CGT CTT CGC CTG GTT TTC CTG GGT GCT TGC AGC AGT
Met Ser Phe Ser Ser Leu Arg Arg Leu Arg Ala Leu Val Phe Leu Gly Ala Cys Ser Ser 545         554         563         572         581         590
GCG CTG GCC TCC ATC GGC CCA GTC ACT GAG CTC GAC ATC GTT AAC AAG GTC ATC
Ala Leu Ala Ser Ile Gly Pro Val Thr Glu Leu Asp Ile Val Asn Lys Val Ile
```

Fig. 3A

```
       599             608             617             626             635             644
GCC CCG GAT GGC GTC GCT CGT GAT ACA GTC CTC GCC GGG GGC ACG TTC CCG GGC
Ala Pro Asp Gly Val Ala Arg Asp Thr Val Leu Ala Gly Gly Thr Phe Pro Gly 653             662             675             685             695             705
CCA CTC ATC ACA GGA AAG AAG GTATGCTAAG TAGTCCCGCC CCCATCATCC TGTGGCTGAC
Pro Leu Ile Thr Gly Lys Lys 715             726             735             744             753
GTTCGACGCC GCCAG GGT GAC AAC TTC CGC ATC AAC GTC GTC GAC AAG TTG GTT
                 Gly Asp Asn Phe Arg Ile Asn Val Val Asp Lys Leu Val 762             771             780             789             799             809             819
AAC CAG ACT ATG CTG ACA TCC ACC ACC ATT GTATGTCACT AGCTCTCGCT ATCTCGAGAC
Asn Gln Thr Met Leu Thr Ser Thr Thr Ile 829             839             848             857             866             875
CCGCTGACCG ACAACATTTG CCGTAG CAC TGG CAC GGG ATG TTC CAG CAT ACG ACG
                             His Trp His Gly Met Phe Gln His Thr Thr 884             893             902             911             920             929
AAC TGG GCG GAT GGT CCC GCC TTT GTG ACT CAA TGC CCT ATC ACC ACT GGT GAT
Asn Trp Ala Asp Gly Pro Ala Phe Val Thr Gln Cys Pro Ile Thr Thr Gly Asp 938             947             956             965             976             986
GAT TTC CTG TAC AAC TTC CGC GTG CCC GAC CAG ACA G  GTACGCAAAG GGCAGCATGC
Asp Phe Leu Tyr Asn Phe Arg Val Pro Asp Gln Thr Gly
```

Fig. 3B

```
      996           1006          1016          1026         1035        1044
GTACTCAAAG ACATCTCTAA GCATTGCTA CCTAG GA ACG TAC TGG TAC CAT AGC CAT
                                        Thr Tyr Trp Tyr His Ser His 1053         1062         1071         1080         1089        1098
CTG GCC TTG CAG TAC TGT GAT GGG CTT CGC GGC CTG CCC CTG GTG ATT TAC GAT CCC
Leu Ala Leu Gln Tyr Cys Asp Gly Leu Arg Gly Leu Pro Leu Val Ile Tyr Asp Pro 1107         1116         1125         1134                     1155
CAT GAT CCG CAG GCA TAC CTG TAT GAC GTC GAT GAC G    GTACGCAGCA CAGTTTCCCT
His Asp Pro Gln Ala Tyr Leu Tyr Asp Val Asp Asp Glu 1165          1175          1185          1198            1207
AAAACGGTTA ACTTCTAATT CTGTAAATAT CTTCATAG AG AGC ACC GTT ATC ACT CTG
                                             Ser Thr Val Ile Thr Leu 1216         1225         1234         1243         1252         1267
GCA GAC TGG TAC CAT ACC CCG GCG CCT CTG CTG CCG CCT GCC GC  GTACGCCTCC
Ala Asp Trp Tyr His Thr Pro Ala Pro Leu Leu Pro Pro Ala Ala 1277          1287          1297          1307        1317       1328
ACACATCTGC ACAGCGTTCC GTATCTCATA CCCTTAAAGT TTATCGGACA G C ACT TTG ATT
                                                           Thr Leu Ile 1337         1346         1355         1364         1373         1382
AAT GGC CTG GGT CGC TGG CCT GGC AAC CCC ACC GAC CTA GCC GTC ATC GAA
Asn Gly Leu Gly Arg Trp Pro Gly Asn Pro Thr Asp Leu Ala Val Ile Glu
```

Fig. 3C

```
            1391              1409       1419       1429       1439       1449
GTC CAG CAC GGA AAG CG  GTATGTCATA GCTCGGTTAT CTATTCATAC TCGCGGCCTC GAAGCTAAAA
Val Gln His Gly Lys Arg 1459              1470       1479       1488       1497
CCTTGTTCCA G C TAC CGG TTC CGA CTG GTC AGC ACC TCA TGC GAC CCC AAC TAC
            Tyr Arg Phe Arg Leu Val Ser Thr Ser Cys Asp Pro Asn Tyr 1506       1515                1524              1533              1542          1551
AAC TTC ACT ATC GAT GGC CAC ACC ATG ACA ATC ATC GAG GCG GAT GGG CAG AAC
Asn Phe Thr Ile Asp Gly His Thr Met Thr Ile Ile Glu Ala Asp Gly Gln Asn 1560              1569              1578              1587              1596          1605
ACC CAG CCA CAC CAA GTC GAC GGA CTT CAG ATC TTC GCG GCA CAG CGG TAC TCC
Thr Gln Pro His Gln Val Asp Gly Leu Gln Ile Phe Ala Ala Gln Arg Tyr Ser 1614              1627              1637              1647              1657          1667
TTC GTT GTATGTTTTC CGCATTTCGG GAAAAGGAAT TGCGCTGACA GCTCGAGTGT GCGTAG
Phe Val 1676              1685              1694              1703              1712          1721
CTT AAC GCT AAC CAA GCG GTC AAC AAC TAC TGG ATC CGT GCG AAC CCT AAC CGT
Leu Asn Ala Asn Gln Ala Val Asn Asn Tyr Trp Ile Arg Ala Asn Pro Asn Arg 1730              1739              1748              1757              1766          1775
GCT AAC ACT ACG GGC TTC GCC AAC GGC ATC AAC TCC GCC ATC CTG CGC TAC AAG
Ala Asn Thr Thr Gly Phe Ala Asn Gly Ile Asn Ser Ala Ile Leu Arg Tyr Lys
```

Fig. 3D

```
1784            1793                1802                1811                1820                1829
GGG GCG CCG ATT AAG GAG CCT ACG ACG AAC CAG ACT ACC ATC CGG AAC TTT TTG
Gly Ala Pro Ile Lys Glu Pro Thr Thr Asn Gln Thr Thr Ile Arg Asn Phe Leu 1838            1847                1856                1865                1874                1884            1894
TGG GAG ACG GAC TTG CAC CTC ACT GAC CCA CGT GCA GTAAGTTCTA CACAGTCACC
Trp Glu Thr Asp Leu His Pro Leu Thr Asp Pro Arg Ala 1904                1914                1924                1933                1942                1951
AACGGTGAGC TGTTGTCTGA TTGCACTGTG TTATAG CCT GGC CTT CCT TTC AAG GGG GGC
                                        Pro Gly Leu Pro Phe Lys Gly Gly 1960                1969                1978                1987                1997                2007            2017
GTT GAC CAC GCT TTG AAC CTC ACT TTC GTACGTAGCG CCTCAGATAT CGAGTAGTCT
Val Asp His Ala Leu Asn Leu Thr Phe 2027                2037                2046                2055                2064                2073
ATCTCCTGAC CGATTGACAG AAT GGA TCG GAG TTC TTC ATC AAC GAT GCG CCT TTC
                      Asn Gly Ser Glu Phe Phe Ile Asn Asp Ala Pro Phe 2082                2091                2100                2109                2118                2127
GTC CCT CCG ACT GTC CCG GTG CTA CTG CAG ATC CTG AAC GGA ACG CTC GAC GCG
Val Pro Pro Thr Val Pro Val Leu Leu Gln Ile Leu Asn Gly Thr Leu Asp Ala 2136                2145                2154                2163                2172                2181
AAC GAC CTC CTG CCG CCC GGC AGC GTC TAC AAC CTT CCT CCG GAC TCC ACC ATC
Asn Asp Leu Leu Pro Pro Gly Ser Val Tyr Asn Leu Pro Pro Asp Ser Thr Ile
```

Fig. 3E

```
     2190          2199          2208          2217          2226          2235
GAG CTG TCC ATT CCC GGA GGT GTG ACG GGT GGC CCG CAC CCA TTC CAT TTG CAC
Glu Leu Ser Ile Pro Gly Gly Val Thr Gly Gly Pro His Pro Phe His Leu His 2248          2258          2268          2278          2288          2297
GGG GTAATAATCT CTCTTTATAC TTTGGTCTCC CGATGCTGAC TTTCACTGCT CATCTTCAG
Gly 2306          2315          2324          2333          2342          2351
CAC GCT TTC TCC GTC GTG CGT AGC GCC GGC AGC ACC GAA TAC AAC TAC GCG AAC
His Ala Phe Ser Val Val Arg Ser Ala Gly Ser Thr Glu Tyr Asn Tyr Ala Asn 2360          2369          2378          2387          2396          2405
CCG GTG AAG CGC GAC GAC GTC AGC AGC ATT GGT CTT GGT GAC AAC GTC ACC GTG
Pro Val Lys Arg Asp Asp Val Ser Ser Ile Gly Leu Ala Gly Asp Asn Val Thr Val 2414          2424          2434          2444          2454          2464
CGC TTC GTG GTATGTTTTA CAGCCCTCTCT ATCTCCGTGG GCGTTCGGAA GTTGACTGGG CGCGTAG
Arg Phe Val 2474          2483          2492          2501          2510          2519
ACC GAC AAC CCC GGC CCG TGG TTC CTC CAC TGT CAC ATC GAC TTC CAT TTG CAA
Thr Asp Asn Pro Gly Pro Trp Phe Leu His Cys His Ile Asp Phe His Leu Gln 2528          2537          2546          2555          2564          2573
GCA GGC CTC GCC ATC GTG TTC GCG GAG GAC GCG CAG GAC ACG AAG CTT GTG AAC
Ala Gly Leu Ala Ile Val Phe Ala Glu Asp Ala Gln Asp Thr Lys Leu Val Asn
```

Fig. 3F

```
2582            2599            2609            2619            2629            2639
CCC GTC CCT G   GTACGTCTTC      TGGATGCATG      CGCTCCGCAC      AGTGACTCAT      CTTTTGCAAC
Pro Val Pro Glu 2649            2658            2667            2676            2685
AG AG GAC TGG   AAC AAG CTG   TGC CCC ACC   TTC GAT AAG   GCG ATG AAC   ATC ACG
   Asp Trp    Asn Lys Leu   Cys Pro Thr   Phe Asp Lys   Ala Met Asn   Ile Thr 2694            2704            2714            2724            2734            2744            2754
GTT TGAGCGATGC  GTGGCGCTCA      TGGTCATTTT      CTTGGAATCT      TTGCATAGGG      CTGCAGCACG
Val 2764            2774            2784            2794            2804            2814            2824
CTGGATACTC      TTTCCCTTAG      CAGGATATTA      TTTAATGACC      CCTGGCGTTTA     GTGCTTAGTT      AGCTTTACTA
      2834            2844            2854            2864            2874            2884            2894
CTGGTTGTAA      TGTACGCAGC      ATGCGTAATT      CGGATAAATGC     TATCAATGTG      TATATTATGA      CACGCGGTCAT
      2904            2914            2924            2934            2944            2954            2964
GCGCGATGCT      TGAGTTGCAA      GGTCGGTTTC      CGATGCTCGA      CATAAACGTT      TCACTTACAT      ACACATTGGG
      2974            2984            2994            3004            3014            3024            3034
TCTAGAACTG      GATCTATCCA      TGTATACAAA      AACTCCTCAT      ACAGCTGACT      GGGGCGCTCT      AGAGCATGGG
      3044            3054            3064            3074            3084            3094            3104
TCCGATTGAT      CAGATGTCGC      GAACACGAGC      CTCCTGAGCT      CGAGGACTCT      GAGAAGCGGC      GGTGCGTTCT
```

Fig. 3G

```
         10          20         30         40         50         60         70
GCGCGGTTGGC CGATTCATTA ATGCAGCTGG CACGACAGGT TTCCCGACTG GAAAGCGGGC AGTGAGCGCA 80          90        100        110        120        130        140
ACGCAATTAA TGTGAGTTAG CTCACTCATT AGGCACCCCA GGCTTTACAC TTTATGCTTC CGGCTCGTAT 150         160        170        180        190        200        210
GTTGTGTGGA ATTGTGAGCG GATAACAATT TCACACAGGA AACAGCTATG ACATGATTAC GAATTCCGAT 220         230        240        250        260        270        280
CGGCTTGCCC TCATTCCTCC ATGTTCCCCC GACCGAGCGG GCGCGTCAAT GGCCCGTTTG CGAACACATA 290         300        310        320        330        340        350
TGCAGGATAA ACAGTGCGAA ATATCAATGT GGCGGGCGACA CAACCCTCGCC GGCCGACACT CGACGCTGTT 360         370        380        390        400        410        420
GATCATGATC ATGTCTTGTG AGCATTCTAT ACGCAGCCTT GGAAATCTCA GGCGAATTTG TCTGAATTGC 430         440        450        460        470        480        490
GCTGGGAGGC TGGCAGCGCA GATCGGTGTG TCGGTGCAGT AGCCGACGCA CACCTGGCG GAAGCCGACA 500         510        520        530        540        550        560
TCTCGGGTAC GACTTGATCT CCGCCAGATC ACTGCGGTTC CGCCATCGGC CGCGGGCCC ATTCTGTGTG 570         580        590        600        610        620        630
TGCGCTGTAG CACTCTGCAT TCAGGCTCAA CGTATCCATG CTAGAGGACC GTCCAGCTGT TGGCGCACGA

Fig. 4A
```

```
                    640           650           660           670           680           690           700
         TTCGCGCAGA AAGCTGTACA GGCAGATATA AGGATGTCCG TCCGTCAGAG ACTCGTCACT CACAAGCCTC 710           720           730           740           750           760           770
         TTTCCTCTT CGCCTTTCCA GCCTCTTCCA ACGCCTGCCA TCGTCCCTCTT AGTTCGCTCG TCCATTCTTT 780           790           799    808           817    826
         CTGCGTAGTT AATC ATG GGC AGG TTC TCA TCT CTC TGC GCG CTC ACC GCC GTC ATC
                         Met Gly Arg Phe Ser Ser Leu Cys Ala Leu Thr Ala Val Ile 835                  844           853           862           871    880
         CAC TCT TTT GGT CGT GTC TCC GCC GCT ATC GGG CCT GTG ACC GAC CTC ACC ATC
         His Ser Phe Gly Arg Val Ser Ala Ala Ile Gly Pro Val Thr Asp Leu Thr Ile 889                  898           907           916           925    934
         TCC AAT GGG GAC GTT TCT CCC GAC GGC TTC ACT CGT GCC GCA GTG CTT GCA AAC
         Ser Asn Gly Asp Val Ser Pro Asp Gly Phe Thr Arg Ala Ala Val Leu Ala Asn 943                  952           961           970           980    990
         GGC GTC TTC CCG GGT GGT CCT CTT ATC ACG GGA AAC AAG GTACGTGGCA TGCGTTCAGT
         Gly Val Phe Pro Gly Gly Pro Leu Ile Thr Gly Asn Lys 1000          1010          1020          1029          1038          1047
         CTACACCCTA CAAGCCTTCT AACTCTTTTA CCACAG GGC GAC AAC TTC CAG ATC AAT GTT
                                                 Gly Asp Asn Phe Gln Ile Asn Val
```

Fig. 4B

```
      1056           1065           1074           1083           1092           1105
ATC GAC AAC CTC TCT AAC GAG ACG ATG TTG AAG TCG ACC TCC ATC GTATGTGCTT
Ile Asp Asn Leu Ser Asn Glu Thr Met Leu Lys Ser Thr Ser Ile 1115           1125           1135           1145      1156      1165
CTACTGCTTC TTAGTCTTGG CAATGGCTCA AGGTCTCCTC CGCAG CAT TGG CAC GGC TTC
                                                        His Trp His Gly Phe 1174           1183           1192           1201           1210           1219
TTC CAG AAG GGT ACT AAC TGG GCT GAT GGA GCT GCC TTC GTC AAC CAG TGC CCT
Phe Gln Lys Gly Thr Asn Trp Ala Asp Gly Ala Ala Phe Val Asn Gln Cys Pro 1228           1237           1246           1255           1264
ATC GCG ACG GGG AAC TCT TTC CTT TAC GAC TTC TAC ACC GCG ACG GAC CAA GCA G
Ile Ala Thr Gly Asn Ser Phe Leu Tyr Asp Phe Tyr Thr Ala Thr Asp Gln Ala Gly 1281           1291      1301           1311           1321           1331
GTCAGTGCCT GTGGCGCTTA TGTTTTCCCG TAATCAGCAG CTAACACTCC GCACCCACAG GC 1342           1351           1360           1369           1378           1387
ACC TTC TGG TAC CAC AGT CAC TTG TCT ACG CAG TAC TGC GAT GGT TTG CGG GGC
Thr Phe Trp Tyr His Ser His Leu Ser Thr Gln Tyr Cys Asp Gly Leu Arg Gly 1396           1405           1414           1423           1432           1441
CCG ATG GTC GTA TAC GAC CCG AGT GAC CCG CAT GCG GAC CTT TAC GAC GTC GAC
Pro Met Val Val Tyr Asp Pro Ser Asp Pro His Ala Asp Leu Tyr Asp Val Asp
```

Fig. 4C

```
                    1450              1459              1468              1477              1486              1495
            GAC GAG ACC ACG ATC ATC ACG CTC TCT GAT TGG TAT CAC ACC GCT GCT TCG CTC
            Asp Glu Thr Thr Ile Ile Thr Leu Ser Asp Trp Tyr His Thr Ala Ala Ser Leu 1504              1519              1529              1539              1549              1559
            GGT GCT GCC TTC CC  GTAAGTTTAC CCCAGCGCAC GGAGTTAAGA CCGGATCTAA CTGTAATACG
            Gly Ala Ala Phe Pro 1568              1577              1586              1604              1614
            TTCAG G ATT GGC TCG GAC TCT ACC CTG ATT AAC GG  GTTGGCCGCT TCGCGGGTGG
                    Ile Gly Ser Asp Ser Thr Leu Ile Asn Gly 1624              1633              1642              1651              1669
            TGACAG C ACT GAC CTT GCG GTT ATC GCT ACT GTC GAG CAG GGC AAG CG  GTTAGTGATA
                     Thr Asp Leu Ala Val Ile Thr Val Glu Gln Gly Lys Arg 1679              1689              1699              1709              1719              1728
            CCCTCTACAG TTGACACTGT GCCATTGCTG ACAGTACTCT CAG C TAC CGT ATG CGT CTT
                                                              Tyr Arg Met Arg Leu 1737              1746              1755              1764              1773              1782
            CTC TCG CTG TCT TGC GAC CCC AAC TAT GTC TTC TCC ATT GAC GGC CAC AAC ATG
            Leu Ser Leu Ser Cys Asp Pro Asn Tyr Val Phe Ser Ile Asp Gly His Asn Met 1791              1800              1809              1818              1827              1836
            ACC ATC ATC GAG GCC GAC GCC GTC AAC CAC GAG CCC CTC ACG GTT GAC TCC ATC
            Thr Ile Ile Glu Ala Asp Ala Val Asn His Glu Pro Leu Thr Val Asp Ser Ile
```

Fig. 4D

```
                    1845           1854           1863                      1879           1889           1899
               CAG ATC TAC GCC GGC CAA CGT TAC TCC TTC GTC GTACGTATTC CGAACAGCCA TGATCACGCC
               Gln Ile Tyr Ala Gly Gln Arg Tyr Ser Phe Val 1909           1919           1928                      1937           1946           1955
               AAGCCCGATG CTAACGCGCC TACCCTCAG CTT ACC GCT GAC CAG GAC ATC GAC AAC TAC
                                                Leu Thr Ala Asp Gln Asp Ile Asp Asn Tyr 1964           1973           1982                      1991           2000           2009
               TTC ATC CGT GCC CTG CCC AGC GCC GGT ACC ACC TCG TTC GAC GGC GGC ATC AAC
               Phe Ile Arg Ala Leu Pro Ser Ala Gly Thr Thr Ser Phe Asp Gly Gly Ile Asn 2018           2027           2036                      2045           2054           2063
               TCG GCT ATC CTG CGC TAC TCT GGT GCC TCC GAG GTT GAC GCC ACG ACC ACG GAG
               Ser Ala Ile Leu Arg Tyr Ser Gly Ala Ser Glu Val Asp Pro Thr Thr Thr Glu 2072           2081           2090                      2099           2108           2117
               ACC ACG AGC GTC CTC CCC CTC GAC GAG GCG AAC CTC GTG CCC CTT GAC AGC CCC
               Thr Thr Ser Val Leu Pro Leu Asp Glu Ala Asn Leu Val Pro Leu Asp Ser Pro 2126           2136           2146                      2156           2166           2176
               GCT GCT GTACGTCGTA TTCTGCGCTT GCAAGGATCG CACACATACTAA CATGCTCTTG TAG CCC
               Ala Ala                                                                   Pro 2185           2194           2203                      2212           2221           2230
               GGT GAC CCC AAC ATT GGC GGT GTC GAC TAC GCG CTG AAC TTG GAC TTC AAC TTC
               Gly Asp Pro Asn Ile Gly Gly Val Asp Tyr Ala Leu Asn Leu Asp Phe Asn Phe
```

Fig. 4E

```
2239           2248           2257           2266           2275          2284
GAT  GGC  ACC  AAC  TTC  TTC  ATC  AAC  GAC  GTC  TCC  TTC  GTG  TCC  CCC  ACG  GTC  CCT
Asp  Gly  Thr  Asn  Phe  Phe  Ile  Asn  Asp  Val  Ser  Phe  Val  Ser  Pro  Thr  Val  Pro 2293           2302           2311           2320           2329          2338
GTC  CTC  CTC  CAG  ATT  CTT  AGC  GGC  ACC  ACC  TCC  GCG  GCC  GAC  CTT  CTC  CCC  AGC
Val  Leu  Leu  Gln  Ile  Leu  Ser  Gly  Thr  Thr  Ser  Ala  Ala  Asp  Leu  Leu  Pro  Ser 2347           2356           2365           2374           2383          2392
GGT  AGT  CTC  TTC  GCG  GTC  CCG  TCC  AAC  ACG  ATC  GAG  ATC  TCG  TTC  CCC  ATC
Gly  Ser  Leu  Phe  Ala  Val  Pro  Ser  Asn  Thr  Ile  Glu  Ile  Ser  Phe  Pro  Ile 2401           2410           2419           2428           2437          2446     2456
ACC  GCG  ACG  AAC  GCT  CCC  GGC  GCG  CCG  CAT  CCC  TTC  CAC  TTG  CAC  GGT  GTACGTGTCC
Thr  Ala  Thr  Asn  Ala  Pro  Gly  Ala  Pro  His  Pro  Phe  His  Leu  His  Gly 2466           2476           2486           2496           2506           2515
CATCTCATAT  GCTACGGAGC  TCCACGCTGA  CCGCCCTATA  G  CAC  ACC  TTC  TCT  ATC  GTT
                                                   His  Thr  Phe  Ser  Ile  Val 2524           2533           2542           2551           2560          2569
CGT  ACC  GCC  GGC  AGC  GAT  ACG  ACG  AAC  TTC  GTC  AAC  CCC  GTC  CGC  CGC  GAC  GTC
Arg  Thr  Ala  Gly  Ser  Asp  Thr  Thr  Asn  Phe  Val  Asn  Pro  Val  Arg  Arg  Asp  Val 2578           2587           2596           2605           2614          2624
GTG  AAC  ACC  GGT  ACC  GTC  GGC  GAC  AAC  GTC  ACC  ATC  CGC  TTC  ACG  GTACGCAGCA
Val  Asn  Thr  Gly  Thr  Val  Gly  Asp  Asn  Val  Thr  Ile  Arg  Phe  Thr
```

Fig. 4F

```
        2634          2644          2654          2664          2673          2682
CTCTCCTAAC ATTCCCACTG CGCGATCACT GACTCCTCGC CCACAG ACT GAC AAC CCC GGC
                                                   Thr Asp Asn Pro Gly 2691               2700          2709          2718          2727          2736
CCC TGG TTC CTC TGC CAC ATC GAC TTC CAC TTG GAG GCC GGT TTC GCC ATC
Pro Trp Phe Leu His Cys His Ile Asp Phe His Leu Glu Ala Gly Phe Ala Ile 2745          2754          2763          2772          2781              2798
GTC TTC AGC GAG GAC ACC GCC GAC GTC TCG AAC ACG ACC ACG CCC TCG A    GTACGTTGTG
Val Phe Ser Glu Asp Thr Ala Asp Val Ser Asn Thr Thr Thr Pro Ser Thr 2808          2818          2828          2838          2850         2859
CTCCCGTGCC CATCTCCGCG CGCCTGACTA ACGAGCACCC CTTACAG CT GCT TGG GAA GAT
                                                       Ala Trp Glu Asp 2868          2877          2886          2895               2908       2918
CTG TGC CCC ACG TAC AAC GCT CTT GAC TCA TCC GAC CTC TAATCGGTTC AAAGGGTCGC
Leu Cys Pro Thr Tyr Asn Ala Leu Asp Ser Ser Asp Leu 2928          2938          2948          2958          2968          2978         2988
TCGCTACCTT AGTAGGTAGA CTTATGCACC GGACATTATC TACAATGGAC TTTAATTTGG GTTAACGGCC 2998          3008          3018          3028          3038          3048         3058
GTTATACATA CGGCGCACGTA GTATAAAGGT TCTCTGGATT GGTCGGACCT ACAGACTGCA ATTTTCGTGA 3068          3078          3088          3098
CCTATCAACT GTATATTGAA GCACGACAGT GAATGGAAAT AGAGACA
```

Fig. 4G

```
         10                 20                 30                 40                 50                 60                 70
CTCATAACTC         TTCGCTTCTA         GCATGGGGGC         TGCGCACACC         TGACAGACCC         TTCGGGAGGC         GAACTCGAAT 80                 90                100                110                120                130                140
GCAGGCGTACT        CTATCAAAACC        TGCAGGAAAAG        GTAGGGATGG         ACNCCGTGCA         CCAACAACTG         TCTCTCCACC 150                160                170                180                190                200                210
AGCAACCATC         CCTTGGATAT         GTCTCCACAC         ACCCGGTGTC         TACAAGCGGG         GATCTGTGCT         GGTGAAGTGC 220                230                240                250                260                270                280
TGTCTCCGGA         GCGGCGGCGG         CGAGCGACCA         GAACCCGAAC         CAGTGCTAGT         GCCCGACACC         CGCGAGACAA 290                300                310                320                330                340                350
TTGTGCAGGG         TGAGTTATAT         TCTTCGTGAG         ACGGGCGCTGC        GCGTCGGCAC         TGAAAGCCGTC        GCAGTTAGGT 360                370                380                390                400                410                420
GATGCAGCGG         TCCGCGCTAT         TTTTGACGTC         TGGCAGTATC         CCTAAGCCGC         GCCTCCATAC         ACCCCAGGCG 430                440                450                460                470                480                490
CTCTCGTTTG         CTATAGGTAT         AAATCCCCTCA        GCTTCAGAGC         GTCGATCCTC         ATCCCACACG         ACACCCGTTT 500                510                520                530                540                550
CAGTCTTCTC         GTAGCGCATT         CCCTAGCCGC         CCAGCCTCCG         CTTTCGTTTT         CAAC ATG GGC AAG
                                                                                                 Met Gly Lys 559        568        577        586        595        604
TAT CAC TCT TTT GTG AAC GTC GTC GCC CTT TCT AGT CTT TCT TTG AGC GGT CGT GTG
Tyr His Ser Phe Val Asn Val Val Ala Leu Ser Ser Leu Ser Leu Ser Gly Arg Val
```

Fig. 5A

```
       613           622          631          640          649          658
TTC GGC GCC ATT GGG CCC GTC ACC GAC TTG ACT ATC TCT AAC GCC GAT GTT ACG
Phe Gly Ala Ile Gly Pro Val Thr Asp Leu Thr Ile Ser Asn Ala Asp Val Thr 667           676          685          694          703          712
CCT GAC GGC ATT ACT CGT GCT GTC CTC GCG GGC GGC GTT TTC CCC GGG CCC
Pro Asp Gly Ile Thr Arg Ala Val Leu Ala Gly Gly Val Phe Pro Gly Pro 721           730          743                753           763           773          783
CTC ATT ACC GGC AAC AAG GTGAGCCGCG AAACCTTCTA CTAGCGCGCT CGTACGGTGC ACCGTTACTG
Leu Ile Thr Gly Asn Lys 793                803                814                823                832           841
AAGCCACACT TTGCGCTGTC AACAG GGG GAT GAA TTC CAG ATC AAT GTC ATC GAC AAC
                                Gly Asp Glu Phe Gln Ile Asn Val Ile Asp Asn 850          859                868          877                887           897
CTG ACC AAC GAG ACC ATG TTG AAG ACC ACA ATC GTAAGGTGCT TGCTCCCATA
Leu Thr Asn Glu Thr Met Leu Lys Thr Thr Ile 907                917                927           938          947          956
ATTAAGCCCG TCGCTGACTC GAAGTTTATC TGTAG CAC TGG CAT GGT ATC TTC CAG GCC
                                         His Trp His Gly Ile Phe Gln Ala 965          974          983          992          1001          1010
GGC ACC AAC TGG GCA GAC GGC GCG GCC TTC GTG AAC CAG TGC CCT ATC GCC ACG
Gly Thr Asn Trp Ala Asp Gly Ala Ala Phe Val Asn Gln Cys Pro Ile Ala Thr
```

Fig. 5B

```
     1019           1028           1037           1046                    1063
GGA AAC TCG TTC TTG TAC GAC TTC ACC GTT CCT GAT CAA GCC G    GTACGTTTAT
Gly Asn Ser Phe Leu Tyr Asp Phe Thr Val Pro Asp Gln Ala Gly 1073           1083           1093           1103           1112           1121
ACACTTCCCT TTCTGCGGCA TACTCTGACG CGCCGCTGGA TCAG GC ACC TTC TGG TAC CAC
                                                  Thr Phe Trp Tyr His 1130           1139           1148           1157           1166           1175
AGC CAC CTG TCC ACC CAG TAC TGT GAC GGC CTG CGC GGT CCT CTT GTG GTC TAC
Ser His Leu Ser Thr Gln Tyr Cys Asp Gly Leu Arg Gly Pro Leu Val Val Tyr 1184           1193           1202           1211           1220           1231
GAC CCC GAC GAT CCC AAC GCG TCT CTT TAC GAC GTC GAT GAC G    GTAAGCAGGC
Asp Pro Asp Asp Pro Asn Ala Ser Leu Tyr Asp Val Asp Asp 1241           1251           1261           1271           1281           1290
TACTTGTGGA CTTGTATGGA TGTATCTCAC GCTCCCCTAC AG AT ACT ACG GTT ATT ACG
                                                Thr Thr Val Ile Thr 1299           1308           1317           1326           1335           1347
CTT GCG GAC TGG TAC CAC ACT GCG GCG AAG CTG GGC CCT GCC TTC CC GTGAGTCTAC
Leu Ala Asp Trp Tyr His Thr Ala Ala Lys Leu Gly Pro Ala Phe Pro 1357           1367           1377           1387           1397           1408
TCTTCCTCGT GTGTTAACAT AGGTGACGGC CGCTGATACG AGAGCTACCA G C GCG GGT CCG
                                                            Ala Gly Pro
```

Fig. 5C

```
      1417              1426                 1435              1444              1453                  1462
GAT AGC GTC TTG ATC AAT GGT CTT GGT CGG TTC TCC GGC GAT GGT GGA GGA GCG
Asp Ser Val Leu Ile Asn Gly Leu Gly Arg Phe Ser Gly Asp Gly Gly Gly Ala 1471              1480                 1489              1498              1510                  1520
ACA AAC CTC ACC GTG ATC ACC GTC ACG CAA GGC AAA CG  GTGAGTCCGC CCTGAGCTGG
Thr Asn Leu Thr Val Ile Thr Val Thr Gln Gly Lys Arg 1530              1540              1550              1561              1570              1579
CCTCAATAGC GATATTGACG AGTCCATGCC CTCCCAG G TAC CGC TTC CGC CTT GTG TCG
                                           Tyr Arg Phe Arg Leu Val Ser 1588              1597                 1606              1615              1624                  1633
ATC TCG TGC GAC CCC AAC TTC ACG TTC TCG ATC GAC GGG CAC AAC ATG ACC ATC
Ile Ser Cys Asp Pro Asn Phe Thr Phe Ser Ile Asp Gly His Asn Met Thr Ile 1642              1651                 1660              1669              1678                  1687
ATC GAG GTG GAC GGT GTC AAC CAC GAG GCC TTG GAC GTC GAC TCC ATT CAG ATT
Ile Glu Val Asp Gly Val Asn His Glu Ala Leu Asp Val Asp Ser Ile Gln Ile 1696              1705                 1714              1724              1734                  1744
TTT GCG GGG CAG CGG TAC TCC TTC ATC GTACGTTCCC TTGCCCTCGT GCTATATCCG
Phe Ala Gly Gln Arg Tyr Ser Phe Ile 1754              1764              1774              1785              1794              1803
CCCGTCTGCT CACAGAGGCT TCTATATCGC AG CTC AAC GCC AAC CAG TCC ATC GAC AAC
                                      Leu Asn Ala Asn Gln Ser Ile Asp Asn
```

Fig. 5D

```
              1812           1821           1830           1839           1848           1857
TAC TGG ATC CGC GCG ATC CCC AAC ACC GGT ACC ACC GAC ACC ACG GGC ACG GGC GTG
Tyr Trp Ile Arg Ala Ile Pro Asn Thr Gly Thr Thr Asp Thr Thr Gly Gly Val 1866           1875           1884           1893           1902           1911
AAC TCT GCT ATT CTT CGC TAC GAC ACC GCA GAA GAT ATC GAG CCT ACG ACC AAC
Asn Ser Ala Ile Leu Arg Tyr Asp Thr Ala Glu Asp Ile Glu Pro Thr Thr Asn 1920           1929           1938           1947           1956           1965
GCG ACC ACC TCC GTC ATC CCT CTC ACC GAG ACG GAT CTG GTG CCG CTC GAC AAC
Ala Thr Thr Ser Val Ile Pro Leu Thr Glu Thr Asp Leu Val Pro Leu Asp Asn 1974           1983           1992           2001           2010           2019
CCT GCG GCT CCC GGT GAC CCC CAG GTC GGC GGT GTT GAC CTG GCT ATG AGT CTC
Pro Ala Ala Pro Gly Asp Pro Gln Val Gly Gly Val Asp Leu Ala Met Ser Leu 2028           2041           2051           2061           2071           2081
GAC TTC TCC TTC GTGAGTCCCA CAGCACTCCG CGCCATTCCG CTTATTTACG CAGGAGTATT
Asp Phe Ser Phe 2090           2099           2108           2117           2126           2135
GTTCAG AAC GGT TCC AAC TTC TTT ATC AAC AAC GAG ACC TTC GTC CCG CCC ACA
       Asn Gly Ser Asn Phe Phe Ile Asn Asn Glu Thr Phe Val Pro Pro Thr 2144           2153           2162           2171           2180           2189
GTT CCC GTG CTC CTG CTG CAG ATT TTG AGT GGT GCG CAG GAC GCG AGC CTG CTC
Val Pro Val Leu Leu Leu Gln Ile Leu Ser Gly Ala Gln Asp Ala Ser Leu Leu
```

Fig. 5E

```
                    2198              2207              2216              2225              2234              2243
               CCC AAC GGG AGT GTC TAC ACA CTC CCT TCG AAC TCG ACC ATT GAG ATC TCG TTC
               Pro Asn Gly Ser Val Tyr Thr Leu Pro Ser Asn Ser Thr Ile Glu Ile Ser Phe 2252              2261              2270              2279              2288              2297
               CCC ATC ATC ACC ACC GAC GGT GTT CTG AAC GCG CCC GGT GCT CCG CAC CCG TTC
               Pro Ile Ile Thr Thr Asp Gly Val Leu Asn Ala Pro Gly Ala Pro His Pro Phe 2306              2319              2329              2339              2349              2359
               CAT CTC CAC GGC GTAAGTCCTT GCTTTCCTCA GTGCCTCGCT TCCACGACGT CCACTGATCC
               His Leu His Gly 2369              2380              2389              2398              2407              2416
               CACACATCCC ATGTGCAG CAC ACC TTC TCG GTG GTG CGC AGC GCC GGG AGC TCG ACC
                                 His Thr Phe Ser Val Val Arg Ser Ala Gly Ser Ser Thr 2425              2434              2443              2452              2461              2470
               TTC AAC TAC GCC AAC CCA GTC CGC CGG GAC ACC GTC AGT ACT GGT AAC TCT GGC
               Phe Asn Tyr Ala Asn Pro Val Arg Arg Asp Thr Val Ser Thr Gly Asn Ser Gly 2479              2488              2504              2514              2524              2534
               GAC AAC GTC ACT ATC CGC TTC ACG GTACGTCTTC TCCGGAGCCC TCCCACCCGT GTGTCCGCTG
               Asp Asn Val Thr Ile Arg Phe Thr 2544              2554              2564              2574              2583              2592
               AGCGGCTGAAC ACCGCCCACC GTGCTGCTGC TGCGCAG ACC GAC AAC CCA GGC CCG TGG
                                                        Thr Asp Asn Pro Gly Pro Trp
```

Fig. 5F

```
           2601           2610            2619           2628           2637           2646
TTC CTC CAC TGC CAC ATC GAC TTC CAC CTG GAG GCC GGC TTC GCC ATC GTC TGG
Phe Leu His Cys His Ile Asp Phe His Leu Glu Ala Gly Phe Ala Ile Val Trp 2655           2664           2673            2682                     2699
GGG GAG GAC ACT GCG GAC ACC GCG TCC GCG AAT CCC GTT CCT A     GTACGTCGTG
Gly Glu Asp Thr Ala Asp Thr Ala Ser Ala Asn Pro Val Pro Thr 2709       2719       2729              2739       2749       2759
CCTGCTGAGC TCTTTGTGCC CGAACAGGGT GCTGATCGTG CCTTCCTCCG TGCAG CG GCG TGG
                                                                Ala Trp 2768       2777       2786       2795       2804       2817
AGC GAT TTG TGC CCC ACT TAC GAT GCT TTG GAC TCG TCC GAC CTC TGATCGACAA
Ser Asp Leu Cys Pro Thr Tyr Asp Ala Leu Asp Ser Ser Asp Leu 2827       2837       2847       2857       2867       2877       2887
GGCATGAAGG CTGAAGCAGC TGCGGTCAAT TCTCGAACAC ACTTTACTCG AACATTCATT TTTCTTTGGC 2897       2907       2917
TCGGGATCGG AACAAATCAT GGGGGGGCCG GACCGTCT
```

Fig. 5G

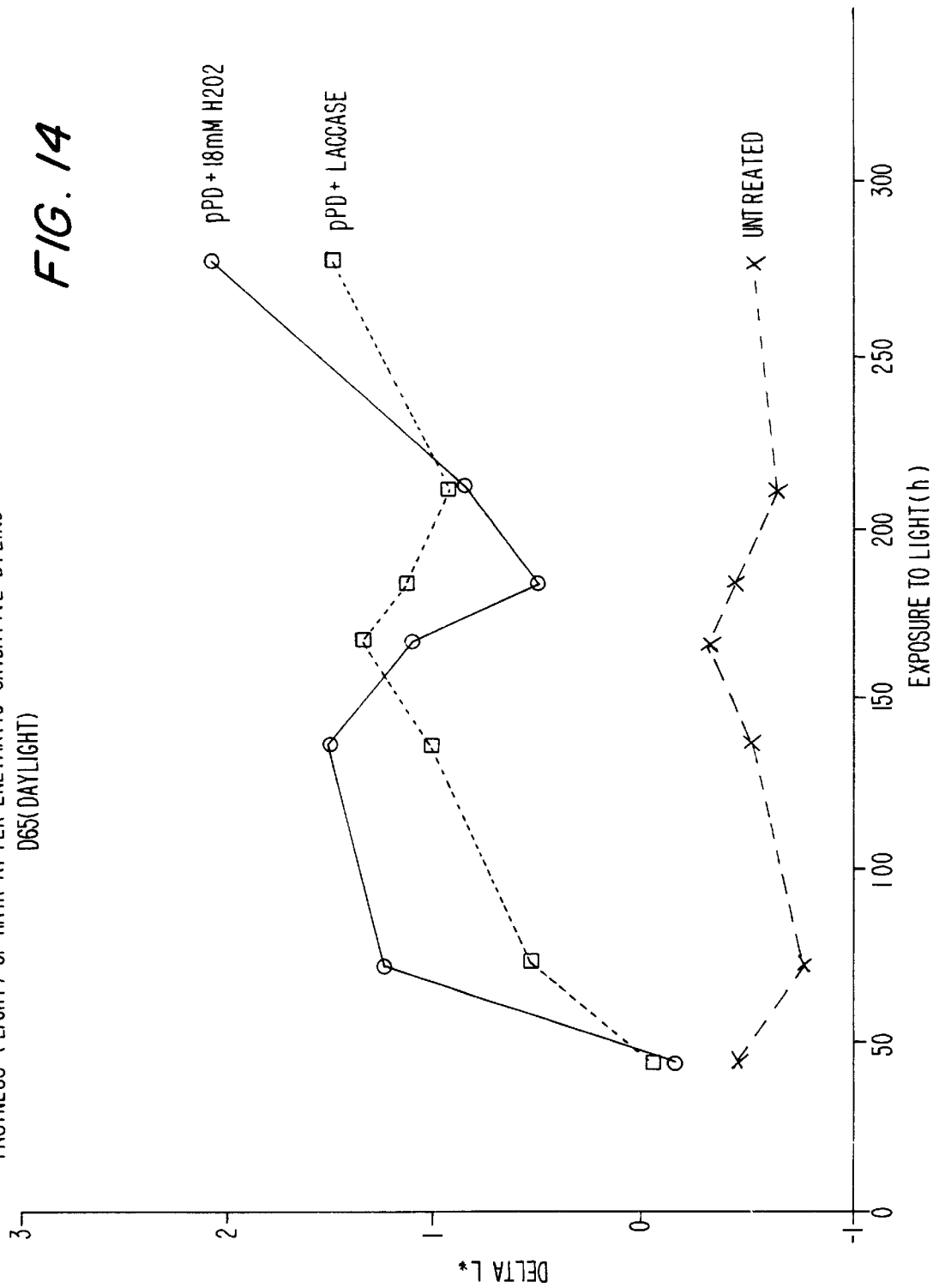

SEQUENCE LISTING ( 1 ) GENERAL INFORMATION:

( i i i ) NUMBER OF SEQUENCES: 10

( 2 ) INFORMATION FOR SEQ ID NO: 1:

( i ) SEQUENCE CHARACTERISTICS:
        ( A ) LENGTH: 2418 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Polyporus pinsitus ( i x ) FEATURE:
        ( A ) NAME/KEY: intron
        ( B ) LOCATION: 414..464

( i x ) FEATURE:
        ( A ) NAME/KEY: intron
        ( B ) LOCATION: 534..589

( i x ) FEATURE:
        ( A ) NAME/KEY: intron
        ( B ) LOCATION: 710..764

( i x ) FEATURE:
        ( A ) NAME/KEY: intron
        ( B ) LOCATION: 879..934

( i x ) FEATURE:
        ( A ) NAME/KEY: intron
        ( B ) LOCATION: 1001..1050

( i x ) FEATURE:
        ( A ) NAME/KEY: intron
        ( B ) LOCATION: 1147..1197

( i x ) FEATURE:
        ( A ) NAME/KEY: intron
        ( B ) LOCATION: 1354..1410

( i x ) FEATURE:
        ( A ) NAME/KEY: intron
        ( B ) LOCATION: 1609..1662

( i x ) FEATURE:
        ( A ) NAME/KEY: CDS
        ( B ) LOCATION: join (413..465, 533..590, 709..765, 878..935,
            1000..1051, 1146..1198, 1353..1411, 1608..1663)

( x i ) SEQUENCE DESCRIPTION: SEQ ID NO: 1:

```
AGATTTCTGA  CACCGGTGCA  ATCTTGACAC  TGTACCAACC  GGGCAAGTCT  CGTCCTTGGT           60

TCTCGGGGACT  GGCGCCGGT   CGCTACCCCT  TGGTCATTCA  CTCTACCAGA  GCGCTGGCTT          120

CGCCGAGGTA  TAAAGGATGT  TGCGCGACAC  CCTCAACACC  CCAACTCAAG  CCCCACTTGA          180

GCTTTTGCGA  GATCCTCCAC  ATACCACTCA  CTACTTTCAA  GTTCTTCAAC  ATG  TCG  AGG      239
                                                            Met  Ser  Arg
                                                             1

TTT  CAC  TCT  CTT  CTC  GCT  TTC  GTC  GTT  GCT  TCC  CTT  ACG  GCT  GTG  GCC   287
Phe  His  Ser  Leu  Leu  Ala  Phe  Val  Val  Ala  Ser  Leu  Thr  Ala  Val  Ala
      5                        10                      15

CAC  GCT  GGT  ATC  GGT  CCC  GTC  GCC  GAC  CTA  ACC  ATC  ACC  AAC  GCA  GCG   335
His  Ala  Gly  Ile  Gly  Pro  Val  Ala  Asp  Leu  Thr  Ile  Thr  Asn  Ala  Ala
 20                  25                      30                      35

GTC  AGC  CCC  GAC  GGG  TTT  TCT  CGC  CAG  GCC  GTC  GTC  GTG  AAC  GGC  GGC   383
Val  Ser  Pro  Asp  Gly  Phe  Ser  Arg  Gln  Ala  Val  Val  Val  Asn  Gly  Gly
                  35                      40                      45

ACC  CCT  GGC  CCT  CTC  ATC  ACG  GGT  AAC  ATG  GTTCGTCTCG  GCTCGCACTA         433
Thr  Pro  Gly  Pro  Leu  Ile  Thr  Gly  Asn  Met
             50                      55

GGGGGTTGTA  TCGTTCCTGA  CGTTGTTGGA  G  GGG  GAT  CGC  TTC  CAG  CTC  AAT  GTC  A  491
```

|  |  |  |  |  |  |  |  |  |  |  |  | Gly | Asp | Arg | Phe | Gln | Leu | Asn | Val | Ile |  |
|---|---|---|---|---|---|---|---|---|---|---|---|---|---|---|---|---|---|---|---|---|---|
|  |  |  |  |  |  |  |  |  |  |  |  |  |  |  | 60 |  |  |  |  | 65 |  |

```
GAC  AAC  CTT  ACC  AAC  CAC  ACG  ATG  GTG  AAG  AGC  ACG  AGT  ATT  GTGAGCTGCT          543
Asp  Asn  Leu  Thr  Asn  His  Thr  Met  Val  Lys  Ser  Thr  Ser  Ile
               70                       75

ATTTCTCCGG ACGGGGCTTC ATTGTGCTAA TAATCGTCGT GTGCAG CAC TGG CAC GGT                        601
                                                        80

TTC  TTC  CAG  AAG  GGT  ACC  AAC  TGG  GCC  GAC  GGT  CCC  GCC  TTC  ATC  AAC           649
Phe  Phe  Gln  Lys  Gly  Thr  Asn  Trp  Ala  Asp  Gly  Pro  Ala  Phe  Ile  Asn
     85                  90                  95

CAG  TGC  CCG  ATC  TCA  TCT  GGT  CAC  TCG  TTC  CTG  TAC  GAC  TTC  CAG  GTT           697
Gln  Cys  Pro  Ile  Ser  Ser  Gly  His  Ser  Phe  Leu  Tyr  Asp  Phe  Gln  Val
100                 105                 110                 115

CCT  GAC  CAG  GCT  GTAAGTACGG TCGTTATGGA GTATACTGCG CATTGCTAAA                           749
Pro  Asp  Gln  Ala

CCACATGGTG AACAG GGT  ACC  TTC  TGG  TAT  CAC  AGT  CAC  TTG  TCT  ACG  CAG              800
                Gly  Thr  Phe  Trp  Tyr  His  Ser  His  Leu  Ser  Thr  Gln
                120                 125                      130

TAC  TGT  GAT  GGT  TTG  AGG  GGT  CCG  TTC  GTT  GTT  TAC  GAC  CCG  AAT  GAC           848
Tyr  Cys  Asp  Gly  Leu  Arg  Gly  Pro  Phe  Val  Val  Tyr  Asp  Pro  Asn  Asp
          135                 140                      145

CCG  GCC  GCC  GAC  CTG  TAC  GAC  GTC  GAC  AAC  GTAAGGACGA ATTCGAACCG                   898
Pro  Ala  Ala  Asp  Leu  Tyr  Asp  Val  Asp  Asn
               150                 155

TAAATACTTG CTTACTGATA CTTCTCGATG AATTAG GAC  GAC  ACT  GTC  ATT                           949
                                        Asp  Asp  Thr  Val  Ile
                                                  160

ACC  CTT  GTG  GAT  TGG  TAC  CAC  GTC  GCC  GCG  AAG  CTG  GGC  CCC  GCA  TTC           997
Thr  Leu  Val  Asp  Trp  Tyr  His  Val  Ala  Ala  Lys  Leu  Gly  Pro  Ala  Phe
          165                 170                      175

CCT  GTAAGTCCAT GAGTATTCTG CTGTTGAATC TGTCTTAACT GTGCATATCA CTC                           1053
Pro                                                                Leu
                                                                   180

GGC  GCC  GAC  GCC  ACC  CTC  ATC  AAC  GGT  AAG  GGA  CGC  TCC  CCC  AGC  ACG           1101
Gly  Ala  Asp  Ala  Thr  Leu  Ile  Asn  Gly  Lys  Gly  Arg  Ser  Pro  Ser  Thr
               185                 190                      195

ACC  ACC  GCG  GAC  CTC  TCA  GTT  ATC  AGC  GTC  ACC  CCG  GGT  AAA  CGC                1146
Thr  Thr  Ala  Asp  Leu  Ser  Val  Ile  Ser  Val  Thr  Pro  Gly  Lys  Arg
               200                 205                      210

GTATGCTATA TCTTATCTTA TCTGATGGCA TTTCTCTGAG ACATTCTCCA G                                  1197

TAC  CGT  TTC  CGC  CTG  GTG  TCC  CTG  TCG  TGC  GAC  CCC  AAC  TAC  ACG  TTC           1245
Tyr  Arg  Phe  Arg  Leu  Val  Ser  Leu  Ser  Cys  Asp  Pro  Asn  Tyr  Thr  Phe
          215                 220                      225

AGC  ATC  GAT  GGT  CAC  AAC  ATG  ACG  ATC  ATC  GAG  ACC  GAC  TCA  ATC  AAC           1293
Ser  Ile  Asp  Gly  His  Asn  Met  Thr  Ile  Ile  Glu  Thr  Asp  Ser  Ile  Asn
          230                 235                      240

ACG  GCG  CCC  CTC  GTC  GTC  GAC  TCC  ATT  CAG  ATC  TTC  GCC  GCC  CAG  CGT           1341
Thr  Ala  Pro  Leu  Val  Val  Asp  Ser  Ile  Gln  Ile  Phe  Ala  Ala  Gln  Arg
245                 250                 255

TAC  TCC  TTC  GTG  GTAAGTTCGA TTCATCCTCT AACGTTGGTC GCTGTTAGTG                           1393
Tyr  Ser  Phe  Val
260

ATCGTATGGT CATGTAG CTC  GAG  GCC  AAC  CAG  GCC  GTC  GAC  AAC  TAC  TGG                 1443
                   Leu  Glu  Ala  Asn  Gln  Ala  Val  Asp  Asn  Tyr  Trp
                        265                      270

ATT  CGC  GCC  AAC  CCG  AAC  TTC  GGT  AAC  GTC  GGG  TTC  ACC  GGC  GGC  ATT           1491
Ile  Arg  Ala  Asn  Pro  Asn  Phe  Gly  Asn  Val  Gly  Phe  Thr  Gly  Gly  Ile
275                 280                 285                      290
```

```
AAC  TCG  GCT  ATC  CTC  CGC  TAC  GAT  GGT  GCC  GCT  GCC  GTG  GAG  CCC  ACC      1539
Asn  Ser  Ala  Ile  Leu  Arg  Tyr  Asp  Gly  Ala  Ala  Ala  Val  Glu  Pro  Thr
                         295                 300                      305

ACA  ACG  CAA  ACC  ACG  TCG  ACT  GCG  CCG  CTC  AAC  GAG  GTC  AAC  CTG  CAC      1587
Thr  Thr  Gln  Thr  Thr  Ser  Thr  Ala  Pro  Leu  Asn  Glu  Val  Asn  Leu  His
               310                      315                           320

CCG  CTG  GTT  ACC  ACC  GCT  GTG  GTATGTAATA  TTGTCGGTAA  TGTAATACAT             1638
Pro  Leu  Val  Thr  Thr  Ala  Val
               325

TGTTGCTGAC  CTCGACCCCC  ACAG  CCT  GGC  TCG  CCC  GTC  GCT  GGT  GGT  GTC          1689
                              Pro  Gly  Ser  Pro  Val  Ala  Gly  Gly  Val
                              330                      335

GAC  CTG  GCC  ATC  AAC  ATG  GCG  TTC  AAC  TTC  AAC  GGC  ACC  AAC  TTC  TTC      1737
Asp  Leu  Ala  Ile  Asn  Met  Ala  Phe  Asn  Phe  Asn  Gly  Thr  Asn  Phe  Phe
          340                 345                      350

ATC  AAC  GGC  ACG  TCT  TTC  ACG  CCC  CCG  ACC  GTG  CCT  GTC  CTG  CTC  CAG      1785
Ile  Asn  Gly  Thr  Ser  Phe  Thr  Pro  Pro  Thr  Val  Pro  Val  Leu  Leu  Gln
355                      360                      365                      370

ATC  ATC  AGC  GGC  GCG  CAG  AAC  GCG  CAG  GAC  CTC  CTG  CCC  TCC  GGT  AGC      1833
Ile  Ile  Ser  Gly  Ala  Gln  Asn  Ala  Gln  Asp  Leu  Leu  Pro  Ser  Gly  Ser
                    375                      380                      385

GTC  TAC  TCG  CTT  CCC  TCG  AAC  GCC  GAC  ATC  GAG  ATC  TCC  TTC  CCC  GCC      1881
Val  Tyr  Ser  Leu  Pro  Ser  Asn  Ala  Asp  Ile  Glu  Ile  Ser  Phe  Pro  Ala
               390                      395                      400

ACC  GCC  GCC  GCC  CCC  GGT  GCG  CCC  CAC  CCC  TTC  CAC  TTG  CAC  GGG  CAC      1929
Thr  Ala  Ala  Ala  Pro  Gly  Ala  Pro  His  Pro  Phe  His  Leu  His  Gly  His
          405                      410                      415

GCG  TTC  GCG  GTC  GTC  CGC  AGC  GCC  GGC  AGC  ACG  GTT  TAC  AAC  TAC  GAC      1977
Ala  Phe  Ala  Val  Val  Arg  Ser  Ala  Gly  Ser  Thr  Val  Tyr  Asn  Tyr  Asp
     420                      425                      430

AAC  CCC  ATC  TTC  CGC  GAC  GTC  GTC  AGC  ACG  GGG  ACG  CCT  GCG  GCC  GGT      2025
Asn  Pro  Ile  Phe  Arg  Asp  Val  Val  Ser  Thr  Gly  Thr  Pro  Ala  Ala  Gly
435                      440                      445                      450

GAC  AAC  GTC  ACC  ATC  CGC  TTC  CGC  ACC  GAC  AAC  CCC  GGC  CCG  TGG  TTC      2073
Asp  Asn  Val  Thr  Ile  Arg  Phe  Arg  Thr  Asp  Asn  Pro  Gly  Pro  Trp  Phe
                    455                      460                      465

CTC  CAC  TGC  CAC  ATC  GAC  TTC  CAC  CTC  GAG  GCC  GGC  TTC  GCC  GTC  GTG      2121
Leu  His  Cys  His  Ile  Asp  Phe  His  Leu  Glu  Ala  Gly  Phe  Ala  Val  Val
               470                      475                      480

TTC  GCG  GAG  GAC  ATC  CCC  GAC  GTC  GCG  TCG  GCG  AAC  CCC  GTC  CCC  CAG      2169
Phe  Ala  Glu  Asp  Ile  Pro  Asp  Val  Ala  Ser  Ala  Asn  Pro  Val  Pro  Gln
          485                      490                      495

GCG  TGG  TCC  GAC  CTC  TGT  CCG  ACC  TAC  GAC  GCG  CTC  GAC  CCG  AGC  GAC      2217
Ala  Trp  Ser  Asp  Leu  Cys  Pro  Thr  Tyr  Asp  Ala  Leu  Asp  Pro  Ser  Asp
500                      505                      510

CAG  TAAATGGCTT  GCGCCGGTCG  ATGATAGGAT  ATGGACGGTG  AGTTCGCACT                    2270
Gln
515

TGCAATACGG  ACTCTCGCCT  CATTATGGTT  ACACACTCGC  TCTGGATCTC  TCGCCTGTCG              2330

ACAGAACAAA  CTTGTATAAT  TCGCTTAATG  GTTGAAACAA  ATGGAATATT  GGGGTACTAT              2390

GCACGCATCT  CGCTGGGTGA  GCTTTCGT                                                    2418

( 2 ) INFORMATION FOR SEQ ID NO: 2:

( i ) SEQUENCE CHARACTERISTICS:
                ( A ) LENGTH: 520 amino acids
                ( B ) TYPE: amino acid
                ( C ) STRANDEDNESS: single
                ( D ) TOPOLOGY: linear
```

( i i ) MOLECULE TYPE: protein ( v i ) ORIGINAL SOURCE:
    ( A ) ORGANISM: Polyporus pinsitus ( x i ) SEQUENCE DESCRIPTION: SEQ ID NO: 2:

```
Met Ser Arg Phe His Ser Leu Leu Ala Phe Val Val Ala Ser Leu Thr
 1               5                  10                  15

Ala Val Ala His Ala Gly Ile Gly Pro Val Ala Asp Leu Thr Ile Thr
            20                  25                  30

Asn Ala Ala Val Ser Pro Asp Gly Phe Ser Arg Gln Ala Val Val Val
            35                  40                  45

Asn Gly Gly Thr Pro Gly Pro Leu Ile Thr Gly Asn Met Gly Asp Arg
50                      55                  60

Phe Gln Leu Asn Val Ile Asp Asn Leu Thr Asn His Thr Met Val Lys
65                      70                  75                  80

Ser Thr Ser Ile His Trp His Gly Phe Phe Gln Lys Gly Thr Asn Trp
                85                  90                  95

Ala Asp Gly Pro Ala Phe Ile Asn Gln Cys Pro Ile Ser Ser Gly His
            100                 105                 110

Ser Phe Leu Tyr Asp Phe Gln Val Pro Asp Gln Ala Gly Thr Phe Trp
        115                 120                 125

Tyr His Ser His Leu Ser Thr Gln Tyr Cys Asp Gly Leu Arg Gly Pro
    130                 135                 140

Phe Val Val Tyr Asp Pro Asn Asp Pro Ala Ala Asp Leu Tyr Asp Val
145                 150                 155                 160

Asp Asn Asp Asp Thr Val Ile Thr Leu Val Asp Trp Tyr His Val Ala
                165                 170                 175

Ala Lys Leu Gly Pro Ala Phe Pro Leu Gly Ala Asp Ala Thr Leu Ile
            180                 185                 190

Asn Gly Lys Gly Arg Ser Pro Ser Thr Thr Thr Ala Asp Leu Ser Val
        195                 200                 205

Ile Ser Val Thr Pro Gly Lys Arg Tyr Arg Phe Arg Leu Val Ser Leu
    210                 215                 220

Ser Cys Asp Pro Asn Tyr Thr Phe Ser Ile Asp Gly His Asn Met Thr
225                 230                 235                 240

Ile Ile Glu Thr Asp Ser Ile Asn Thr Ala Pro Leu Val Val Asp Ser
                245                 250                 255

Ile Gln Ile Phe Ala Ala Gln Arg Tyr Ser Phe Val Leu Glu Ala Asn
            260                 265                 270

Gln Ala Val Asp Asn Tyr Trp Ile Arg Ala Asn Pro Asn Phe Gly Asn
        275                 280                 285

Val Gly Phe Thr Gly Gly Ile Asn Ser Ala Ile Leu Arg Tyr Asp Gly
    290                 295                 300

Ala Ala Ala Val Glu Pro Thr Thr Gln Thr Thr Ser Thr Ala Pro
305                 310                 315                 320

Leu Asn Glu Val Asn Leu His Pro Leu Val Thr Thr Ala Val Pro Gly
                325                 330                 335

Ser Pro Val Ala Gly Gly Val Asp Leu Ala Ile Asn Met Ala Phe Asn
            340                 345                 350

Phe Asn Gly Thr Asn Phe Phe Ile Asn Gly Thr Ser Phe Thr Pro Pro
        355                 360                 365

Thr Val Pro Val Leu Leu Gln Ile Ile Ser Gly Ala Gln Asn Ala Gln
    370                 375                 380

Asp Leu Leu Pro Ser Gly Ser Val Tyr Ser Leu Pro Ser Asn Ala Asp
```

```
385                         390                         395                         400
Ile Glu Ile Ser Phe Pro Ala Thr Ala Ala Ala Pro Gly Ala Pro His
                405                         410                         415

Pro Phe His Leu His Gly His Ala Phe Ala Val Val Arg Ser Ala Gly
            420                         425                         430

Ser Thr Val Tyr Asn Tyr Asp Asn Pro Ile Phe Arg Asp Val Val Ser
            435                         440                         445

Thr Gly Thr Pro Ala Ala Gly Asp Asn Val Thr Ile Arg Phe Arg Thr
        450                         455                         460

Asp Asn Pro Gly Pro Trp Phe Leu His Cys His Ile Asp Phe His Leu
465                         470                         475                         480

Glu Ala Gly Phe Ala Val Val Phe Ala Glu Asp Ile Pro Asp Val Ala
                485                         490                         495

Ser Ala Asn Pro Val Pro Gln Ala Trp Ser Asp Leu Cys Pro Thr Tyr
            500                         505                         510

Asp Ala Leu Asp Pro Ser Asp Gln
            515                 520
```

( 2 ) INFORMATION FOR SEQ ID NO:3:

( i ) SEQUENCE CHARACTERISTICS:
        ( A ) LENGTH: 2880 base pairs
        ( B ) TYPE: nucleic acid
        ( C ) STRANDEDNESS: single
        ( D ) TOPOLOGY: linear ( i x ) FEATURE:
        ( A ) NAME/KEY: intron
        ( B ) LOCATION: 544..592

( i x ) FEATURE:
        ( A ) NAME/KEY: intron
        ( B ) LOCATION: 837..899

( i x ) FEATURE:
        ( A ) NAME/KEY: intron
        ( B ) LOCATION: 1014..1066

( i x ) FEATURE:
        ( A ) NAME/KEY: intron
        ( B ) LOCATION: 1133..1187

( i x ) FEATURE:
        ( A ) NAME/KEY: intron
        ( B ) LOCATION: 1284..1342

( i x ) FEATURE:
        ( A ) NAME/KEY: intron
        ( B ) LOCATION: 1752..1815

( i x ) FEATURE:
        ( A ) NAME/KEY: intron
        ( B ) LOCATION: 1873..1928

( i x ) FEATURE:
        ( A ) NAME/KEY: intron
        ( B ) LOCATION: 2136..2195

( i x ) FEATURE:
        ( A ) NAME/KEY: CDS
        ( B ) LOCATION: join(364..543, 593..661, 716..835, 900..1013,
            1067..1132, 1188..1283, 1343..1498, 1554..1751,
            1816..1872, 1929..2135, 2196..2489)

( i x ) FEATURE:
        ( A ) NAME/KEY: intron
        ( B ) LOCATION: 662..715

( i x ) FEATURE:
        ( A ) NAME/KEY: intron
        ( B ) LOCATION: 1499..1553

( x i ) SEQUENCE DESCRIPTION: SEQ ID NO:3:

| | | | | | | |
|---|---|---|---|---|---|---|
| GCGGCGCACA | AACCGTGGGA | GCCAACACAC | TCCCGTCCAC | TCTCACACTG | GCCAGATTCG | 60 |
| CGCGACCGCC | GCCTTTCAGG | CCCAAACAGA | TCTGGCAGGT | TTCGATGGCG | CACGCCGCCG | 120 |
| TGCCTGCCGG | ATTCAATTGT | GCGCCAGTCG | GCATCCGGA | TGGCTCTACC | AGCGCGGTTG | 180 |
| ACTGGAAGAG | AACACCGAGG | TCATGCATTC | TGGCCAAGTG | CGGCCAAAGG | ACCGCTCGCT | 240 |
| GGTGCGGATA | CTTAAAGGGC | GGCGCGGGA | GGCCTGTCTA | CCAAGCTCAA | GCTCGCCTTG | 300 |
| GGTTCCCAGT | CTCCGCCACC | CTCCTCTTCC | CCCACACAGT | CGCTCCATAG | CACCGTCGGC | 360 |

```
GCC ATG GGT CTG CAG CGA TTC AGC TTC TTC GTC ACC CTC GCG CTC GTC                408
    Met Gly Leu Gln Arg Phe Ser Phe Phe Val Thr Leu Ala Leu Val
     1               5                  10                  15

GCT CGC TCT CTT GCA GCC ATC GGG CCG GTG GCG AGC CTC GTC GTC GCG                456
Ala Arg Ser Leu Ala Ala Ile Gly Pro Val Ala Ser Leu Val Val Ala
             20                  25                  30

AAC GCC CCC GTC TCG CCC GAC GGC TTC CTT CGG GAT GCC ATC GTG GTC                504
Asn Ala Pro Val Ser Pro Asp Gly Phe Leu Arg Asp Ala Ile Val Val
                 35                  40                  45

AAC GGC GTG GTC CCT TCC CCG CTC ATC ACC GGG AAG AAG GTCGGCGTGT                 553
Asn Gly Val Val Pro Ser Pro Leu Ile Thr Gly Lys Lys
     50                  55                  60

TCGTCGTCGT CCTACTCCTT TGCTGACAGC GATCTACAG GGA GAC CGC TTC CAG                 607
                                                Gly Asp Arg Phe Gln
                                                            65

CTC AAC GTC GTC GAC ACC TTG ACC AAC CAC AGC ATG CTC AAG TCC ACT                655
Leu Asn Val Val Asp Thr Leu Thr Asn His Ser Met Leu Lys Ser Thr
             70                  75                  80

AGT ATC GTAAGTGTGA CGATCCGAAT GTGACATCAA TCGGGGCTAA TTAACCGCGC                 711
Ser Ile

ACAG CAC TGG CAC GGC TTC TTC CAG GCA GGC ACC AAC TGG GCA GAA GGA              760
     His Trp His Gly Phe Phe Gln Ala Gly Thr Asn Trp Ala Glu Gly
              85                  90                  95

CCC GCG TTC GTC AAC CAG TGC CCT ATT GCT TCC GGG CAT TCA TTC CTG                808
Pro Ala Phe Val Asn Gln Cys Pro Ile Ala Ser Gly His Ser Phe Leu
    100                 105                 110

TAC GAC TTC CAT GTG CCC GAC CAG GCA GTAAGCAGGA TTTTCTGGGG                      855
Tyr Asp Phe His Val Pro Asp Gln Ala
115                 120

TCCCCGTGTG ATGCAATGTT CTCATGCTCC GACGTGATCG ACAG GGG ACG TTC TGG              911
                                                 Gly Thr Phe Trp
                                                        125

TAC CAC AGT CAT CTG TCT ACG CAG TAC TGT GAC GGG CTG CGG GGG CCG                959
Tyr His Ser His Leu Ser Thr Gln Tyr Cys Asp Gly Leu Arg Gly Pro
        130                 135                 140

TTC GTC GTG TAC GAC CCC AAG GAC CCG CAC GCC AGC CGT TAC GAT GTT               1007
Phe Val Val Tyr Asp Pro Lys Asp Pro His Ala Ser Arg Tyr Asp Val
145                 150                 155

GAC AAT GTACGTGCGC CACGGAGTAT ATCACACAGC ATGCGTTGAC GTCGGGCCAA                1063
Asp Asn
160

CAG GAG AGC ACG GTC ATC ACG TTG ACC GAC TGG TAC CAC ACC GCT GCC               1111
    Glu Ser Thr Val Ile Thr Leu Thr Asp Trp Tyr His Thr Ala Ala
                165                 170                 175

CGG CTC GGT CCC AAG TTC CCA GTAAGCTCGC AATGGCTTAG TGTTCACAGG                  1162
Arg Leu Gly Pro Lys Phe Pro
            180

TTCTTTGCTT ATGTTGCTTC GATAG CTC GGC GCG GAC GCC ACG CTC ATC AAC               1214
                          Leu Gly Ala Asp Ala Thr Leu Ile Asn
```

|  |  |
|---|---|
| GGT CTG GGG CGG TCG GCC TCG ACT CCC ACC GCT GCG CTT GCC GTG ATC<br>Gly Leu Gly Arg Ser Ala Ser Thr Pro Thr Ala Ala Leu Ala Val Ile<br>195                              200                            205 | 1262 |
| AAC GTC CAG CAC GGA AAG CGC GTGAGCATTC TCTTGTATGC CATTTCAATG<br>Asn Val Gln His Gly Lys Arg<br>210                             215 | 1313 |
| CTTTGTGCTG ACCTATCGGA ACCGCGCAG TAC CGC TTC CGT CTC GTT TCG ATC<br>                                                      Tyr Arg Phe Arg Leu Val Ser Ile<br>                                                                  220 | 1366 |
| TCG TGT GAC CCG AAC TAC ACG TTC AGC ATC GAC GGG CAC AAC CTG ACC<br>Ser Cys Asp Pro Asn Tyr Thr Phe Ser Ile Asp Gly His Asn Leu Thr<br>225                            230                            235 | 1414 |
| GTC ATC GAG GTC GAC GGC ATC AAT AGC CAG CCT CTC CTT GTC GAC TCT<br>Val Ile Glu Val Asp Gly Ile Asn Ser Gln Pro Leu Leu Val Asp Ser<br>240                            245                        250                        255 | 1462 |
| ATC CAG ATC TTC GCC GCA CAG CGC TAC TCC TTC GTG GTAAGTCCTG<br>Ile Gln Ile Phe Ala Ala Gln Arg Tyr Ser Phe Val<br>                260                        265 | 1508 |
| GCTTGTCGAT GCTCCAAAGT GGCCTCACTC ATATACTTTC GTTAG TTG AAT GCG<br>                                                                    Leu Asn Ala<br>                                                                     270 | 1562 |
| AAT CAA ACG GTG GGC AAC TAC TGG GTT CGT GCG AAC CCG AAC TTC GGA<br>Asn Gln Thr Val Gly Asn Tyr Trp Val Arg Ala Asn Pro Asn Phe Gly<br>                275                            280                        285 | 1610 |
| ACG GTT GGG TTC GCC GGG GGG ATC AAC TCC GCC ATC TTG CGC TAC CAG<br>Thr Val Gly Phe Ala Gly Gly Ile Asn Ser Ala Ile Leu Arg Tyr Gln<br>                290                            295                        300 | 1658 |
| GGC GCA CCG GTC GCC GAG CCT ACC ACG ACC CAG ACG CCG TCG GTG ATC<br>Gly Ala Pro Val Ala Glu Pro Thr Thr Thr Gln Thr Pro Ser Val Ile<br>                305                            310                        315 | 1706 |
| CCG CTC ATC GAG ACG AAC TTG CAC CCG CTC GCG CGC ATG CCA GTG<br>Pro Leu Ile Glu Thr Asn Leu His Pro Leu Ala Arg Met Pro Val<br>320                            325                        330 | 1751 |
| GTATGTCTCT TTTTCTGATC ATCTGAGTTG CCCGTTGTTG ACCGCATTAT GTGTTACTAT | 1811 |
| CTAG CCT GGC AGC CCG ACA CCC GGG GGC GTC GAC AAG GCG CTC AAC CTC<br>     Pro Gly Ser Pro Thr Pro Gly Gly Val Asp Lys Ala Leu Asn Leu<br>        335                            340                        345 | 1860 |
| GCG TTT AAC TTC GTAAGTATCT CTACTACTTA GGCTGGAGGC TCGTCGCTGA<br>Ala Phe Asn Phe<br>350 | 1912 |
| TCATACGGTG CTTCAG AAC GGC ACC AAC TTC TTC ATC AAC AAC GCG ACT<br>                        Asn Gly Thr Asn Phe Phe Ile Asn Asn Ala Thr<br>                                355                              360 | 1961 |
| TTC ACG CCG CCG ACC GTC CCG GTA CTC CTC CAG ATT CTG AGC GGT GCG<br>Phe Thr Pro Pro Thr Val Pro Val Leu Leu Gln Ile Leu Ser Gly Ala<br>365                            370                        375 | 2009 |
| CAG ACC GCA CAA GAC CTG CTC CCC GCA GGC TCT GTC TAC CCG CTC CCG<br>Gln Thr Ala Gln Asp Leu Leu Pro Ala Gly Ser Val Tyr Pro Leu Pro<br>380                            385                        390                        395 | 2057 |
| GCC CAC TCC ACC ATC GAG ATC ACG CTG CCC GCG ACC GCC TTG GCC CCG<br>Ala His Ser Thr Ile Glu Ile Thr Leu Pro Ala Thr Ala Leu Ala Pro<br>                400                            405                        410 | 2105 |
| GGT GCA CCG CAC CCC TTC CAC CTG CAC GGT GTATGTTCCC CTGCCTTCCC<br>Gly Ala Pro His Pro Phe His Leu His Gly<br>                415                        420 | 2155 |
| TTCTTATCCC CGAACCAGTG CTCACGTCCG TCCCATCTAG CAC GCC TTC GCG GTC<br>                                                                     His Ala Phe Ala Val<br>                                                                       425 | 2210 |

```
GTT  CGC  AGC  GCG  GGG  AGC  ACC  ACG  TAT  AAC  TAC  AAC  GAC  CCG  ATC  TTC        2258
Val  Arg  Ser  Ala  Gly  Ser  Thr  Thr  Tyr  Asn  Tyr  Asn  Asp  Pro  Ile  Phe
               430                 435                      440

CGC  GAC  GTC  GTG  AGC  ACG  GGC  ACG  CCC  GCC  GCG  GGC  GAC  AAC  GTC  ACG        2306
Arg  Asp  Val  Val  Ser  Thr  Gly  Thr  Pro  Ala  Ala  Gly  Asp  Asn  Val  Thr
               445                 450                      455

ATC  CGC  TTC  CAG  ACG  GAC  AAC  CCC  GGG  CCG  TGG  TTC  CTC  CAC  TGC  CAC        2354
Ile  Arg  Phe  Gln  Thr  Asp  Asn  Pro  Gly  Pro  Trp  Phe  Leu  His  Cys  His
     460                      465                      470

ATC  GAC  TTC  CAC  CTC  GAC  GCA  GGC  TTC  GCG  ATC  GTG  TTC  GCA  GAG  GAC        2402
Ile  Asp  Phe  His  Leu  Asp  Ala  Gly  Phe  Ala  Ile  Val  Phe  Ala  Glu  Asp
475                      480                      485                      490

GTT  GCG  GAC  GTG  AAG  GCG  GCG  AAC  CCG  GTT  CCG  AAG  GCG  TGG  TCG  GAC        2450
Val  Ala  Asp  Val  Lys  Ala  Ala  Asn  Pro  Val  Pro  Lys  Ala  Trp  Ser  Asp
               495                 500                      505

CTG  TGC  CCG  ATC  TAC  GAC  GGG  CTG  AGC  GAG  GCT  AAC  CAG  TGAGCGGAGG          2499
Leu  Cys  Pro  Ile  Tyr  Asp  Gly  Leu  Ser  Glu  Ala  Asn  Gln
               510                 515

GCGTGGTGTT  GAGCGTAAAG  CTCGGGCGTC  GACCTGGGGG  GTTGAAGGTG  TTCTGATTGA                2559

AATGGTCTTT  GGGTTTATTT  GTTGTTATTC  TAACTCGGTT  CTCTACGCAA  GGACCGAGGA                2619

TTGTATAGGA  TGAAGTAACT  TCCCTAATGT  ATTATGATAT  CAATTGACGG  AGGCATGGAC                2679

TGCGAAGTGT  GTACAATGTG  GTAGTGGTCT  AGGCCTTGGA  GACAAGCTGT  GGATTTTTCT                2739

TGGGGGATGA  AGAGGCGTGA  AGGCTGAGAG  CTATGCTATG  CCTAGTGACG  TGGTTATAGT                2799

AAATGTCCAT  TACATTGACC  AAGAACGACA  AGAACCATAA  GCTTGCTGAG  GATAGATGGG                2859

GGCGCGTCCG  CGAACGACTT  G                                                            2880
```

( 2 ) INFORMATION FOR SEQ ID NO:4:

( i ) SEQUENCE CHARACTERISTICS:
        ( A ) LENGTH: 519 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Gly  Leu  Gln  Arg  Phe  Ser  Phe  Phe  Val  Thr  Leu  Ala  Leu  Val  Ala
 1                  5                      10                      15

Arg  Ser  Leu  Ala  Ala  Ile  Gly  Pro  Val  Ala  Ser  Leu  Val  Val  Ala  Asn
               20                      25                      30

Ala  Pro  Val  Ser  Pro  Asp  Gly  Phe  Leu  Arg  Asp  Ala  Ile  Val  Val  Asn
               35                      40                      45

Gly  Val  Val  Pro  Ser  Pro  Leu  Ile  Thr  Gly  Lys  Lys  Gly  Asp  Arg  Phe
     50                      55                      60

Gln  Leu  Asn  Val  Val  Asp  Thr  Leu  Thr  Asn  His  Ser  Met  Leu  Lys  Ser
 65                      70                      75                      80

Thr  Ser  Ile  His  Trp  His  Gly  Phe  Phe  Gln  Ala  Gly  Thr  Asn  Trp  Ala
                    85                      90                      95

Glu  Gly  Pro  Ala  Phe  Val  Asn  Gln  Cys  Pro  Ile  Ala  Ser  Gly  His  Ser
               100                     105                     110

Phe  Leu  Tyr  Asp  Phe  His  Val  Pro  Asp  Gln  Ala  Gly  Thr  Phe  Trp  Tyr
               115                     120                     125

His  Ser  His  Leu  Ser  Thr  Gln  Tyr  Cys  Asp  Gly  Leu  Arg  Gly  Pro  Phe
               130                     135                     140

Val  Val  Tyr  Asp  Pro  Lys  Asp  Pro  His  Ala  Ser  Arg  Tyr  Asp  Val  Asp
145                      150                     155                     160
```

| | | | | | | | | | | | | | | |
|---|---|---|---|---|---|---|---|---|---|---|---|---|---|---|
| Asn | Glu | Ser | Thr | Val 165 | Ile | Thr | Leu | Thr | Asp 170 | Trp | Tyr | His | Thr | Ala 175 | Ala |
| Arg | Leu | Gly | Pro 180 | Lys | Phe | Pro | Leu | Gly 185 | Ala | Asp | Ala | Thr | Leu 190 | Ile | Asn |
| Gly | Leu | Gly 195 | Arg | Ser | Ala | Ser | Thr 200 | Pro | Thr | Ala | Ala | Leu 205 | Ala | Val | Ile |
| Asn | Val 210 | Gln | His | Gly | Lys | Arg 215 | Tyr | Arg | Phe | Arg | Leu 220 | Val | Ser | Ile | Ser |
| Cys 225 | Asp | Pro | Asn | Tyr | Thr 230 | Phe | Ser | Ile | Asp | Gly 235 | His | Asn | Leu | Thr | Val 240 |
| Ile | Glu | Val | Asp | Gly 245 | Ile | Asn | Ser | Gln | Pro 250 | Leu | Leu | Val | Asp | Ser 255 | Ile |
| Gln | Ile | Phe | Ala 260 | Ala | Gln | Arg | Tyr | Ser 265 | Phe | Val | Leu | Asn | Ala 270 | Asn | Gln |
| Thr | Val | Gly 275 | Asn | Tyr | Trp | Val | Arg 280 | Ala | Asn | Pro | Asn | Phe 285 | Gly | Thr | Val |
| Gly | Phe 290 | Ala | Gly | Gly | Ile | Asn 295 | Ser | Ala | Ile | Leu | Arg 300 | Tyr | Gln | Gly | Ala |
| Pro 305 | Val | Ala | Glu | Pro | Thr 310 | Thr | Thr | Gln | Thr | Pro 315 | Ser | Val | Ile | Pro | Leu 320 |
| Ile | Glu | Thr | Asn | Leu 325 | His | Pro | Leu | Ala | Arg 330 | Met | Pro | Val | Pro | Gly 335 | Ser |
| Pro | Thr | Pro | Gly 340 | Gly | Val | Asp | Lys | Ala 345 | Leu | Asn | Leu | Ala | Phe 350 | Asn | Phe |
| Asn | Gly | Thr 355 | Asn | Phe | Phe | Ile | Asn 360 | Asn | Ala | Thr | Phe | Thr 365 | Pro | Pro | Thr |
| Val | Pro 370 | Val | Leu | Leu | Gln | Ile 375 | Leu | Ser | Gly | Ala | Gln 380 | Thr | Ala | Gln | Asp |
| Leu 385 | Leu | Pro | Ala | Gly | Ser 390 | Val | Tyr | Pro | Leu | Pro 395 | Ala | His | Ser | Thr | Ile 400 |
| Glu | Ile | Thr | Leu | Pro 405 | Ala | Thr | Ala | Leu | Ala 410 | Pro | Gly | Ala | Pro | His 415 | Pro |
| Phe | His | Leu | His 420 | Gly | His | Ala | Phe | Ala 425 | Val | Val | Arg | Ser | Ala 430 | Gly | Ser |
| Thr | Thr | Tyr 435 | Asn | Tyr | Asn | Asp | Pro 440 | Ile | Phe | Arg | Asp | Val 445 | Val | Ser | Thr |
| Gly | Thr 450 | Pro | Ala | Ala | Gly | Asp 455 | Asn | Val | Thr | Ile | Arg 460 | Phe | Gln | Thr | Asp |
| Asn 465 | Pro | Gly | Pro | Trp | Phe 470 | Leu | His | Cys | His | Ile 475 | Asp | Phe | His | Leu | Asp 480 |
| Ala | Gly | Phe | Ala | Ile 485 | Val | Phe | Ala | Glu | Asp 490 | Val | Ala | Asp | Val | Lys 495 | Ala |
| Ala | Asn | Pro | Val 500 | Pro | Lys | Ala | Trp | Ser 505 | Asp | Leu | Cys | Pro | Ile 510 | Tyr | Asp |
| Gly | Leu | Ser 515 | Glu | Ala | Asn | Gln | | | | | | | | | |

( 2 ) INFORMATION FOR SEQ ID NO: 5:

( i ) SEQUENCE CHARACTERISTICS:
        ( A ) LENGTH: 3102 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
  ( A ) ORGANISM: Polyporus pinsitus ( i x ) FEATURE:
  ( A ) NAME/KEY: intron
  ( B ) LOCATION: 666..720

( i x ) FEATURE:
  ( A ) NAME/KEY: intron
  ( B ) LOCATION: 790..845

( i x ) FEATURE:
  ( A ) NAME/KEY: intron
  ( B ) LOCATION: 1125..1182

( i x ) FEATURE:
  ( A ) NAME/KEY: intron
  ( B ) LOCATION: 1390..1450

( i x ) FEATURE:
  ( A ) NAME/KEY: intron
  ( B ) LOCATION: 1607..1661

( i x ) FEATURE:
  ( A ) NAME/KEY: intron
  ( B ) LOCATION: 1863..1918

( i x ) FEATURE:
  ( A ) NAME/KEY: intron
  ( B ) LOCATION: 1976..2025

( i x ) FEATURE:
  ( A ) NAME/KEY: intron
  ( B ) LOCATION: 2227..2285

( i x ) FEATURE:
  ( A ) NAME/KEY: intron
  ( B ) LOCATION: 2403..2458

( i x ) FEATURE:
  ( A ) NAME/KEY: intron
  ( B ) LOCATION: 2576..2627

( i x ) FEATURE:
  ( A ) NAME/KEY: CDS
  ( B ) LOCATION: join (665..721, 789..846, 1124..1183, 1389..1451
       1606..1662, 1862..1919, 1975..2026, 2226..2286, 2402..245
       2575..2628).

( x i ) SEQUENCE DESCRIPTION: SEQ ID NO: 5:

```
TTTCCCGACT AAACCAATCT CAGNCCGCTT CCTCCTAGGG AACCGAGCGA TGTGGCGGCC        60

CTCTCTATCC AAGCTGTCCA TAAGAAGACG TTCAAATGCC GCAGCAAGCG AGGAAATAAG       120

CATCTAACAG TGTTTTTCCC ATAGTCGCAT TTGCGCCGCC TGTCGGACCG ACGCCCCTAG       180

AGCGCTTTGG GAAACGTCGC AAGTGGCGGG TGTTATTCGT GTAGACGAGA CGGTATTTGT       240

CTCATCATTC CCGTGCTTCA GGTTGACACA GCCCAAAGGT CTATGTACGG CCCTTCACAT       300

TCCCTGACAC ATTGACGCAA CCCTCGGTGC GCCTCCGACA GTGCCTCGGT TGTAGTATCG       360

GGACGCCCTA GGATGCAAGA TTGGAAGTCA CCAAGGCCCG AAGGGTATAA AATACCGAGA       420

GGTCCTACCA CTTCTGCATC TCCAGTCGCA GAGTTCCTCT CCCTTGCCAG CCACAGCTCG       480

AG ATG TCC TTC TCT AGC CTT CGC CGT GCC TTG GTC TTC CTG GGT GCT          527
   Met Ser Phe Ser Ser Leu Arg Arg Ala Leu Val Phe Leu Gly Ala
   1             5                  10                      15

TGC AGC AGT GCG CTG GCC TCC ATC GGC CCA GTC ACT GAG CTC GAC ATC         575
Cys Ser Ser Ala Leu Ala Ser Ile Gly Pro Val Thr Glu Leu Asp Ile
              20                  25                      30

GTT AAC AAG GTC ATC GCC CCG GAT GGC GTC GCT CGT GAT ACA GTC CTC         623
Val Asn Lys Val Ile Ala Pro Asp Gly Val Ala Arg Asp Thr Val Leu
          35                  40                      45
```

```
GCC  GGG  GGC  ACG  TTC  CCG  GGC  CCA  CTC  ATC  ACA  GGA  AAG  AAG                          665
Ala  Gly  Gly  Thr  Phe  Pro  Gly  Pro  Leu  Ile  Thr  Gly  Lys  Lys
          50                        55                       60

GTATGCTAAG  TAGTCCCGCC  CCCATCATCC  TGTGGCTGAC  GTTCGACGCC  GCCAG            720

GGT  GAC  AAC  TTC  CGC  ATC  AAC  GTC  GTC  GAC  AAG  TTG  GTT  AAC  CAG  ACT   768
Gly  Asp  Asn  Phe  Arg  Ile  Asn  Val  Val  Asp  Lys  Leu  Val  Asn  Gln  Thr
              65                       70                      75

ATG  CTG  ACA  TCC  ACC  ACC  ATT  GTATGTCACT  AGCTCTCGCT  ATCTCGAGAC                          819
Met  Leu  Thr  Ser  Thr  Thr  Ile
               80

CCGCTGACCG  ACAACATTTG  CCGTAG  CAC  TGG  CAC  GGG  ATG  TTC  CAG  CAT                          869
                                His  Trp  His  Gly  Met  Phe  Gln  His
                                     85                       90

ACG  ACG  AAC  TGG  GCG  GAT  GGT  CCC  GCC  TTT  GTG  ACT  CAA  TGC  CCT  ATC   917
Thr  Thr  Asn  Trp  Ala  Asp  Gly  Pro  Ala  Phe  Val  Thr  Gln  Cys  Pro  Ile
               95                      100                     105

ACC  ACT  GGT  GAT  GAT  TTC  CTG  TAC  AAC  TTC  CGC  GTG  CCC  GAC  CAG  ACA   965
Thr  Thr  Gly  Asp  Asp  Phe  Leu  Tyr  Asn  Phe  Arg  Val  Pro  Asp  Gln  Thr
              110                      115                     120

GTACGCAAAG  GGCAGCATGC  GTACTCAAAG  ACATCTCTAA  GCATTGCTA  CCTAG            1020

GGA  ACG  TAC  TGG  TAC  CAT  AGC  CAT  CTG  GCC  TTG  CAG  TAC  TGT  GAT  GGG   1068
Gly  Thr  Tyr  Trp  Tyr  His  Ser  His  Leu  Ala  Leu  Gln  Tyr  Cys  Asp  Gly
125                      130                      135                     140

CTT  CGC  GGC  CCC  CTG  GTG  ATT  TAC  GAT  CCC  CAT  GAT  CCG  CAG  GCA  TAC   1116
Leu  Arg  Gly  Pro  Leu  Val  Ile  Tyr  Asp  Pro  His  Asp  Pro  Gln  Ala  Tyr
                    145                      150                     155

CTG  TAT  GAC  GTC  GAT  GAC  GTACGCAGCA  CAGTTTCCCT  AAAACGGTTA            1164
Leu  Tyr  Asp  Val  Asp  Asp
               160

ACTTCTAATT  CTGTAAATAT  CTTCATAG  GAG  AGC  ACC  GTT  ATC  ACT  CTG            1213
                                  Glu  Ser  Thr  Val  Ile  Thr  Leu
                                            165

GCA  GAC  TGG  TAC  CAT  ACC  CCG  GCG  CCT  CTG  CTG  CCG  CCT  GCC  GCG   1258
Ala  Asp  Trp  Tyr  His  Thr  Pro  Ala  Pro  Leu  Leu  Pro  Pro  Ala  Ala
170                      175                      180

GTACGCCTCC  ACACATCTGC  ACAGCGTTCC  GTATCTCATA  CCCTTAAAGT  TTATCGGACA            1318

ACT  TTG  ATT  AAT  GGC  CTG  GGT  CGC  TGG  CCT  GGC  AAC  CCC  ACC  GCC  GAC   1366
Thr  Leu  Ile  Asn  Gly  Leu  Gly  Arg  Trp  Pro  Gly  Asn  Pro  Thr  Ala  Asp
185                      190                      195                     200

CTA  GCC  GTC  ATC  GAA  GTC  CAG  CAC  GGA  AAG  CGC  GTATGTCATA  GCTCGGTTAT   1419
Leu  Ala  Val  Ile  Glu  Val  Gln  His  Gly  Lys  Arg
                    205                      210

CTATTCATAC  TCGCGGCCTC  GAAGCTAAAA  CCTTGTTCCA  G  TAC  CGG  TTC  CGA            1472
                                                  Tyr  Arg  Phe  Arg
                                                                 215

CTG  GTC  AGC  ACC  TCA  TGC  GAC  CCC  AAC  TAC  AAC  TTC  ACT  ATC  GAT  GGC   1520
Leu  Val  Ser  Thr  Ser  Cys  Asp  Pro  Asn  Tyr  Asn  Phe  Thr  Ile  Asp  Gly
               220                      225                     230

CAC  ACC  ATG  ACA  ATC  ATC  GAG  GCG  GAT  GGG  CAG  AAC  ACC  CAG  CCA  CAC   1568
His  Thr  Met  Thr  Ile  Ile  Glu  Ala  Asp  Gly  Gln  Asn  Thr  Gln  Pro  His
               235                      240                     245

CAA  GTC  GAC  GGA  CTT  CAG  ATC  TTC  GCG  GCA  CAG  CGG  TAC  TCC  TTC  GTT   1616
Gln  Val  Asp  Gly  Leu  Gln  Ile  Phe  Ala  Ala  Gln  Arg  Tyr  Ser  Phe  Val
              250                      255                      260

GTATGTTTTC  CGCATTTCGG  GAAAAGGAAT  TGCGCTGACA  GCTCGAGTGT  GCGTAG            1672

CTT  AAC  GCT  AAC  CAA  GCG  GTC  AAC  AAC  TAC  TGG  ATC  CGT  GCG  AAC  CCT   1720
Leu  Asn  Ala  Asn  Gln  Ala  Val  Asn  Asn  Tyr  Trp  Ile  Arg  Ala  Asn  Pro
265                      270                      275
```

```
AAC CGT GCT AAC ACT ACG GGC TTC GCC AAC GGC ATC AAC TCC GCC ATC        1768
Asn Arg Ala Asn Thr Thr Gly Phe Ala Asn Gly Ile Asn Ser Ala Ile
280             285             290             295

CTG CGC TAC AAG GGG GCG CCG ATT AAG GAG CCT ACG ACG AAC CAG ACT        1816
Leu Arg Tyr Lys Gly Ala Pro Ile Lys Glu Pro Thr Thr Asn Gln Thr
            300             305             310

ACC ATC CGG AAC TTT TTG TGG GAG ACG GAC TTG CAC CCG CTC ACT GAC        1864
Thr Ile Arg Asn Phe Leu Trp Glu Thr Asp Leu His Pro Leu Thr Asp
                315             320             325

CCA CGT GCA GTAAGTTCTA CACAGTCACC AACGGTGAGC TGTTGTCTGA                1913
Pro Arg Ala
        330

TTGCACTGTG TTATAG CCT GGC CTT CCT TTC AAG GGG GGC GTT GAC CAC          1962
               Pro Gly Leu Pro Phe Lys Gly Gly Val Asp His
                           335             340

GCT TTG AAC CTC AAC CTC ACT TTC GTACGTAGCG CCTCAGATAT CGAGTAGTCT        2016
Ala Leu Asn Leu Asn Leu Thr Phe
            345

ATCTCCTGAC CGATTGACAG AAT GGA TCG GAG TTC TTC ATC AAC GAT GCG          2066
                     Asn Gly Ser Glu Phe Phe Ile Asn Asp Ala
                             350             355

CCT TTC GTC CCT CCG ACT GTC CCG GTG CTA CTG CAG ATC CTG AAC GGA        2114
Pro Phe Val Pro Pro Thr Val Pro Val Leu Leu Gln Ile Leu Asn Gly
360             365             370             375

ACG CTC GAC GCG AAC GAC CTC CTG CCG CCC GGC AGC GTC TAC AAC CTT        2162
Thr Leu Asp Ala Asn Asp Leu Leu Pro Pro Gly Ser Val Tyr Asn Leu
            380             385             390

CCT CCG GAC TCC ACC ATC GAG CTG TCC ATT CCC GGA GGT GTG ACG GGT        2210
Pro Pro Asp Ser Thr Ile Glu Leu Ser Ile Pro Gly Gly Val Thr Gly
        395             400             405

GGC CCG CAC CCA TTC CAT TTG CAC GGG GTAATAATCT CTCTTTATAC              2257
Gly Pro His Pro Phe His Leu His Gly
        410             415

TTTGGTCTCC CGATGCTGAC TTTCACTGCT CATCTTCAG CAC GCT TTC TCC GTC         2311
                                          His Ala Phe Ser Val
                                                      420

GTG CGT AGC GCC GGC AGC ACC GAA TAC AAC TAC GCG AAC CCG GTG AAG        2359
Val Arg Ser Ala Gly Ser Thr Glu Tyr Asn Tyr Ala Asn Pro Val Lys
            425             430             435

CGC GAC ACG GTC AGC ATT GGT CTT GCG GGC GAC AAC GTC ACC GTG CGC        2407
Arg Asp Thr Val Ser Ile Gly Leu Ala Gly Asp Asn Val Thr Val Arg
        440             445             450

TTC GTG GTATGTTTTA CAGCCTCTCT ATCTCCGTGG GCGTTCGGAA GTTGACTGGG         2463
Phe Val
455

GCGTAG ACC GAC AAC CCC GGC CCG TGG TTC CTC CAC TGT CAC ATC GAC         2511
       Thr Asp Asn Pro Gly Pro Trp Phe Leu His Cys His Ile Asp
                       460             465

TTC CAT TTG CAA GCA GGC CTC GCC ATC GTG TTC GCG GAG GAC GCG CAG        2559
Phe His Leu Gln Ala Gly Leu Ala Ile Val Phe Ala Glu Asp Ala Gln
470             475             480             485

GAC ACG AAG CTT GTG AAC CCC GTC CCT GTACGTCTTC TGGATGCATG              2606
Asp Thr Lys Leu Val Asn Pro Val Pro
            490

CGCTCCGCAC AGTGACTCAT CTTTTGCAAC AG GAG GAC TGG AAC AAG CTG TGC        2659
                                   Glu Asp Trp Asn Lys Leu Cys
                                               495             500

CCC ACC TTC GAT AAG GCG ATG AAC ATC ACG GTT TGAGCGATGC                 2702
Pro Thr Phe Asp Lys Ala Met Asn Ile Thr Val
            505             510
```

```
GTGGCGCTCA TGGTCATTTT CTTGGAATCT TTGCATAGGG CTGCAGCACG CTGGATACTC    2762

TTTCCCTTAG CAGGATATTA TTTAATGACC CCTGCGTTTA GTGCTTAGTT AGCTTTACTA    2822

CTGGTTGTAA TGTACGCAGC ATGCGTAATT CGGATAATGC TATCAATGTG TATATTATGA    2882

CACGCGTCAT GCGCGATGCT TGAGTTGCAA GGTCGGTTTC CGATGCTCGA CATAAACGTT    2942

TCACTTACAT ACACATTGGG TCTAGAACTG GATCTATCCA TGTATACAAA AACTCCTCAT    3002

ACAGCTGACT GGGGCGCTCT AGAGCATGGG TCCGATTGAT CAGATGTCGC GAACACGAGC    3062

CTCCTGAGCT CGAGGACTCT GAGAAGCGGC GGTGCGTTCT                          3102
```

( 2 ) INFORMATION FOR SEQ ID NO:6:

( i ) SEQUENCE CHARACTERISTICS:
        ( A ) LENGTH: 512 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Polyporus pinsitus ( x i ) SEQUENCE DESCRIPTION: SEQ ID NO: 6:

```
Met  Ser  Phe  Ser  Ser  Leu  Arg  Arg  Ala  Leu  Val  Phe  Leu  Gly  Ala  Cys
  1             5                        10                       15

Ser  Ser  Ala  Leu  Ala  Ser  Ile  Gly  Pro  Val  Thr  Glu  Leu  Asp  Ile  Val
            20                       25                       30

Asn  Lys  Val  Ile  Ala  Pro  Asp  Gly  Val  Ala  Arg  Asp  Thr  Val  Leu  Ala
            35                       40                       45

Gly  Gly  Thr  Phe  Pro  Gly  Pro  Leu  Ile  Thr  Gly  Lys  Lys  Gly  Asp  Asn
       50                       55                       60

Phe  Arg  Ile  Asn  Val  Val  Asp  Lys  Leu  Val  Asn  Gln  Thr  Met  Leu  Thr
 65                       70                       75                       80

Ser  Thr  Thr  Ile  His  Trp  His  Gly  Met  Phe  Gln  His  Thr  Thr  Asn  Trp
                      85                       90                       95

Ala  Asp  Gly  Pro  Ala  Phe  Val  Thr  Gln  Cys  Pro  Ile  Thr  Thr  Gly  Asp
                100                      105                      110

Asp  Phe  Leu  Tyr  Asn  Phe  Arg  Val  Pro  Asp  Gln  Thr  Gly  Thr  Tyr  Trp
           115                      120                      125

Tyr  His  Ser  His  Leu  Ala  Leu  Gln  Tyr  Cys  Asp  Gly  Leu  Arg  Gly  Pro
      130                      135                      140

Leu  Val  Ile  Tyr  Asp  Pro  His  Asp  Pro  Gln  Ala  Tyr  Leu  Tyr  Asp  Val
145                      150                      155                      160

Asp  Asp  Glu  Ser  Thr  Val  Ile  Thr  Leu  Ala  Asp  Trp  Tyr  His  Thr  Pro
                165                      170                      175

Ala  Pro  Leu  Leu  Pro  Pro  Ala  Ala  Thr  Leu  Ile  Asn  Gly  Leu  Gly  Arg
                180                      185                      190

Trp  Pro  Gly  Asn  Pro  Thr  Ala  Asp  Leu  Ala  Val  Ile  Glu  Val  Gln  His
           195                      200                      205

Gly  Lys  Arg  Tyr  Arg  Phe  Arg  Leu  Val  Ser  Thr  Ser  Cys  Asp  Pro  Asn
      210                      215                      220

Tyr  Asn  Phe  Thr  Ile  Asp  Gly  His  Thr  Met  Thr  Ile  Ile  Glu  Ala  Asp
225                      230                      235                      240

Gly  Gln  Asn  Thr  Gln  Pro  His  Gln  Val  Asp  Gly  Leu  Gln  Ile  Phe  Ala
                245                      250                      255

Ala  Gln  Arg  Tyr  Ser  Phe  Val  Leu  Asn  Ala  Asn  Gln  Ala  Val  Asn  Asn
           260                      265                      270
```

```
Tyr Trp Ile Arg Ala Asn Pro Asn Arg Ala Asn Thr Thr Gly Phe Ala
    275             280             285

Asn Gly Ile Asn Ser Ala Ile Leu Arg Tyr Lys Gly Ala Pro Ile Lys
    290             295             300

Glu Pro Thr Thr Asn Thr Thr Ile Arg Asn Phe Leu Trp Glu Thr
305             310             315             320

Asp Leu His Pro Leu Thr Asp Pro Arg Ala Pro Gly Leu Pro Phe Lys
                325             330             335

Gly Gly Val Asp His Ala Leu Asn Leu Asn Leu Thr Phe Asn Gly Ser
            340             345             350

Glu Phe Phe Ile Asn Asp Ala Pro Phe Val Pro Pro Thr Val Pro Val
        355             360             365

Leu Leu Gln Ile Leu Asn Gly Thr Leu Asp Ala Asn Asp Leu Leu Pro
    370             375             380

Pro Gly Ser Val Tyr Asn Leu Pro Pro Asp Ser Thr Ile Glu Leu Ser
385             390             395             400

Ile Pro Gly Gly Val Thr Gly Gly Pro His Pro Phe His Leu His Gly
                405             410             415

His Ala Phe Ser Val Val Arg Ser Ala Gly Ser Thr Glu Tyr Asn Tyr
            420             425             430

Ala Asn Pro Val Lys Arg Asp Thr Val Ser Ile Gly Leu Ala Gly Asp
        435             440             445

Asn Val Thr Val Arg Phe Val Thr Asp Asn Pro Gly Pro Trp Phe Leu
    450             455             460

His Cys His Ile Asp Phe His Leu Gln Ala Gly Leu Ala Ile Val Phe
465             470             475             480

Ala Glu Asp Ala Gln Asp Thr Lys Leu Val Asn Pro Val Pro Glu Asp
                485             490             495

Trp Asn Lys Leu Cys Pro Thr Phe Asp Lys Ala Met Asn Ile Thr Val
                500             505             510
```

( 2 ) INFORMATION FOR SEQ ID NO:7:

( i ) SEQUENCE CHARACTERISTICS:
        ( A ) LENGTH: 2860 base pairs
        ( B ) TYPE: nucleic acid
        ( C ) STRANDEDNESS: single
        ( D ) TOPOLOGY: linear ( i x ) FEATURE:
        ( A ) NAME/KEY: intron
        ( B ) LOCATION: 851..905

( i x ) FEATURE:
        ( A ) NAME/KEY: intron
        ( B ) LOCATION: 1266..1320

( i x ) FEATURE:
        ( A ) NAME/KEY: intron
        ( B ) LOCATION: 1351..1376

( i x ) FEATURE:
        ( A ) NAME/KEY: intron
        ( B ) LOCATION: 1416..1468

( i x ) FEATURE:
        ( A ) NAME/KEY: intron
        ( B ) LOCATION: 1625..1683

( i x ) FEATURE:
        ( A ) NAME/KEY: intron
        ( B ) LOCATION: 1882..1934

( i x ) FEATURE:

( A ) NAME/KEY: intron
( B ) LOCATION: 2202..2252

( i x ) FEATURE:
   ( A ) NAME/KEY: intron
   ( B ) LOCATION: 2370..2425

( i x ) FEATURE:
   ( A ) NAME/KEY: intron
   ( B ) LOCATION: 2543..2599

( i x ) FEATURE:
   ( A ) NAME/KEY: CDS
   ( B ) LOCATION: join(540..725, 782..850, 906..1025, 1086..1265,
              1321..1350, 1377..1415, 1469..1624, 1684..1881,
              1935..2201, 2253..2369, 2426..2542, 2600..2653)

( x i ) SEQUENCE DESCRIPTION: SEQ ID NO:7:

```
GGGGGGCGCG  TCAATGGTCC  GTTTGCGAAC  ACATATGCAG  GATAAACAGT  GCGAAATATC         60

AATGTGGCGG  CGACACAACC  TCGCCGGCCG  ACACTCGACG  CTGTTGATCA  TGATCATGTC        120

TTGTGAGCAT  TCTATACGCA  GCCTTGGAAA  TCTCAGGCGA  ATTTGTCTGA  ATTGCGCTGG        180

GAGGCTGGCA  GCGCAGATCG  GTGTGTCGGT  GCAGTAGCCG  ACGCAGCACC  TGGCGGAAGC        240

CGACATCTCG  GGTACGACTT  GATCTCCGCC  AGATCACTGC  GGTTCCGCCA  TCGGCCGCGG        300

GGCCCATTCT  GTGTGTGCGC  TGTAGCACTC  TGCATTCAGG  CTCAACGTAT  CCATGCTAGA        360

GGACCGTCCA  GCTGTTGGCG  CACGATTCGC  GCAGAAAGCT  GTACAGGCAG  ATATAAGGAT        420

GTCCGTCCGT  CAGAGACTCG  TCACTCACAA  GCCTCTTTTC  CTCTTCGCCT  TTCCAGCCTC        480

TTCCAACGCC  TGCCATCGTC  CTCTTAGTTC  GCTCGTCCAT  TCTTTCTGCG  TAGTTAATC         539
```

```
ATG  GGC  AGG  TTC  TCA  TCT  CTC  TGC  GCG  CTC  ACC  GCC  GTC  ATC  CAC  TCT         587
Met  Gly  Arg  Phe  Ser  Ser  Leu  Cys  Ala  Leu  Thr  Ala  Val  Ile  His  Ser
 1                     5                        10                       15

TTT  GGT  CGT  GTC  TCC  GCC  GCT  ATC  GGG  CCT  GTG  ACC  GAC  CTC  ACC  ATC         635
Phe  Gly  Arg  Val  Ser  Ala  Ala  Ile  Gly  Pro  Val  Thr  Asp  Leu  Thr  Ile
                 20                       25                       30

TCC  AAT  GGG  GAC  GTT  TCT  CCC  GAC  GGC  TTC  ACT  CGT  GCC  GCA  GTG  CTT         683
Ser  Asn  Gly  Asp  Val  Ser  Pro  Asp  Gly  Phe  Thr  Arg  Ala  Ala  Val  Leu
             35                       40                       45

GCA  AAC  GGC  GTC  TTC  CCG  GGT  CCT  CTT  ATC  ACG  GGA  AAC  AAG                  725
Ala  Asn  Gly  Val  Phe  Pro  Gly  Pro  Leu  Ile  Thr  Gly  Asn  Lys
         50                       55                       60
```

```
GTACGTGGCA  TGCGTTCAGT  CTACACCCTA  CAAGCCTTCT  AACTCTTTTA  CCACAG             781
```

```
GGC  GAC  AAC  TTC  CAG  ATC  AAT  GTT  ATC  GAC  AAC  CTC  TCT  AAC  GAG  ACG         829
Gly  Asp  Asn  Phe  Gln  Ile  Asn  Val  Ile  Asp  Asn  Leu  Ser  Asn  Glu  Thr
                     65                       70                       75

ATG  TTG  AAG  TCG  ACC  TCC  ATC  GTATGTGCTT  CTACTGCTTC  TTAGTCTTGG          880
Met  Leu  Lys  Ser  Thr  Ser  Ile
 80                       85
```

```
CAATGGCTCA  AGGTCTCCTC  CGCAG  CAT  TGG  CAC  GGC  TTC  TTC  CAG  AAG  GGT        932
                                His  Trp  His  Gly  Phe  Phe  Gln  Lys  Gly
                                                            90

ACT  AAC  TGG  GCT  GAT  GGA  GCT  GCC  TTC  GTC  AAC  CAG  TGC  CCT  ATC  GCG         980
Thr  Asn  Trp  Ala  Asp  Gly  Ala  Ala  Phe  Val  Asn  Gln  Cys  Pro  Ile  Ala
 95                      100                      105                      110

ACG  GGG  AAC  TCT  TTC  CTT  TAC  GAC  TTC  ACC  GCG  ACG  GAC  CAA  GCA             1025
Thr  Gly  Asn  Ser  Phe  Leu  Tyr  Asp  Phe  Thr  Ala  Thr  Asp  Gln  Ala
                 115                      120                      125
```

```
GTCAGTGCCT  GTGGCGCTTA  TGTTTTCCCG  TAATCAGCAG  CTAACACTCC  GCACCCACAG       1085
```

```
GGC  ACC  TTC  TGG  TAC  CAC  AGT  CAC  TTG  TCT  ACG  CAG  TAC  TGC  GAT  GGT        1133
Gly  Thr  Phe  Trp  Tyr  His  Ser  His  Leu  Ser  Thr  Gln  Tyr  Cys  Asp  Gly
                         130                      135                      140
```

```
TTG CGG GGC CCG ATG GTC GTA TAC GAC CCG AGT GAC CCG CAT GCG GAC          1181
Leu Arg Gly Pro Met Val Val Tyr Asp Pro Ser Asp Pro His Ala Asp
        145                 150                 155

CTT TAC GAC GTC GAC GAC GAG ACC ACG ATC ATC ACG CTC TCT GAT TGG          1229
Leu Tyr Asp Val Asp Asp Glu Thr Thr Ile Ile Thr Leu Ser Asp Trp
    160                 165                 170

TAT CAC ACC GCT GCT TCG CTC GGT GCT GCC TTC CCG  GTAAGTTTAC              1275
Tyr His Thr Ala Ala Ser Leu Gly Ala Ala Phe Pro
175                 180                 185

CCCAGCGCAC GGAGTTAAGA CCGGATCTAA CTGTAATACG TTCAG ATT GGC TCG            1329
                                                  Ile Gly Ser

GAC TCT ACC CTG ATT AAC GGC GTTGGCCGCT TCGCGGGTGG TGACAG ACT GAC         1382
Asp Ser Thr Leu Ile Asn Gly                             Thr Asp
    190             195

CTT GCG GTT ATC ACT GTC GAG CAG GGC AAG CGC GTTAGTGATA CCCTCTACAG        1435
Leu Ala Val Ile Thr Val Glu Gln Gly Lys Arg
        200                 205

TTGACACTGT GCCATTGCTG ACAGTACTCT CAG TAC CGT ATG CGT CTT CTC TCG         1489
                                   Tyr Arg Met Arg Leu Leu Ser
                                       210                 215

CTG TCT TGC GAC CCC AAC TAT GTC TTC TCC ATT GAC GGC CAC AAC ATG          1537
Leu Ser Cys Asp Pro Asn Tyr Val Phe Ser Ile Asp Gly His Asn Met
                220                 225                 230

ACC ATC ATC GAG GCC GAC GCC GTC AAC CAC GAG CCC CTC ACG GTT GAC          1585
Thr Ile Ile Glu Ala Asp Ala Val Asn His Glu Pro Leu Thr Val Asp
            235                 240                 245

TCC ATC CAG ATC TAC GCC GGC CAA CGT TAC TCC TTC GTC GTACGTATTC           1634
Ser Ile Gln Ile Tyr Ala Gly Gln Arg Tyr Ser Phe Val
        250                 255                 260

CGAACAGCCA TGATCACGCC AAGCCCGATG CTAACGCGCC TACCCTCAG CTT ACC            1689
                                                      Leu Thr

GCT GAC CAG GAC ATC GAC AAC TAC TTC ATC CGT GCC CTG CCC AGC GCC          1737
Ala Asp Gln Asp Ile Asp Asn Tyr Phe Ile Arg Ala Leu Pro Ser Ala
            265                 270                 275

GGT ACC ACC TCG TTC GAC GGC GGC ATC AAC TCG GCT ATC CTG CGC TAC          1785
Gly Thr Thr Ser Phe Asp Gly Gly Ile Asn Ser Ala Ile Leu Arg Tyr
280                 285                 290

TCT GGT GCC TCC GAG GTT GAC CCG ACG ACC ACG GAG ACC ACG AGC GTC          1833
Ser Gly Ala Ser Glu Val Asp Pro Thr Thr Thr Glu Thr Thr Ser Val
295                 300                 305                 310

CTC CCC CTC GAC GAG GCG AAC CTC GTG CCC CTT GAC AGC CCC GCT GCT          1881
Leu Pro Leu Asp Glu Ala Asn Leu Val Pro Leu Asp Ser Pro Ala Ala
                315                 320                 325

GTACGTCGTA TTCTGCGCTT GCAAGGATCG CACATACTAA CATGCTCTTG TAG CCC           1937
                                                          Pro

GGT GAC CCC AAC ATT GGC GGT GTC GAC TAC GCG CTG AAC TTG GAC TTC          1985
Gly Asp Pro Asn Ile Gly Gly Val Asp Tyr Ala Leu Asn Leu Asp Phe
        330                 335                 340

AAC TTC GAT GGC ACC AAC TTC TTC ATC AAC GAC GTC TCC TTC GTG TCC          2033
Asn Phe Asp Gly Thr Asn Phe Phe Ile Asn Asp Val Ser Phe Val Ser
    345                 350                 355

CCC ACG GTC CCT GTC CTC CTC CAG ATT CTT AGC GGC ACC ACC TCC GCG          2081
Pro Thr Val Pro Val Leu Leu Gln Ile Leu Ser Gly Thr Thr Ser Ala
360                 365                 370                 375

GCC GAC CTT CTC CCC AGC GGT AGT CTC TTC GCG GTC CCG TCC AAC TCG          2129
Ala Asp Leu Leu Pro Ser Gly Ser Leu Phe Ala Val Pro Ser Asn Ser
            380                 385                 390

ACG ATC GAG ATC TCG TTC CCC ATC ACC GCG ACG AAC GCT CCC GGC GCG          2177
Thr Ile Glu Ile Ser Phe Pro Ile Thr Ala Thr Asn Ala Pro Gly Ala
```

```
                         395                      400                       405
CCG CAT CCC TTC CAC TTG CAC  GGT GTACGTGTCC CATCTCATAT GCTACGGAGC            2231
Pro His Pro Phe His Leu His  Gly
    410                      415

TCCACGCTGA CCGCCCTATA G CAC ACC TTC TCT ATC GTT CGT ACC GCC GGC              2282
                       His Thr Phe Ser Ile Val Arg Thr Ala Gly
                                       420                    425

AGC ACG GAT ACG AAC TTC GTC AAC CCC GTC CGC CGC GAC GTC GTG AAC              2330
Ser Thr Asp Thr Asn Phe Val Asn Pro Val Arg Arg Asp Val Val Asn
                430                     435                 440

ACC GGT ACC GTC GGC GAC AAC GTC ACC ATC CGC TTC ACG GTACGCAGCA               2379
Thr Gly Thr Val Gly Asp Asn Val Thr Ile Arg Phe Thr
            445                     450

CTCTCCTAAC ATTCCCACTG CGCGATCACT GACTCCTCGC CCACAG ACT GAC AAC               2434
                                                   Thr Asp Asn
                                                   455

CCC GGC CCC TGG TTC CTC CAC TGC CAC ATC GAC TTC CAC TTG GAG GCC              2482
Pro Gly Pro Trp Phe Leu His Cys His Ile Asp Phe His Leu Glu Ala
        460                     465                     470

GGT TTC GCC ATC GTC TTC AGC GAG GAC ACC GCC GAC GTC TCG AAC ACG              2530
Gly Phe Ala Ile Val Phe Ser Glu Asp Thr Ala Asp Val Ser Asn Thr
    475                     480                     485

ACC ACG CCC TCG GTACGTTGTG CTCCCGTGCC CATCTCCGCG CGCCTGACTA                  2582
Thr Thr Pro Ser
490

ACGAGCACCC CTTACAG ACT GCT TGG GAA GAT CTG TGC CCC ACG TAC AAC               2632
                   Thr Ala Trp Glu Asp Leu Cys Pro Thr Tyr Asn
                           495                 500

GCT CTT GAC TCA TCC GAC CTC TAATCGGTTC AAAGGGTCGC TCGCTACCTT                 2683
Ala Leu Asp Ser Ser Asp Leu
505                 510

AGTAGGTAGA CTTATGCACC GGACATTATC TACAATGGAC TTTAATTTGG GTTAACGGCC            2743
GTTATACATA CGCGCACGTA GTATAAAGGT TCTCTGGATT GGTCGGACCT ACAGACTGCA            2803
ATTTTCGTGA CCTATCAACT GTATATTGAA GCACGACAGT GAATGGAAAT AGAGACA              2860
```

( 2 ) INFORMATION FOR SEQ ID NO:8:

( i ) SEQUENCE CHARACTERISTICS:
        ( A ) LENGTH: 511 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Gly Arg Phe Ser Ser Leu Cys Ala Leu Thr Ala Val Ile His Ser
1               5                   10                  15

Phe Gly Arg Val Ser Ala Ala Ile Gly Pro Val Thr Asp Leu Thr Ile
                20                  25                  30

Ser Asn Gly Asp Val Ser Pro Asp Gly Phe Thr Arg Ala Ala Val Leu
            35                  40                  45

Ala Asn Gly Val Phe Pro Gly Pro Leu Ile Thr Gly Asn Lys Gly Asp
        50                  55                  60

Asn Phe Gln Ile Asn Val Ile Asp Asn Leu Ser Asn Glu Thr Met Leu
65                  70                  75                  80

Lys Ser Thr Ser Ile His Trp His Gly Phe Phe Gln Lys Gly Thr Asn
                85                  90                  95

Trp Ala Asp Gly Ala Ala Phe Val Asn Gln Cys Pro Ile Ala Thr Gly
                100                 105                 110
```

| Asn | Ser | Phe | Leu | Tyr | Asp | Phe | Thr | Ala | Thr | Asp | Gln | Ala | Gly | Thr | Phe |
|---|---|---|---|---|---|---|---|---|---|---|---|---|---|---|---|
| | | 115 | | | | | 120 | | | | | 125 | | | |
| Trp | Tyr | His | Ser | His | Leu | Ser | Thr | Gln | Tyr | Cys | Asp | Gly | Leu | Arg | Gly |
| | 130 | | | | | 135 | | | | | 140 | | | | |
| Pro | Met | Val | Val | Tyr | Asp | Pro | Ser | Asp | Pro | His | Ala | Asp | Leu | Tyr | Asp |
| 145 | | | | | 150 | | | | | 155 | | | | | 160 |
| Val | Asp | Asp | Glu | Thr | Thr | Ile | Ile | Thr | Leu | Ser | Asp | Trp | Tyr | His | Thr |
| | | | | 165 | | | | | 170 | | | | | 175 | |
| Ala | Ala | Ser | Leu | Gly | Ala | Ala | Phe | Pro | Ile | Gly | Ser | Asp | Ser | Thr | Leu |
| | | | 180 | | | | | 185 | | | | | 190 | | |
| Ile | Asn | Gly | Thr | Asp | Leu | Ala | Val | Ile | Thr | Val | Glu | Gln | Gly | Lys | Arg |
| | | 195 | | | | | 200 | | | | | 205 | | | |
| Tyr | Arg | Met | Arg | Leu | Leu | Ser | Leu | Ser | Cys | Asp | Pro | Asn | Tyr | Val | Phe |
| | 210 | | | | | 215 | | | | | 220 | | | | |
| Ser | Ile | Asp | Gly | His | Asn | Met | Thr | Ile | Ile | Glu | Ala | Asp | Ala | Val | Asn |
| 225 | | | | | 230 | | | | | 235 | | | | | 240 |
| His | Glu | Pro | Leu | Thr | Val | Asp | Ser | Ile | Gln | Ile | Tyr | Ala | Gly | Gln | Arg |
| | | | | 245 | | | | | 250 | | | | | 255 | |
| Tyr | Ser | Phe | Val | Leu | Thr | Ala | Asp | Gln | Asp | Ile | Asp | Asn | Tyr | Phe | Ile |
| | | | 260 | | | | | 265 | | | | | 270 | | |
| Arg | Ala | Leu | Pro | Ser | Ala | Gly | Thr | Thr | Ser | Phe | Asp | Gly | Gly | Ile | Asn |
| | | | 275 | | | | | 280 | | | | | 285 | | |
| Ser | Ala | Ile | Leu | Arg | Tyr | Ser | Gly | Ala | Ser | Glu | Val | Asp | Pro | Thr | Thr |
| | | 290 | | | | | 295 | | | | | 300 | | | |
| Thr | Glu | Thr | Thr | Ser | Val | Leu | Pro | Leu | Asp | Glu | Ala | Asn | Leu | Val | Pro |
| 305 | | | | | 310 | | | | | 315 | | | | | 320 |
| Leu | Asp | Ser | Pro | Ala | Ala | Pro | Gly | Asp | Pro | Asn | Ile | Gly | Gly | Val | Asp |
| | | | | 325 | | | | | 330 | | | | | 335 | |
| Tyr | Ala | Leu | Asn | Leu | Asp | Phe | Asn | Phe | Asp | Gly | Thr | Asn | Phe | Phe | Ile |
| | | | 340 | | | | | 345 | | | | | 350 | | |
| Asn | Asp | Val | Ser | Phe | Val | Ser | Pro | Thr | Val | Pro | Val | Leu | Leu | Gln | Ile |
| | | 355 | | | | | 360 | | | | | 365 | | | |
| Leu | Ser | Gly | Thr | Thr | Ser | Ala | Ala | Asp | Leu | Leu | Pro | Ser | Gly | Ser | Leu |
| | 370 | | | | | 375 | | | | | 380 | | | | |
| Phe | Ala | Val | Pro | Ser | Asn | Ser | Thr | Ile | Glu | Ile | Ser | Phe | Pro | Ile | Thr |
| 385 | | | | | 390 | | | | | 395 | | | | | 400 |
| Ala | Thr | Asn | Ala | Pro | Gly | Ala | Pro | His | Pro | Phe | His | Leu | His | Gly | His |
| | | | | 405 | | | | | 410 | | | | | 415 | |
| Thr | Phe | Ser | Ile | Val | Arg | Thr | Ala | Gly | Ser | Thr | Asp | Thr | Asn | Phe | Val |
| | | | 420 | | | | | 425 | | | | | 430 | | |
| Asn | Pro | Val | Arg | Arg | Asp | Val | Val | Asn | Thr | Gly | Thr | Val | Gly | Asp | Asn |
| | | 435 | | | | | 440 | | | | | 445 | | | |
| Val | Thr | Ile | Arg | Phe | Thr | Thr | Asp | Asn | Pro | Gly | Pro | Trp | Phe | Leu | His |
| | 450 | | | | | 455 | | | | | 460 | | | | |
| Cys | His | Ile | Asp | Phe | His | Leu | Glu | Ala | Gly | Phe | Ala | Ile | Val | Phe | Ser |
| 465 | | | | | 470 | | | | | 475 | | | | | 480 |
| Glu | Asp | Thr | Ala | Asp | Val | Ser | Asn | Thr | Thr | Thr | Pro | Ser | Thr | Ala | Trp |
| | | | | 485 | | | | | 490 | | | | | 495 | |
| Glu | Asp | Leu | Cys | Pro | Thr | Tyr | Asn | Ala | Leu | Asp | Ser | Ser | Asp | Leu | |
| | | | 500 | | | | | 505 | | | | | 510 | | |

( 2 ) INFORMATION FOR SEQ ID NO: 9:

( i ) SEQUENCE CHARACTERISTICS:

(A) LENGTH: 2925 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Polyporus pinsitus (ix) FEATURE:
(A) NAME/KEY: intron
(B) LOCATION: 734..808

(ix) FEATURE:
(A) NAME/KEY: intron
(B) LOCATION: 878..932

(ix) FEATURE:
(A) NAME/KEY: intron
(B) LOCATION: 1051..1104

(ix) FEATURE:
(A) NAME/KEY: intron
(B) LOCATION: 1219..1270

(ix) FEATURE:
(A) NAME/KEY: intron
(B) LOCATION: 1336..1397

(ix) FEATURE:
(A) NAME/KEY: intron
(B) LOCATION: 1713..7744

(ix) FEATURE:
(A) NAME/KEY: intron
(B) LOCATION: 2030..2085

(ix) FEATURE:
(A) NAME/KEY: intron
(B) LOCATION: 2308..2375

(ix) FEATURE:
(A) NAME/KEY: intron
(B) LOCATION: 2492..2569

(ix) FEATURE:
(A) NAME/KEY: CDS
(B) LOCATION: join (733..809, 877..933, 1050..1105, 1218..1271 2542..2600).

(xi) SEQUENCE DESCRIPTION: SEQ ID NO: 9:

```
CTCATAACTC TTCGCTTCTA GCATGGGGGC TGCGCACACC TGACAGACCC TTCGGGAGGC        60

GAACTCGAAT GCAGCGTACT CTATCNCACC TCCAGGAAAG GTAGGGATGG ACNCCGTGCA       120

CCAACAACTG TCTCTCCACC AGCAACCATC CCTTGGATAT GTCTCCACAC ACCCGGTGTC       180

TACAAGCGGG GATCTGTGCT GGTGAAGTGC TGTCTCCGGA GCGGCGGCGG CGAGCGACCA       240

GAACCCGAAC CAGTGCTAGT GCCCGACACC CGCGAGACAA TTGTGCAGGG TGAGTTATAT       300

TCTTCGTGAG ACGGCGCTGC GCGTCGGCAC TGAAAGCGTC GCAGTTAGGT GATGCAGCGG       360

TCCGCGCTAT TTTTGACGTC TGGCAGCTAT CCTAAGCCGC GCCTCCATAC ACCCCAGGCG       420

CTCTCGTTTG CTATAGGTAT AAATCCCTCA GCTTCAGAGC GTCGATCCTC ATCCACACG        480

ACACCCGTTT CAGTCTTCTC GTAGCGCATT CCCTAGCCGC CCAGCCTCCG CTTTCGTTTT       540

CAAC ATG GGC AAG TAT CAC TCT TTT GTG AAC GTC GTC GCC CTT AGT CTT       589
     Met Gly Lys Tyr His Ser Phe Val Asn Val Val Ala Leu Ser Leu
     1               5                   10                  15

TCT TTG AGC GGT CGT GTG TTC GGC GCC ATT GGG CCC GTC ACC GAC TTG           637
Ser Leu Ser Gly Arg Val Phe Gly Ala Ile Gly Pro Val Thr Asp Leu
            20                  25                  30

ACT ATC TCT AAC GCC GAT GTT ACG CCT GAC GGC ATT ACT CGT GCT GCT           685
```

```
Thr Ile Ser Asn Ala Asp Val Thr Pro Asp Gly Ile Thr Arg Ala Ala
         35                  40                  45

GTC CTC GCG GGC GGT GTT TTC CCC GGG CCC CTC ATT ACC GGC AAC AAG          733
Val Leu Ala Gly Gly Val Phe Pro Gly Pro Leu Ile Thr Gly Asn Lys
         50                  55                  60

GTGAGCCGCG AAACCTTCTA CTAGCGCGCT CGTACGGTGC ACCGTTACTG AAGCCACACT        793
TTGCGCTGTC AACAG GGG GAT GAA TTC CAG ATC AAT GTC ATC GAC AAC CTG         844
               Gly Asp Glu Phe Gln Ile Asn Val Ile Asp Asn Leu
                       65                  70                  75

ACC AAC GAG ACC ATG TTG AAG TCG ACC ACA ATC GTAAGGTGCT TGCTCCCATA        897
Thr Asn Glu Thr Met Leu Lys Ser Thr Thr Ile
         80                  85

ATTAAGCCCG TCGCTGACTC GAAGTTTATC TGTAG CAC TGG CAT GGT ATC TTC           950
                                       His Trp His Gly Ile Phe
                                                             90

CAG GCC GGC ACC AAC TGG GCA GAC GGC GCG GCC TTC GTG AAC CAG TGC          998
Gln Ala Gly Thr Asn Trp Ala Asp Gly Ala Ala Phe Val Asn Gln Cys
             95                 100                 105

CCT ATC GCC ACG GGA AAC TCG TTC TTG TAC GAC TTC ACC GTT CCT GAT         1046
Pro Ile Ala Thr Gly Asn Ser Phe Leu Tyr Asp Phe Thr Val Pro Asp
        110                 115                 120

CAA GCC GTACGTTTAT ACACTTCCCT TTCTGCGGCA TACTCTGACG CGCCGCTGGA          1102
Gln Ala
125

TCAG GGC ACC TTC TGG TAC CAC AGC CAC CTG TCC ACC CAG TAC TGT GAC        1151
     Gly Thr Phe Trp Tyr His Ser His Leu Ser Thr Gln Tyr Cys Asp
              130                 135                 140

GGC CTG CGC GGT CCT CTT GTG GTC TAC GAC CCC GAC GAT CCC AAC GCG        1199
Gly Leu Arg Gly Pro Leu Val Val Tyr Asp Pro Asp Asp Pro Asn Ala
        145                 150                 155

TCT CTT TAC GAC GTC GAT GAC GTAAGCAGGC TACTTGTGGA CTTGTATGGA           1250
Ser Leu Tyr Asp Val Asp Asp
        160

TGTATCTCAC GCTCCCCTAC AG GAT ACT ACG GTT ATT ACG CTT GCG GAC TGG       1302
                         Asp Thr Thr Val Ile Thr Leu Ala Asp Trp
                                  165                 170

TAC CAC ACT GCG GCG AAG CTG GGC CCT GCC TTC CCC GTGAGTCTAC             1348
Tyr His Thr Ala Ala Lys Leu Gly Pro Ala Phe Pro
175                 180                 185

TCTTCCTCGT GTGTTAACAT AGGTGACGGC CGCTGATACG AGAGCTACCA G GCG GGT       1405
                                                          Ala Gly

CCG GAT AGC GTC TTG ATC AAT GGT CTT GGT CGG TTC TCC GGC GAT GGT        1453
Pro Asp Ser Val Leu Ile Asn Gly Leu Gly Arg Phe Ser Gly Asp Gly
        190                 195                 200

GGA GGA GCG ACA AAC CTC ACC GTG ATC ACC GTC ACG CAA GGC AAA CGG        1501
Gly Gly Ala Thr Asn Leu Thr Val Ile Thr Val Thr Gln Gly Lys Arg
205                 210                 215                 220

GTGAGTCCGC CCTGAGCTGG CCTCAATAGC GATATTGACG AGTCCATGCC CTCCCAG         1558

TAC CGC TTC CGC CTT GTG TCG ATC TCG TGC GAC CCC AAC TTC ACG TTC        1606
Tyr Arg Phe Arg Leu Val Ser Ile Ser Cys Asp Pro Asn Phe Thr Phe
                    225                 230                 235

TCG ATC GAC GGG CAC AAC ATG ACC ATC ATC GAG GTG GAC GGT GTC AAC        1654
Ser Ile Asp Gly His Asn Met Thr Ile Ile Glu Val Asp Gly Val Asn
        240                 245                 250

CAC GAG GCC TTG GAC GTC GAC TCC ATT CAG ATT TTT GCG GGG CAG CGG        1702
His Glu Ala Leu Asp Val Asp Ser Ile Gln Ile Phe Ala Gly Gln Arg
        255                 260                 265

TAC TCC TTC ATC GTACGTTCCC TTGCCCTCGT GCTATATCCG CCCGTCTGCT            1754
Tyr Ser Phe Ile
270
```

```
CACAGAGGCT TCTATATCGC AG CTC AAC GCC AAC CAG TCC ATC GAC AAC              1803
                         Leu Asn Ala Asn Gln Ser Ile Asp Asn
                             275                 280

TAC TGG ATC CGC GCG ATC CCC AAC ACC GGT ACC ACC GAC ACC ACG GGC           1851
Tyr Trp Ile Arg Ala Ile Pro Asn Thr Gly Thr Thr Asp Thr Thr Gly
            285                 290                 295

GGC GTG AAC TCT GCT ATT CTT CGC TAC GAC ACC GCA GAA GAT ATC GAG           1899
Gly Val Asn Ser Ala Ile Leu Arg Tyr Asp Thr Ala Glu Asp Ile Glu
        300                 305                 310

CCT ACG ACC AAC GCG ACC ACC TCC GTC ATC CCT CTC ACC GAG ACG GAT           1947
Pro Thr Thr Asn Ala Thr Thr Ser Val Ile Pro Leu Thr Glu Thr Asp
    315                 320                 325

CTG GTG CCG CTC GAC AAC CCT GCG GCT CCC GGT GAC CCC CAG GTC GGC           1995
Leu Val Pro Leu Asp Asn Pro Ala Ala Pro Gly Asp Pro Gln Val Gly
330                 335                 340                 345

GGT GTT GAC CTG GCT ATG AGT CTC GAC TTC TCC TTC GTGAGTCCCA                2041
Gly Val Asp Leu Ala Met Ser Leu Asp Phe Ser Phe
                350                 355

CAGCACTCCG CGCCATTTCG CTTATTTACG CAGGAGTATT GTTCAG AAC GGT TCC            2096
                                                  Asn Gly Ser
                                                          360

AAC TTC TTT ATC AAC AAC GAG ACC TTC GTC CCG CCC ACA GTT CCC GTG           2144
Asn Phe Phe Ile Asn Asn Glu Thr Phe Val Pro Pro Thr Val Pro Val
            365                 370                 375

CTC CTG CAG ATT TTG AGT GGT GCG CAG GAC GCG GCG AGC CTG CTC CCC           2192
Leu Leu Gln Ile Leu Ser Gly Ala Gln Asp Ala Ala Ser Leu Leu Pro
        380                 385                 390

AAC GGG AGT GTC TAC ACA CTC CCT TCG AAC TCG ACC ATT GAG ATC TCG           2240
Asn Gly Ser Val Tyr Thr Leu Pro Ser Asn Ser Thr Ile Glu Ile Ser
    395                 400                 405

TTC CCC ATC ATC ACC ACC GAC GGT GTT CTG AAC GCG CCC GGT GCT CCG           2288
Phe Pro Ile Ile Thr Thr Asp Gly Val Leu Asn Ala Pro Gly Ala Pro
410                 415                 420

CAC CCG TTC CAT CTC CAC GGC GTAAGTCCTT GCTTTCCTCA GTGCCTCGCT              2339
His Pro Phe His Leu His Gly
425                 430

TCCACGACGT CCACTGATCC CACACATCCC ATGTGCAG CAC ACC TTC TCG GTG             2392
                                          His Thr Phe Ser Val
                                                          435

GTG CGC AGC GCC GGG AGC TCG ACC TTC AAC TAC GCC AAC CCA GTC CGC           2440
Val Arg Ser Ala Gly Ser Ser Thr Phe Asn Tyr Ala Asn Pro Val Arg
            440                 445                 450

CGG GAC ACC GTC AGT ACT GGT AAC TCT GGC GAC AAC GTC ACT ATC CGC           2488
Arg Asp Thr Val Ser Thr Gly Asn Ser Gly Asp Asn Val Thr Ile Arg
        455                 460                 465

TTC ACG GTACGTCTTC TCCGGAGCCC TCCCACCCGT GTGTCCGCTG AGCGCTGAAC            2544
Phe Thr
470

ACCGCCCACC GTGCTGCTGC TGCGCAG ACC GAC AAC CCA GGC CCG TGG TTC             2595
                            Thr Asp Asn Pro Gly Pro Trp Phe
                                            475

CTC CAC TGC CAC ATC GAC TTC CAC CTG GAG GCC GGC TTC GCC ATC GTC           2643
Leu His Cys His Ile Asp Phe His Leu Glu Ala Gly Phe Ala Ile Val
        480                 485                 490

TGG GGG GAG GAC ACT GCG GAC ACC GCG TCC GCG AAT CCC GTT CCT               2688
Trp Gly Glu Asp Thr Ala Asp Thr Ala Ser Ala Asn Pro Val Pro
495                 500                 505

GTACGTCGTG CCTGCTGAGC TCTTTGTGCC CGAACAGGGT GCTGATCGTG CCTTCCTCCG         2748

TGCAG ACG GCG TGG AGC GAT TTG TGC CCC ACT TAC GAT GCT TTG GAC TCG         2798
```

```
              Thr  Ala  Trp  Ser  Asp  Leu  Cys  Pro  Thr  Tyr  Asp  Ala  Leu  Asp  Ser
              510                      515                      520

TCC GAC CTC TGATCGACAA GGCATGAAGG CTGAAGCAGC TGCGGTCAAT                              2847
Ser Asp Leu
525

TCTCGAACAC ACTTTACTCG AACATTCATT TTTCTTTGGC TCGGGATCGG AACAAATCAT                    2907

GGGGGGGCCG GACCGTCT                                                                 2925
```

( 2 ) INFORMATION FOR SEQ ID NO:10:

( i ) SEQUENCE CHARACTERISTICS:
        ( A ) LENGTH: 527 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Polyporus pinsitus ( x i ) SEQUENCE DESCRIPTION: SEQ ID NO: 10:

```
Met  Gly  Lys  Tyr  His  Ser  Phe  Val  Asn  Val  Val  Ala  Leu  Ser  Leu  Ser
1                   5                        10                      15

Leu  Ser  Gly  Arg  Val  Phe  Gly  Ala  Ile  Gly  Pro  Val  Thr  Asp  Leu  Thr
               20                       25                      30

Ile  Ser  Asn  Ala  Asp  Val  Thr  Pro  Asp  Gly  Ile  Thr  Arg  Ala  Ala  Val
          35                       40                      45

Leu  Ala  Gly  Gly  Val  Phe  Pro  Gly  Pro  Leu  Ile  Thr  Gly  Asn  Lys  Gly
     50                       55                      60

Asp  Glu  Phe  Gln  Ile  Asn  Val  Ile  Asp  Asn  Leu  Thr  Asn  Glu  Thr  Met
65                       70                      75                      80

Leu  Lys  Ser  Thr  Thr  Ile  His  Trp  His  Gly  Ile  Phe  Gln  Ala  Gly  Thr
                    85                       90                      95

Asn  Trp  Ala  Asp  Gly  Ala  Ala  Phe  Val  Asn  Gln  Cys  Pro  Ile  Ala  Thr
               100                      105                     110

Gly  Asn  Ser  Phe  Leu  Tyr  Asp  Phe  Thr  Val  Pro  Asp  Gln  Ala  Gly  Thr
          115                      120                     125

Phe  Trp  Tyr  His  Ser  His  Leu  Ser  Thr  Gln  Tyr  Cys  Asp  Gly  Leu  Arg
     130                      135                     140

Gly  Pro  Leu  Val  Val  Tyr  Asp  Pro  Asp  Asp  Pro  Asn  Ala  Ser  Leu  Tyr
145                      150                     155                     160

Asp  Val  Asp  Asp  Asp  Thr  Thr  Val  Ile  Thr  Leu  Ala  Asp  Trp  Tyr  His
               165                      170                     175

Thr  Ala  Ala  Lys  Leu  Gly  Pro  Ala  Phe  Pro  Ala  Gly  Pro  Asp  Ser  Val
          180                      185                     190

Leu  Ile  Asn  Gly  Leu  Gly  Arg  Phe  Ser  Gly  Asp  Gly  Gly  Ala  Thr
     195                      200                     205

Asn  Leu  Thr  Val  Ile  Thr  Val  Thr  Gln  Gly  Lys  Arg  Tyr  Arg  Phe  Arg
     210                      215                     220

Leu  Val  Ser  Ile  Ser  Cys  Asp  Pro  Asn  Phe  Thr  Phe  Ser  Ile  Asp  Gly
225                      230                     235                     240

His  Asn  Met  Thr  Ile  Ile  Glu  Val  Asp  Gly  Val  Asn  His  Glu  Ala  Leu
                    245                      250                     255

Asp  Val  Asp  Ser  Ile  Gln  Ile  Phe  Ala  Gly  Gln  Arg  Tyr  Ser  Phe  Ile
               260                      265                     270

Leu  Asn  Ala  Asn  Gln  Ser  Ile  Asp  Asn  Tyr  Trp  Ile  Arg  Ala  Ile  Pro
          275                      280                     285
```

| | | | | | | | | | | | | | | |
|---|---|---|---|---|---|---|---|---|---|---|---|---|---|---|
| Asn | Thr 290 | Gly | Thr | Thr | Asp | Thr 295 | Thr | Gly | Gly | Val | Asn 300 | Ser | Ala | Ile | Leu |
| Arg 305 | Tyr | Asp | Thr | Ala | Glu 310 | Asp | Ile | Glu | Pro | Thr 315 | Thr | Asn | Ala | Thr | Thr 320 |
| Ser | Val | Ile | Pro | Leu 325 | Thr | Glu | Thr | Asp | Leu 330 | Val | Pro | Leu | Asp | Asn 335 | Pro |
| Ala | Ala | Pro | Gly 340 | Asp | Pro | Gln | Val | Gly 345 | Gly | Val | Asp | Leu | Ala 350 | Met | Ser |
| Leu | Asp | Phe 355 | Ser | Phe | Asn | Gly | Ser 360 | Asn | Phe | Phe | Ile | Asn 365 | Asn | Glu | Thr |
| Phe | Val 370 | Pro | Pro | Thr | Val | Pro 375 | Val | Leu | Leu | Gln | Ile 380 | Leu | Ser | Gly | Ala |
| Gln 385 | Asp | Ala | Ala | Ser | Leu 390 | Leu | Pro | Asn | Gly | Ser 395 | Val | Tyr | Thr | Leu | Pro 400 |
| Ser | Asn | Ser | Thr | Ile 405 | Glu | Ile | Ser | Phe | Pro 410 | Ile | Ile | Thr | Thr | Asp 415 | Gly |
| Val | Leu | Asn | Ala 420 | Pro | Gly | Ala | Pro | His 425 | Pro | Phe | His | Leu | His 430 | Gly | His |
| Thr | Phe | Ser 435 | Val | Val | Arg | Ser | Ala 440 | Gly | Ser | Ser | Thr | Phe 445 | Asn | Tyr | Ala |
| Asn | Pro 450 | Val | Arg | Arg | Asp | Thr 455 | Val | Ser | Thr | Gly | Asn 460 | Ser | Gly | Asp | Asn |
| Val 465 | Thr | Ile | Arg | Phe | Thr 470 | Thr | Asp | Asn | Pro | Gly 475 | Pro | Trp | Phe | Leu | His 480 |
| Cys | His | Ile | Asp | Phe 485 | His | Leu | Glu | Ala | Gly 490 | Phe | Ala | Ile | Val | Trp 495 | Gly |
| Glu | Asp | Thr | Ala 500 | Asp | Thr | Ala | Ser | Ala 505 | Asn | Pro | Val | Pro | Thr 510 | Ala | Trp |
| Ser | Asp | Leu 515 | Cys | Pro | Thr | Tyr | Asp 520 | Ala | Leu | Asp | Ser | Ser 525 | Asp | Leu | |

PURIFIED POLYPORUS LACCASES AND NUCLEIC ACIDS ENCODING SAME

This application is a continuation-in-part of application Ser. No. 08/265,534, filed Jun. 24, 1994 now abandoned, the contents of which are incorporated herein by reference.

SUMMARY OF THE INVENTION

The present invention relates to isolated nucleic acid fragments encoding a fungal oxidoreductase enzyme and the purified enzymes produced thereby. More particularly, the invention relates to nucleic acid fragments encoding a phenol oxidase, specifically a laccase, of a basidiomycete, Polyporus.

BACKGROUND OF THE INVENTION

Laccases (benzenediol:oxygen oxidoreductases) are multi-copper-containing enzymes that catalyze the oxidation of phenolics. Laccase-mediated oxidations result in the production of aryloxy-radical intermediates from suitable phenolic substrate; the ultimate coupling of the intermediates so produced provides a combination of dimeric, oligomeric, and polymeric reaction products. Such reactions are important in nature in biosynthetic pathways which lead to the formation of melanin, alkaloids, toxins, lignins, and humic acids. Laccases are produced by a wide variety of fungi, including ascomycetes such as Aspergillus, Neurospora, and Podospora, the deuteromycete Botrytis, and basidiomycetes such as Collybia, Fomes, Lentinus, Pleurotus, Trametes, Polyporus and perfect forms of Rhizoctonia. Laccases exhibit a wide range of substrate specificity, and each different fungal laccase usually differs only quantitatively from others in its ability to ozidize phenolic substrates. Because of the substrate diversity, laccases generally have found many potential industrial applications. Among these are lignin modification, paper strengthening, dye transfer inhibition in detergents, phenol polymerization, juice manufacture, phenol resin production, and waste water treatment.

Although the catalytic capabilities are similar, laccases made by different fungal species do have different temperature and pH optima, and these may also differ depending on the specific substrate. A number of these fungal laccases have been isolated, and the genes for several of these have been cloned. For example, Choi et al. (Mol. Plant-Microbe Interactions 5: 119–128, 1992) describe the molecular characterization and cloning of the gene encoding the laccase of the chestnut blight fungus, *Cryphonectria parasitica*. Kojima et al. (J. Biol. Chem. 265: 15224–15230, 1990; JP 2-238885) provide a description of two allelic forms of the laccase of the white-rot basidiomycete *Coriolus hirsutus*. Germann and Lerch (Experientia 41: 801,1985; PNAS U. S. A. 83: 8854–8858, 1986) have reported the cloning and partial sequencing of the *Neurospora crassa* laccase gene. Saloheimo et al. (J. Gen. Microbiol. 137: 1537–1544, 1985; WO 92/01046) have disclosed a structural analysis of the laccase gene from the fungus *Phlebia radiata*.

Attempts to express laccase genes in heterologous fungal systems frequently give very low yields (Kojima et al. , supra; Saloheimo et al. , Bio/Technol. 9: 987–990, 1991). For example, heterologous expression of *Phlebia radiata* laccase in *Trichoderma reesei* gave only 20 mg per liter of active enzyme in lab-scale fermentation (Saloheimo, 1991, supra). Although laccases have great commercial potential, the ability to express the enzyme in significant quantities is critical to their commercial utility. Previous attempts to express basidiomycete laccases in recombinant hosts have resulted in very low yields. The present invention now provides novel basidiomycete laccases which are well expressed in Aspergiflus.

SUMMARY OF THE INVENTION

The present invention relates to a DNA construct containing a nucleic acid sequence encoding a Polyporus laccase. The invention also relates to an isolated laccase encoded by the nucleic acid sequence. Preferably, the laccase is substantially pure. By "substantially pure" is meant a laccase which is essentially (i. e. , $\geq$90%) free of other non-laccase proteins.

In order to facilitate production of the novel laccase, the invention also provides vectors and host cells comprising the claimed nucleic acid sequence, which vectors and host cells are useful in recombinant production of the laccase. The sequence is operably linked to transcription and translation signals capable of directing expression of the laccase protein in the host cell of choice. A preferred host cell is a fungal cell, most preferably of the genus Aspergillus. Recombinant production of the laccase of the invention is achieved by culturing a host cell transformed or transfected with the construct of the invention, or progeny thereof, under conditions suitable for expression of the laccase protein, and recovering the laccase protein from the culture.

The laccases of the present invention are useful in a number of industrial processes in which oxidation of phenolics is required. These processes include lignin manipulation, juice manufacture, phenol polymerization and phenol resin production.

BRIEF DESCRIPTION OF THE FIGURES

FIG. 1 shows the DNA sequence and translation of genomic clone 21GEN, containing LCC1 (SEQ ID NO. 1)

FIG. 2 shows the DNA sequence and translation of genomic clone 23GEN, containing LCC2 (SEQ ID NO. 3)

FIG. 3 shows the DNA sequence and translation of genomic clone 24GEN, containing LCC3 (SEQ ID NO. 5)

FIG. 4 shows the DNA sequence and translation of genomic clone 31GEN, containing LCC4 (SEQ ID NO. 7)

FIG. 5 shows the DNA sequence and translation of genomic clone 41GEN, containing LCC5 (SEQ ID NO. 9)

FIG. 14 illustrates the light fastness of hair dyed with laccase vs. $H_2O_2$.

DETAILED DESCRIPTION OF THE INVENTION

Figure 6:
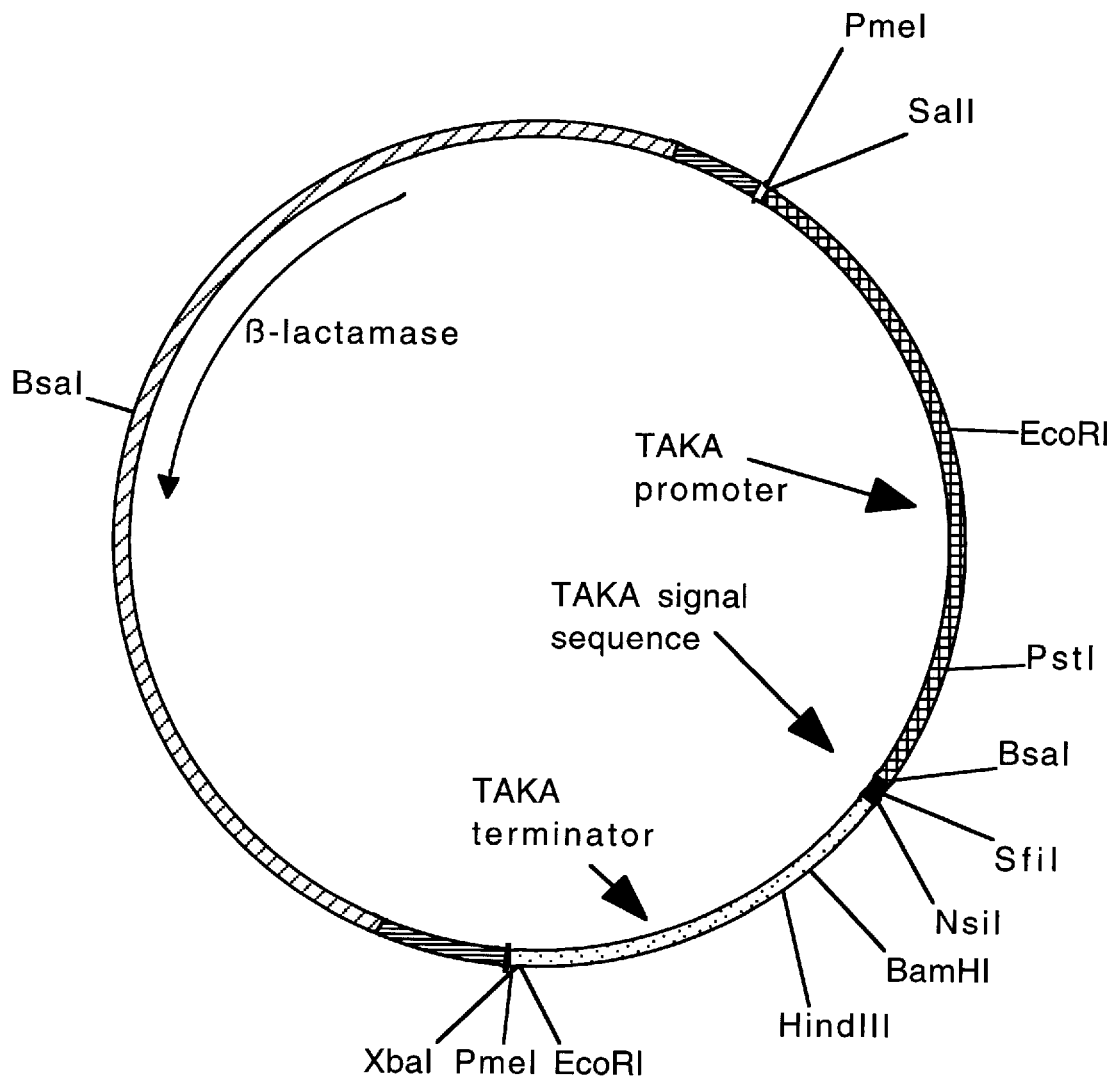
FIG. 6 shows the structure of vector pMWR1

*Polyporus pinsitus* is a basidiomycete, also referred to as *Trametes villosa*. Polyporus species have previously been identified as laccase producers (Fahraeus and Lindeberg, Physiol. Plant. 6: 150–158, 1953). However, there has been no previous description of a purified laccase from *Polyporus pinsitus*. It has now been determined that *Polyporus pinsitus* produces at least two different laccases, and the genes encoding these laccases can be used to produce relatively large yields of the enzyme in convenient host systems such as Aspergillus. In addition, three other genes which appear to code for laccases have also been isolated.

Initial screenings of a variety of fungal strains indicate that *Polyporus pinisitus* is a laccase producer. The production of laccase by *P. pinsitus* is induced by 2,5-xylidine. Attempts are first initiated to isolate the laccase from the supernatant of the induced strains. Anion exchange chromatography identifies an approximately 65 kD(on SDS-PAGE) protein which exhibits laccase activity. The enzyme is purified sufficiently to provide several internal peptide sequences, as well as an N-terminal sequence. The initial sequence information indicates the laccase has significant homology to that of *Coriolus hirsutus*, as well as to an unidentified basidiomycete laccase (Coll et al. , Appl. Environ. Microbiol. 59: 4129–4135, 1993. Based on the sequence information, PCR primers are designed and PCR carried out on cDNA isolated from *P. pinsitus*. A band of the expected size is obtained by PCR, and the isolated fragment linked to a cellulase signal sequence is shown to express an active laccase in *A. oryzae*, but at low levels. One of the PCR fragments is also used as a probe in screening a *P. pinsitus* cDNA library. In this manner, more than 100 positive clones are identified. The positive clones are characterized and the ends of the longest clones sequenced; none of the clones are found to be full-length.

Further attempts to isolate a full length clone are made. A 5–6 kb BamHI size-selected *P. pinsitus* genomic library is probed with the most complete cDNA fragment isolated as described above. Initial screening identifies one clone 24GEN(LCC3) having homology to the cDNA, but which is not the cDNA-encoded laccase and also not full length.

Subsequent screening of a 7–8 kb BamHI/EcoRi size-selected library indicates the presence of at least two laccases; partial sequencing shows that one, called 21GEN (LCC1), is identical to the original partial CDNA clone isolated, and the second, called 31GEN(LCC4) is a new, previously unidentified laccase. Secondary screenings of an EMBL4 genomic bank with LCC1 as probe identifies a class of clone containing the entire LCC1 insert as well as the 5' and 3' flanking regions. Screening of the EMBL bank with LCC3 identifies two additional clones encoding laccases which had not previously been identified, 41GEN(LCC5) and 23GEN(LCC2) and which differed structurally from the other three clones LCC1, LCC3, and LCC4. The nucleic acid and predicted amino acid sequences of each of the laccases is presented in FIGS. 1–5, and in SEQ ID NOS. 1–10. A comparison of the structural organization of each of the laccases is presented in Table 3. The laccases are generally optimally active at acid pH, between about 4–5. 5.

LCC1 is used to create expression vectors, which are in turn used to transform various species of Aspergillus. Transformation is successful in all species tested, although expression levels are highest in *Aspergillus niger*. Shake flask cultures are capable of producing 15 or more mg/liter of laccase, and in lab-scale fermentors, yields of over 300 mg/liter are observed. This is a significant improvement over laccase levels observed previously with other laccases and other fungal host cells.

According to the invention, a Polyporus gene encoding a laccase can be obtained by methods described above, or any alternative methods known in the art, using the information provided herein. The gene can be expressed, in active form, using an expression vector. A useful expression vector contains an element that permits stable integration of the vector into the host cell genome or autonomous replication of the vector in a host cell independent of the genome of the host cell, and preferably one or more phenotypic markers which permit easy selection of transformed host cells. The expression vector may also include control sequences encoding a promoter, ribosome binding site, translation initiation signal, and, optionally, a repressor gene or various activator genes. To permit the secretion of the expressed protein, nucleotides encoding a signal sequence may be inserted prior to the coding sequence of the gene. For expression under the direction of control sequences, a laccase gene to be used according to the invention is operably linked to the control sequences in the proper reading frame. Promoter sequences that can be incorporated into plasmid vectors, and which can direct the transcription of the laccase gene, include but are not limited to the prokaryotic β-lactamase promoter (Villa-Kamaroff, et al. , 1978, Proc. Natl. Acad. Sci. U. S. A. 75:3727–3731) and the tac promoter (DeBoer, et al. , 1983, Proc. Natl. Acad. Sci. U. S. A. 80:21–25). Further references can also be found in "Useful proteins from recombinant bacteria" in Scientific American, 1980, 242:74–94; and in Sambrook et al. , Molecular Cloning, 1989.

The expression vector carrying the DNA construct of the invention may be any vector which may conveniently be subjected to recombinant DNA procedures, and the choice of vector will typically depend on the host cell into which it is to be introduced. Thus, the vector may be an autonomously replicating vector, i. e. a vector which exists as an extrachromosomal entity, the replication of which is independent of chromosomal replication, e. g. a plasmid, or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the laccase DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA construct of the invention, especially in a bacterial host, are the promoter of the lac operon of *E. coli*, the *Streptomyces coelicolor* agarase gene dagA promoters, the promoters of the *Bacillus licheniformis* (α-amylase gene (amyL), the promoters of the *Bacillus stearothermophilus* maltogenic amylase gene (amyM), the promoters of the *Bacillus amyloliquefaciens* α-amylase (amyQ), or the promoters of the *Bacillus subtilis* xylA and xylB genes. In a yeast host, a useful promoter is the eno-1 promoter. For transcription in a fungal host, examples of useful promoters are those derived from the gene encoding *A. oryzae* TAKA amylase, *Rhizomucor miehei* aspartic proteinase, *A. niger* neutral α-amylase, *A. niger* acid stable (α-amylase, *A. niger* or *A. awamori* glucoamylase (glaA), *Rhizomucor miehei* lipase, *A. oryzae* alkaline protease, *A. oryzae* triose phosphate isomerase or *A. nidulans* acetamidase. Preferred are the TAKA-amylase and glaA promoters.

The expression vector of the invention may also comprise a suitable transcription terminator and, in eukaryotes, polyadenylation sequences operably connected to the DNA sequence encoding the laccase of the invention. Termination and polyadenylation sequences may suitably be derived from the same sources as the promoter. The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e. g. a gene the product of which complements a defect in the host cell, such as the dal genes from *B. subtilis* or *B. licheniformis*, or one which confers antibiotic resistance such as ampicillin, kanamycin, chloramphenicol or tetracycline resistance. Examples of Aspergillus selection markers include amdS, pyrG, argB, niaD, sC, trpc and hygB, a marker giving rise to hygromycin resistance. Preferred for use in an Aspergillus host cell are the amds and pyrG markers of *A. nidulans* or *A. oxyzae*. A frequently used mammalian marker is the dihydrofolate reductase (DHFR) gene. Furthermore, selection may be accomplished by co-transformation, e. g. as described in WO 91/17243.

It is generally preferred that the expression gives rise to a product which is extracellular. The laccases of the present invention may thus comprise a preregion permitting secretion of the expressed protein into the culture medium. If desirable, this preregion may be native to the laccase of the invention or substituted with a different preregion or signal sequence, conveniently accomplished by substitution of the DNA sequences encoding the respective preregions. For example, the preregion may be derived from a glucoamylase or an amylase gene from an Aspergillus species, an amylase gene from a Bacillus species, a lipase or proteinase gene from *Rhizomucor miehei*, the gene for the α-factor from *Saccharomyces cerevisiae* or the calf preprochymosin gene. Particularly preferred, when the host is a fungal cell, is the signal sequence for *A. oryzae* TAKA amylase, *A. niger* neutral amylase, the *Rhizomucor miehei* aspartic proteinase signal, the *Rhizomucor miehei* lipase signal, the maltogenic amylase from Bacillus NCIB 11837, *B. stearothermophilus* α-amylase, or *B. licheniformis* subtilisin.

The procedures used to ligate the DNA construct of the invention, the promoter, terminator and other elements, respectively, and to insert them into suitable vectors containing the information necessary for replication, are well known to persons skil led in the art (cf. , for instance, Sambrook et al. Molecular Cloning, 1989).

The cell of the invention either comprising a DNA construct or an expression vector of the invention as defined above is advantageously used as a host cell in the recombinant production of a enzyme of the invention. The cell may be transformed with th e DNA construct of the invention, conveniently by integrating the DNA construct in the host chromosome. This integration is generally considered to be an advantage as the DNA sequence is more likely to be stably maintained in the cell. Integration of the DNA constructs into the host chromosome may be performed according to conventional methods, e. g. by homologous or heterologous recombination. Alternatively, the cell may be transformed with an expression vector as described above in connection with the different types of host cells.

The host cell may be selected from prokaryotic cells, such as bacterial cells. Examples of suitable bacteria are gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis*, or *Streptomyces lividans* or *Streptomyces murinus*, or gram negative bacteria such as *E. coli*. The transformation of the bacteria may for instance be effected by protoplast transformation or by using competent cells in a manner known per se.

The host cell may also be a eukaryote, such as mammalian cells, insect cells, plant cells or preferably fungal cells, including yeast and filamentous fungi. For example, useful mammalian cells include CHO or COS cells. A yeast host cell may be selected from a species of Saccharomyces or Schizosaccharomyces, e. g. *Saccharomyces cerevisiae*. Useful filamentous fungi may be selected from a species of Aspergillus, e. g. *Aspergillus oryzae* or *Aspergillus niger*. Alternatively, a strain of a Fusarium species, e. g. *F. oxysporum*, can be used as a host cell. Fungal cells may be transformed by a process involving protoplast formation and transformation of the protoplasts followed by regeneration of the cell wall in a manner known per se. A suitable procedure for transformation of Aspergillus host cells is described in EP 238 023. A suitable method of transforming Fusarium species is described by Malardier et al. , 1989.

The present invention thus provides a method of producing a recombinant laccase of the invention, which method comprises cultivating a host cell as described above under conditions conducive to the production of the enzyme and recovering the enzyme from the cells and/or culture medium. The medium used to cultivate the cells may be any conventional medium suitable for growing the host cell in question and obtaining expression of the laccase of the invention. Suitable media are available from commercial suppliers or may be prepared according to published formulae (e. g. in catalogues of the American Type Culture Collection).

In a preferred embodiment, the recombinant production of laccase in culture is achieved in the presence of an excess amount of copper. Although trace metals added to the culture medium typically contain a small amount of copper, experiments conducted in connection with the present invention show that addition of a copper supplement to the medium can increase the yield of active enzyme many-fold. Preferably, the copper is added to the medium in soluble form, preferably in the form of a soluble copper salt, such as copper chloride, copper sulfate, or copper acetate. The final concentration of copper in the medium should be in the range of from 0. 2–2 mM, and preferably in the range of from 0. 05–0. 5 mM. This method can be used in enhancing the yield of any recombinantly produced fungal laccase, as well as other copper-containing enzymes, in particular oxidoreductases.

The resulting enzyme may be recovered from the medium by conventional procedures including separating the cells from the medium by centrifugation or filtration, precipitating the proteinaceous components of the supernatant or filtrate by means of a salt, e. g. ammonium sulphate, followed by purification by a variety of chromatographic procedures, e. g. ion exchange chromatography, gel filtration chromatography, affinity chromatography, or the like. Preferably, the isolated protein is about 90% pure as determined by SDS-PAGE, purity being most important in food, juice or detergent applications.

In a particularly preferred embodiment, the expression of laccase is achieved in a fungal host cell, such as Aspergillus. As described in detail in the following examples, the laccase gene is ligated into a plasmid containing the *Aspergillus oryzae* TAKA α-amylase promoter, and the *Aspergillus nidulans* amdS selectable marker. Alternatively, the amdS may be on a separate plasmid and used in co-transformation.

The plasmid (or plasmids) is used to transform an Aspergillus species host cell, such as *A. oryzae* or *A. niger* in accordance with methods described in Yelton et al. (PNAS U. S. A. 81: 1470–1474, 1984).

It is of particular note that the yields of Polyporus laccase in the present invention, using Aspergillus as host cell are unexpectedly and considerably higher than has previously been reported for expression of other laccases in other host cells. It is expected that the use of Aspergillus as a host cell in production of laccases from other basidiomycetes, such as Coriolus or Trametes, will also produce larger quantities of the enzyme than have been previously obtainable. The present invention therefore also encompasses the production of such Polyporus-like laccases in Aspergillus recombinant host cells.

Those skilled in the art will recognize that the invention is not limited to use of the nucleic acid fragments specifically disclosed herein, for example, in FIGS. 1–5. It will also be apparent that the invention encompasses those nucleotide sequences that encode the same amino acid sequences as depicted in FIG. 1–5, but which differ from the specifically depicted nucleotide sequences by virtue of the degeneracy of the genetic code. Also, reference to FIGS. 1–5 in the specification and the claims will be understood to encompass both the genomic sequence depicted therein as well as the corresponding cDNA and RNA sequences, and the phrases "DNA construct" and "nucleic acid sequences" as used herein will be understood to encompass all such variations. "DNA construct" shall generally be understood to mean a DNA molecule, either single- or double-stranded, which may be isolated in partial form from a naturally occurring gene or which has been modified to contain segments of DNA which are combined and juxtaposed in a manner which would not otherwise exist in nature.

In addition, the invention also encompasses other Polyporus laccases, including alternate forms of laccase which may be found in *Polyporus pinsitus* and as well as laccases which may be found in other fungi falling within the definition of Polyporus as defined by Fries, or synonyms thereof as stated in Long et al. , 1994, ATCC Names of Industrial Fungi, ATCC, Rockville, Md. Identification and isolation of laccase genes from sources other than those specifically exemplified herein can be achieved by utilization of the methodology described in the present examples, with publicly available Polyporus strains. Alternately, the sequence disclosed herein can be used to design primers and/or probes useful in isolating laccase genes by standard PCR or southern hybridization techniques. Other named Polyporus species include, but are not limited to, *P. zonatus, P. alveolaris, P. arcularius, P. australiensis, P. badius, P. biformis, P. brumalis, P. ciliatus, P. colensoi, P. eucalyptorum, P. meridionalis, P. varius, P. palustris, P. rhizophilus, P. rugulosus, P. squamosus, P. tuberaster*, and *P. tumulosus*. Also encompassed are laccases which are synonyms, e. g. , anamorphs or perfect states of species or strains of the genus Polyporus. Strains of Polyporus are readily accessible to the public in a number of culture collections, such as the American Type Culture Collection (ATCC), e. g. , ATCC 26721, 9385, 11088, 22084, Deutsche Sammlung von Mikroorganismen und Zellkulturen GmbH (DSM),e. g. , DSM 1021, 1023, and 1182; and Centraalbureau Voor Schimmelcultures (CBS), e. g. , CBS 678. 70, 166. 29, 101. 15, 276. 31, 307. 39, 334. 49, and 332. 49. The invention also encompasses any variant nucleotide sequence, and the protein encoded thereby, which protein retains at least about an 80% homology, preferably at least about 85%, and most preferably at least about 90–95% homology with any one of the amino acid sequences depicted in FIGS. 2–5, and which qualitatively retains the laccase activity of the sequence described herein. Useful variants within the categories defined above include, for example, ones in which conservative amino acid substitutions have been made, which substitutions do not significantly affect the activity of the protein. By conservative substitution is meant that amino acids of the same class may be substituted by any other of that class. For example, the nonpolar aliphatic residues Ala, Val, Leu, and Ile may be interchanged, as may be the basic residues Lys and Arg, or the acidic residues Asp and Glu. Similarly, Ser and Thr are conservative substitutions for each other, as are Asn and Gln. It will be apparent to the skilled artisan that such substitutions can be made outside the regions critical to the function of the molecule and still result in an active enzyme. Retention of the desired activity can readily be determined by conducting a standard ABTS oxidation method, such as is described in the present examples.

The protein can be used in number of different industrial processes. These processes include polymerization of lignin, both Kraft and lignosulfates, in solution, in order to produce a lignin with a higher molecular weight. Such methods are described in, for example, Jin et al. , Holzforschung 45(6): 467–468, 1991; U. S. Pat. No. 4,432,921; EP 0 275 544; PCT/DK93/00217, 1992.

The laccase of the present invention can also be used for in-situ depolymerization of lignin in Kraft pulp, thereby producing a pulp with lower lignin content. This use of laccase is an improvement over the current use of chlorine for depolymerization of lignin, which leads to the production of chlorinated aromatic compounds, which are an environmentally undesirable by-product of paper mills. Such uses are described in, for example, Current opinion in Biotechnology 3: 261–266, 1992; J. Biotechnol. 25: 333–339, 1992; Hiroi et al. , Svensk papperstidning 5: 162–166, 1976.

Oxidation of dyes or dye precursors and other chromophoric compounds leads to decolorization of the compounds. Laccase can be used for this purpose, which can be particularly advantageous in a situation in which a dye transfer between fabrics is undesirable, e. g. , in the textile industry and in the detergent industry. Methods for dye transfer inhibition and dye oxidation can be found in WO 92/01406, WO 92/18683, EP 0495836 and Calvo, Mededelingen van de Faculteit Landbouw-wetenschappen/ Rijiksuniversitet Gent. 56: 1565–1567, 1991; Tsujino et al. , J. Soc. Chem. 42: 273–282, 1991.

The laccase is particularly well-suited for use in hair dyeing. In such an application, the laccase is contacted with a dye precursor, preferably on the hair, whereby a controlled oxidation of the dye precursor is achieved to convert the precursor to a dye, or pigment producing compound, such as a quinoid compound. The dye precursor is preferably an aromatic compound belonging to one of three major chemical families: the diamines, aminophenols(or aminonaphthols) and the phenols. The dye precursors can be used alone or in combination. At least one of the intermediates in the copolymerization must be an ortho- or para-diamine or aminophenol(primary intermediate). Examples of such are found in Section V, below, and are also described in U. S. Pat. No. 3,251,742, the contents of which are incorporated herein by reference. In one embodiment, the starting materials include not only the enzyme and a primary intermediate, but also a modifier (coupler) (or combination of modifiers), which modifier is typically a meta-diamine, meta-aminophenol, or a polyphenol. The modifier then reacts with the primary intermediate in the presence of the laccase, converting it to a colored compound. In another embodiment, the laccase can be used with the primary intermediate directly, to oxidize it into a colored compound. In all cases, the dyeing process can be conducted with one or more primary intermediates, either alone or in combination with one or more modifiers. Amounts of components are in accordance with usual commericial amounts for similar components, and proportions of components may be varied accordingly.

The use of this laccase is an improvement over the more traditional use of $H_2O_2$, in that the latter can damage the hair, and its use usually requires a high pH, which is also damaging to the hair. In contrast, the reaction with laccase can be conducted at alkaline, neutral or even acidic pH, and the oxygen needed for oxidation comes from the air, rather than via harsh chemical oxidation. The result provided by the use of the Polyporus laccase is comparable to that achieved with use of $H_2O_2$, not only in color development, but also in wash stability and light fastness. An additional commercial advantage is that a single container package can be made containing both the laccase and the precursor, in an oxygen free atmosphere, which arrangement is not possible with the use of $H_2O_2$.

The present laccase can also be used for the polymerization of phenolic or aniline compounds present in liquids. An example of such utility is the treatment of juices, such as apple juice, so that the laccase will accelerate a precipitation of the phenolic compounds present in the juice, thereby producing a more stable juice. Such applications have been described in Stutz, Fruit processing 7/93, 248–252, 1993; Maier et al. , Dt. Lebensmittel-rindschau 86(5): 137–142, 1990; Dietrich et al. , Fluss. Obst 57(2): 67–73, 1990.

Laccases such as the Polyporus laccase are also useful in soil detoxification (Nannipieri et al. , J. Environ. Qual. 20: 510–517,1991; Dec and Bollag, Arch. Environ. Contam. Toxicol. 19: 543–550, 1990).

The invention is further illustrated by the following non-limiting examples.

EXAMPLES

I. Isolation of a *Polyporus Pinisitus* Laccase Enzyme Materials and Methods 1. Enzymatic Assays Unless otherwise stated, throughout the examples, laccase activity is determined by syringaldazine and 2,2,'-bisazino (3-ethylbenzthiazoline-6-sulfonic acid)(ABTS), as follows. The oxidation of syringaldazine is monitored at 530 nm with 19 $\mu$M substrate. In 25 mM sodium acetate, 40 $\mu$M cupric sulfate, pH 5. 5, at 30° C. , the activity is expressed as LACU($\mu$mole/min). For pH profile studies, Britton & Robinson (B & R) buffers are used, and are prepared according to the protocol described in Quelle, Biochemisches Taschenbuch, H. M. Raven, II. Teil, S. 93 u. 102, 1964. ABTS oxidation is carried out with 1 mM ABTS in 0. 1M NaAc, pH 5. 0 at room temperature by monitoring either $\Delta Abs_{405}$ in a 96-well plate(Costar) or $\Delta Abs_{418}$ in a quartz cuvette. The overlay ABTS oxidase activity assay is carried out by pouring cooled ABTS-agarose(0. 03–0. 1 g ABTS, 1 g agarose, 50 ml $H_2O$, heated to dissolve agarose) over a native IEF gel or PAGE and incubating at room temperature.

2. Initial Isolation of laccase

In order to isolate the laccase, 800 ml of culture fluid is filtered by HFSC on a Supra filter(slow filtering). The clear filtrate is then concentrated and washed on an Amicon cell with a GR81 PP membrane to a volume of 72 ml.

One ml aliquots of laccase are bound to a Q-sepharose HP(Pharmacia, Sweden) column, equilibrated with 0. 1M phosphate, pH7 and the laccase is eluted with a NaCl gradient. In all, 10×1 ml samples are purified, pooled, concentrated and washed by ultrafiltration using a membrane with a molecular weight cut-off of 6 kD.

3. Secondary Purification

In a second purification, a fermentation broth is filtered and concentrated by ultrafiltration. The starting material contains 187 LACU/ml. The concentrate is quick-filtered on a Propex 23 filter(P & S Filtration), with 3% Hyflo Cuper-Cel (HSC; Celite Corporation), followed by two ultrafiltration on a Filtron filter with two membranes, each with a molecular weight cutof of 3 kD. The resulting sample (2. 5 mS/cm, pH 7. 0, at 4° C. ) is applied to a 130 ml Q-Sepharose column, equilibrated with sodium phosphate, 1. 1 mS/cm, pH 7. 0. Under these conditions the laccase does not bind to the column, but elutes slowly from the column during the application and wash with the equilibration buffer, resulting in a partial separation from other brownish material.

This partially purified preparation of 1. 0 mS, pH 7. 0 at 20° C. is applied to a Q-sepharose column. The column is equilibrated with 20 mM sodium phosphate, 2. 2 mS, pH 7. 0. Under these conditions, the laccase binds to the column and is eluted by a gradient of 0–1M NaCl over 20 column volumes.

3. Sequencing

For internal peptide sequencing, the purified protein is digested with trypsin, followed by peptide purification with HPLC. Purified peptides are sequenced in an Applied Biosystems 473A sequencer.

B. Results and Discussion

1. Initial Characterization

Total yield of the initial purification is about 50 mg(estimated at A280 nm). The purified enzyme has a rich blue color, and appears as only two very close bands on SDS-PAGE at about 65 kd. A native PAGE overlaid with substrate shows that both bands have laccase activity with ABTS. The absorption spectrum shows that besides an absorption at A280 nm, the purified laccase also shows absorption at about 600 nm.

2. Sequencing

A N-terminal determination of the protein initially purified shows a single sequence:

Gly-Ile-Gly-Pro-Val-Ala-Asp-Leu-Thr-Ile-Thr-Asn-Ala-Ala-Ala-Val-Ser-Pro-Asp-Gly-Phe-Pro . . .

Since the N-terminal sequence is not the ideal sequence for constructing a probe, additional experiments with a trypsin digest are conducted, followed by further purification (described above) and sequencing of fragments 2. Secondary Purification and Characterization In the second purification, the second Q-Sepharose chromatographic step yields the following pools:

Q-Sepharose-2-pool-1 40 ml 112 LACU 47 LACU/$A_{280}$
Q-Sepharose-2-pool-3 80 ml 385 LACU 65 LACU/$A_{280}$ The elution yields >80% of the applied amount. The highly purified preparation Q-Sepharose-2-pool-3 has an $A_{280}$=5. 9, and $A_{280}/A_{260}$=1. 4. The purity of the laccase in the starting material is extremely high on a protein basis but the starting material is a very dark brown color. In SDS-PAGE, a double band is seen, with a dominating 65 kD band and a smaller 62 kD band. By anionic chromatography, only the dominating band is seen in the first peak(Q-Sepharose-2-pool-1), whereas both bands are seen in the second peak(Q-Sepharose-2-pool-3).

3. Sequence

A number of internal peptide sequences are determined, and compared with the *Coriolus hirsutus*(Ch) laccase sequence. The identified fragments are as follows:

Tryp 13:
Ser—Pro—Ser—Thr—Thr—Thr—Ala—Ala—Asp—Leu
Tryp 14:
Ser—Ala—Gly—Ser—Thr—Val—Tyr—Asn—Tyr—Asp—Asn—Pro—Ile—Phe Arg
Tryp 16:
Sequence 1:
Ser—Thr—Ser—Ile—His—Trp—His—Gly—Phe—Phe—Gln—Lys
Sequence 2:
Gly—Ile—Gly—Pro—Val—Ala—Asp—Leu—Thr—Ile—Thr—Asn—Ala—Ala—Val
Tryp 18:
Gly—Ile—Gly—Pro—Val—Ala—Asp—Leu—Thr—Ile—Thr—Asn
Tryp 19:
Sequence 1:
Leu—Gly—Pro—Ala—Phe—Pro—Leu—Gly—Ala—Asp—Ala—Thr—Leu—Ile—
Sequence 2:
Phe—Gln—Leu—Asn—Val—Ile—Asp—Asn—Asn—Thr—Thr—His—Thr—Met
Tryp 25:
Tyr—Ser—Phe—Val—Leu—Glu—Ala—Asn—Gln—Ala—Val—Asp—Asn—Tyr—Trp—Ile—Arg
Tryp 27
Gly—Thr—Asn—Trp—Ala—Asp—Gly—Pro—Ala—Phe

II. Isolation of a *Polyporus Pinisitus* Laccase CDNA Clone

A. Materials and Methods

1. RNA Preparation

RNA is isolated from 10 grams of *P. pinsitus* mycelium grown under xylidine induction for 6.5 hours, using the guanidium/CsCl cushion method. The RNA is poly-A selected on an oligo-dT column, using standard conditions. 120 μg mRNA is obtained and stored as lyophilized pellet in 5 μg aliquots at −80° C.

2. Single Stranded cDNA

Single stranded cDNA is synthesized using the reverse transcriptase "Super Script" (BRL) according to manufacturer's directions.

3. Construction of cDNA Library

A cDNA library is constructed using the librarian IV cDNA kit (Invitrogen). Fifty cDNA pools, each containing approximately 5000 individual transformants, are obtained.

4. PCR

PCR is conducted under the following standard conditions: 100 pmol of each primer, 10 μl 10× PCR buffer (Perkin-Elmer), 40 μl dNTP 0.5 mM, 2 μl single stranded cDNA(or approximately 100 ng chromosomal DNA or 100 ng PCR fragment), H$_2$O to 100 μl, 2.5 U Taq polymerase. The cycles are 3×(40° C./two minutes, 72° C./two minutes, 94° C./one minute) followed by 30×(60° C./two minutes, 72° C./two minutes, 94° C./1 minute).

B. Results and Discussion

1. Cloning of *Polyporus pinsitus* laccase

PCR is carried out with the primer #3331:
ACCAGNCTAGACACGGGNTC/AGATACTG/ ACGNGAGAGCGGAC/TTGCTGGTC ACTATCTTC-GAAGATCTCG
and primer #3332:
CGCGGCCGCTAGGATCCTCACAATGGCCAA/ CTCTCTG/CCTCG/ACCTTC.
A clear band of about 1500 bp is obtained. The DNA is digested with NotI/HindIII, and fractionated on an agarose gel. The upper band(fragment #42) is purified and cloned into the Aspergillus vector pHD423. No transformants are obtained. Several attempts are carried out in order to clone the fragment, including redigestion with the restriction enzymes, phosphorylation of the ends, filling in with klenow and blunt-end cloning in SmaI cut puC18, without success. Hybridization with a laccase probe based on the laccase described in Coll et al., supra, indicates that the PCR product could be the *P. pinsitus* laccase. In a new attempt to clone the PCR fragment, a new PCR reaction is carried out, using the same conditions as for fragment #42. Again the result is a fragment of about 1500 bp(fragment #43). This time the fragment is cut with HindIII/BamHI, and ligated to HindIII/BamHI-cut pUC18. Three clones, #43-/A,-B,-G are found to contain a fragment of 1500 bp. Partial sequencing reveals that these fragments are laccase related.

2. Expression of *Polyporus pinsicus* laccase

To express the laccase, the fragment #43 is joined to a signal sequence from a 43kD cellulase. The primer pHD433 (TAGCGGATCCCACAATGCGTTCCTCCCCCCTCCTC-CCGTCCGCCGTTGTGGCCGCCCTGCCGGTGTT-GGCCCTTGCCGGCATTGGGCCCGTCGCGGACC) is used in a standard PCR reaction with a pUC forward primer (New England Biolabs). All three clones are used as templates in order to minimize the risk of working with DNA containing errors.

The PCR generated DNA from the reaction with a primer pHD433 and template 43-A and 43-G is cut with HindIII/ BamHI and cloned into the Aspergillus expression vector pHD414 (described in detail below). Several transformants are obtained.

Clones pHD433/43A-1,2, pHD433/43G-2,-3 are transformed into *A. oryzae*. The transformants from each transformation (between 3–10) are analyzed for laccase production. Activity is only obtained with pHD433/43G-3. The positive transformants (numbers 1, 4, 6) are reisolated on amdS plates, and retested. In an additional transformation round a further ten transformants are obtained with pHD433/ 43G-3. The clones #20, 23, 26, 28, and 29 are positive. The clones are reisolated and two single isolates are analyzed for laccase expression semiquantitatively by color development in an ABTS assay at pH 4.5. On a scale of +−+++, several clones show moderate to strong expression of laccase.

Further cloning is conducted to identify a full length clone. A xylidine-induced cDNA library consisting of approximately 350,000 transformants is screened using fragment #42-4 as a probe. More than 100 positive clones are detected. The clones are purified, rescreened, and analyzed on Southern blots. Two of the longest clones are further, characterized by DNA sequence determination. The longest clones are found to be identical and found to contain a poly-A stretch in the 3' end and to start at the amino acid number 4 in the amino terminus. A partial DNA sequence is determined from different clones.

pHD423/43G-3 is then used in further cloning studies as described in the following Section IV.

III. Purification and Characterization of Additional Polyporus Pinsitus Laccase Wild-Type Enzymes A. Materials and Methods 1. Culture Conditions Shake flasks(250 ml medium/2. 8 l baffled flask) are inoculated with several agar plugs taken from a week-old PDA plate of P. pinsitus. The medium contains, per liter, 10 g glucose, 2. 5 g L-asparagine, 0. 2 g L-phenylalanine, 2. 0 g yeast extract, 2. 0 g $KH_2PO_4$, 0. 5 g $MgSO_4 \cdot 7H_2O$, 2. 0 mlAMG trace metals, 0. 002 g $CuSO_4 \cdot 7H_2O$, 1. 0 g citric acid, made with tape water, pH 5. 0 before autoclaving. The cultures are grown at 18°–22° C. on a rotary shaker with low agitiation (~100 rpm). After 7 days, the pH of each shake flask is adjusted to ~6. 0 by the addition of 0. 25 ml 5N NaOH and the cultures are induced by adding 0. 5 ml of a 2,5-xylidine stock solution(xylidine diluted 1:10 into ethanol) to each flask. Flasks are incubated for an additional 24 hours, at which time the culture supernatant from each flask is recovered.

2. Materials

Chemicals used as buffers are commercial products of at least reagent grade. Endo/N-glucosidase F is from Boehringer-Mannheim. Chromatography is performed on Pharmacia FPLC. Spectroscopic assays are conducted on either a spectrophotometer(Shimadzu PC160) or a microplate reader(Molecular Devices).

3. Purification

Culture broth is filtered first on cheesecloth and centrifuged at 1000× g to remove gelatinous pinkish xylidine polymer. The supernatant is then filtered on Whatman #2 paper and concentrated from 1500 to 250 ml on S1Y100 (Amicon, Spiral concentrator) at 4° C. The concentrated broth is diluted with water until it reaches 0. 8 mS(from 2. 5 mS) and then concentrated on S1Y100 to 250 ml. The washed broth, thawed from −20° C. freezing overnight, is subjected to Whatman #2 paper filtration to remove residual pinkish material, and then pH adjusted by NaOH from pH 6. 1 to pH 7. 7. This yellowish broth, 275 ml with 0. 8 mS, is applied on a Q-Sepharose XK-26 column(~64 ml gel) equilibrated with 10 mM Tris-HCl, pH 7,7, 0. 7 mS. The first active laccase fraction runs through during loading and washing by the equilibrating buffer. The elution is carried out by a linear gradient of 0–0. 5M NaCl in the equilibrating buffer over 8. 8 bed-volume. The second and third active fractions are eluted around 0. 15 and 0. 35M NaCl, respectively. No more active fractions are detected when the column is washed sequentially with 2M NaCl and with 1 mM NaOH. The active fractions are pooled, adjusted to ~10 mS, concentrated on Centricon-10(Amicon), and then applied onto Superdex 75(HR10/30, 24 ml, Pharmacia) equilibrated with 10 mM Tris-HCl, 0. 15M NaCl, pH 8, 14 mS. During elution with the application buffer, laccase fractions are eluted off using the same elution volume for all three Q-Sepharose fractions, indicating very similar native molecular weight. The purity of the laccase is tested on SDS-PAGE.

4. Protein Analysis

PAGE and native IEF are carried out on a Mini Protean II and a Model 111 Mini IEF cells(Bio-Rad). Western blots are carried out on a Mini trans-blot cell(Bio-Rad) with an alkaline phosphatase assay kit(Bio-Rad). The primary antibodies are diluted 1000-fold during blotting. N-terminus sequencing is performed on an Applied Biosystems (ABI) 476A protein sequencer using liquid phase TFA delivery for cleavage and on-line HPLC for identification of PTH-amino acids. Standard Fast Cycles and Pre-Mix Buffer System is used according to manufacturer's instructions. Deglycosylation with glycosidase is done as follows: 3 µg of protein and 3. 6 units of glycosidase in 0. 25M NaAc, pH 5, 20 mM EDTA, 0. 05% 2-mercaptoethanol is incubated at 37° C. for 18 hours with ovalbumin and bovine serum albumin serving as positive and negative control, respectively, and the mobility is detected by SDS-PAGE.

Amino acid analysis for determining extinction coefficients is done using Amino Quant 1090 HPLC system from Hewlett Packard. Microwave facilitated vapor phase hydrolysis of lyophilized samples is done using the MDS-2000 hydrolysis-station(CEM, Matthews, N. C. ). 6N HCl containing 1% phenol as a scavenger is used to create the acid vapors. Hydrolysis time is 20 minutes at 70 psi (~148° C. ). Hydrolyzed samples are lyophilized and redissolved in 20 µl of 500 pmol/µl sarcosine and norvaline as internal standards. 1 µl is injected and analyzed according to manufacturer's instructions.

B. Results and Discussion

1. Purification

The previously characterized P. pinsitus laccase has a pI of ~3. 5. However, considerable laccase activity is detected in the run-through fraction of Q-Sepharose pre-equilibrated at pH 7. 7. Upon a gradient elution, one more active fraction comes off the column before the active fraction initially anticipated. UV-visible spectra and SDS-PAGE show that all three fractions contain mainly laccase. After further purification by gel filtration, different pI's under native non-denaturing conditions are detected for the two new fractions and shown to be consistent with the elution order.

2. Characterization

The pure laccase preparations derived from Q-Sepharose eluates behave as a rather well-defined band on SDS-PAGE at ~63 kDa. Deglycosylation detects ~14% w/w carbohydrates based on mobility change on SDS-PAGE. On native-IEF, the laccase preparations have bands of pI 6–6. 5, 5–6. 5, and 3. 5. ABTS-agarose overlay show that all bands are active. Each form in turn shows multiple isoforms under the IEF conditions.

The neutral and acidic forms have a typical UV-visible spectrum with maxima at 605 and 275 nm. The ratio of $A_{275}/A_{605}$ is 30–40. The spectrum for the acidic-neutral form has a peak at 276 nm and a shoulder around 600 nm.

The N-terminal sequencing shows that the neutral and neutral-acidic forms have the same first 29 residues(Table 1). The N-terminus of the acidic form matches 100% to that of the previously characterized form. All three forms exhibit comparable cross-reactivity toward antibodies raised against previously characterized form.

TABLE 1

Structural and enzymatic properties of *P. pinsitus* laccases

| Form | N-terminus | LACU | $\Delta A_{405}$ min-1 (ABTS) |
|---|---|---|---|
| Acidic | GIGPVA D LTITNAAVSPDGFSRQAVVVNG | 92 | 4000 |
| Acidic-Neutral | A*****(*)*VVAP****L*D*I**** | 75 | 4000 |
| Neutral | A*****(*)*VVAP****L*D*I**** | 32 | 1000 |

*Same residue as compared with the acidic form. ( ): weak signal

3. Laccase Activity

The specific activities(per $A_{275}$) of the three forms are tested by both ABTS and syringaldazine oxidations. The shapes and optima of the pH activity profiles for the three forms are very close: all have optima at $\leq$pH4 and pH 5–5. 5 for ABTS and syringaldazine oxidations, respectively.

IV. Isolation of Multiple Copies of *Polyporus Pinsitus* Laccase Enzymes and Genes A. Materials and Methods 1. Strains The following strains are employed in the methods described below: *E. coli* K802(e14-(mrca), mcrB, hsdR2, galK2, galT22, supE44, metB1; Clonetech); *E. coli* XL-1 Blue (recA1, endA1, gyrA96, thi-1, hsdR17, supE44, relA1, lac[F'proAB, lacIqZDM15, Tn10(tet$^r$)];Stratagene) and *Polyporus pinsitus* CBS 678. 70.

2, Genomic DNA Isolation

Cultures of *P. pinsitus* are grown in 500 ml YG (0. 5% yeast extract, 2% dextrose) at room temperature for 3 to 4 days. Mycelia are harvested through miracloth, washed twice with TE and frozen quickly in liquid nitrogen. The frozen mycelia are stored at −80° C. To isolate DNA, the mycelia are ground to a fine powder in an electric coffee grinder. The powdered mycelia are resuspended in TE to a final volume of 22 ml. Four ml 20% SDS is added with mixing by inversion followed by incubation at room temperature for 10 minutes. The sample is gently extracted with phenol:chloroform and centrifuged to separate the phases. The aqueous phase is collected and 400 µl proteinase A(10 mg/ml stock) is added. The sample is incubated at 37° C. for 30 minutes followed by a phenol:chloroform extraction. The aqueous phase is precipitated by the addition of 0. 1 volumes of 3M Na acetate, pH 5. 2 and 2. 5 volumes 95% ethanol and freezing at 20° C. for one hour. After centrifugation to precipitate the DNA, the pellet is resuspended in 6 ml TE, and 200 µl boiled RNase A(10 mg. ml stock) is added. After incubation at 37° C. , 100 µl proteinase A(10 mg/ml stock) is added followed by incubation at 37° C. for 30 minutes. The sample is phenol:chloroform extracted twice. To the aqueous phase, 0. 1 volumes 3M Na acetate and 2. 5 volumes are added, and teh sample is frozen at −20° C. for 1 hour. Following centrifugation, the pellet is gently resuspended in 400 µl TE, and 40 µl Na acetate and 1 ml 95% ethanol are added. The DNA is pelleted by centrifugation, and the pellet is washed in 70% ethanol. The final pellet is resuspended in 250 µl TE.

3. RNA Preparation

RNA is isolated from mycelia which are harvested from *P. pinisitus* cultures which are either induced for laccase expression by the addition of 2,5-xylidine or are uninduced. The mycelia are washed and frozen quickly in liquid $N_2$. Frozen mycelia are ground to a fine powder in an electric coffee grinder. The powder is immediately suspended in 20 ml extraction buffer (0. 2M Tris-HCl, 0. 25M NaCl, 50 mM EGTA, 0. 8% tri-isopropyl naphthalene sulfonic acids, 4. 8% p-aminosalicylic acid, pH 8. 5). All solutions for RNA extraction are made with diethylpyrocarbonate(DEP)-treated water. The sample is kept on ice and 0. 5 volumes TE-saturated phenol:chloroform is added. The sample is mixed well by inversion for 2 minutes, and the phases are separated by centrifugation. The aqueous phase is saved, and the organic phase is extracted with 2 ml extraction buffer and incubated at 68° C. for 5 minutes. After centrifugation to separate the phases, the aqueous phases are pooled and extracted several time with phenol:chloroform until there is no longer any protein at the interface. To the aqueous phase 0. 1 volume 3M Na-acetate, pH 5. 2 and 2. 5 volumes 95% ethanol are added to precipitate the RNA, and the sample is frozen at −20° C. for 2 hours. The RNA is pelleted and resuspended in DEP water with RNase inhibitor.

4, DNA Sequencing

Nucleotide sequences are determined using TAQ polymerase cycle sequencing with fluorescent-labeled nucleotides, and reactions are electrophoresed on an Applied Biosystems automatic DNA sequencer(Model 363A, version 1. 2. 0).

5. Preparation of Genomic Libraries

Two size-selected genomic libraries of *P. pinsitus* are constructed. A library of 5 to 6 kb BamHI fragments are constructed in pBluescript+. Genomic DNA is digested with BamHI, and the digest is electrophoresed on a preparative agarose(IBI) gel. The region containing the 5 to 6 BamHI fragments is sliced from the gel. The DNA is isolated from teh gel using a Geneclean kit(BIO 101). The DNA is ligated into pBluescript plasmid previously digested with BamHI and dephosphorylated with BAP(GIBCO BRL), *E. coli* XL-1 Blue competent cells (Stratagene) are transformed with the ligation, and 12,000 white colonies are obtained.

A library of 7 to 8 kb BamHI/EcoRI fragments is constructed in pUC118. Ten µg genomic DNA is digested with BamHI and EcoRI and treated with BAP(GIBCO BRL). Competent *E. Coli* XL-1 Blue cells are transformed with the ligation, and the library contains ~8000 recombinants.

For the preparation of a total genomic library in lambda EMBL4, 25 µg of *P. pinsitus* genomic DNA is partially digested with Sau3A. After digestion, the DNA is electrophoresed on a preparative low-melt agarose gel, and a band containing the 9 to 23 kb sized DNA is sliced from the gel. The DNA is extracted from the gel using β-agarose(New England Biolabs). The isolated EMBL4 arms (Clonetech) according to the supplier's directions. The ligation is packaged in vitro using a Gigapack II kit(Stratagene). The library is titered using *E. coli* K802 cells. The unamplified library is estimated to contain 35,000 independent recombinants. The library is amplified using *E. coli* K802 cells.

6. Southern and Northern Blots

DNA samples are electrophoresed on agarose gels in TAE buffer using standard protocols. RNA samples are electrophoresed on agarose gels containing formaldehyde. Both DNA and RNA gels are transferred to Zeta-Probe membrane (BIO-RAD) using either capillary action under alkaline conditions or a vacuum blotter. After transfer, the DNA gels are UV crosslinked. Blots are prehybridized at 65° C. in 1. 5× SSPE, 1% SDS, 0. 5% non-fat dried milk and 200 μg/ml salmon sperm DNA for 1 hour. Radioactive probes are added directly to the prehybridization solutions, and hybridizations are continued overnight at 65° C. Blots are washed with 2×SSC for 5 minutes at 65° C. and with 0. 2×SSC, 1% SDS, 0. 1% Na-pyrophosphate at 65° C. for 30 minutes twice.

Radioactive labeled probes are prepared using a α-$^{32}$P-dCTP and a nick translation kit(GIBCO-BRL).

7. Library Screening

For screening of the size-selected 5–6 kb BamHI and 7–8 kb BamHI/EcoRI libraries ~500 colonies on LB carb plates and lifted the colonies to Hybond N+ filters(Amersham) using standard procedures. The filters are UV crosslinked following neutralization. The filters are prehybridized at 65° C. in 1,5× SSPE, 1% SDS, 0. 5% non-fat dried milk, 200 μg/ml salmon sperm DNA for 1 hour. Nick-translated probes are added directly to the prehybridization solution, and hybridizations are done overnight at 65° C.

For screening of the genomic bank in EMBL, appropriate dilutions of the amplified library are plated with *E. coli* K802 cells on 100 mM NZY top agarose. The plaques are lifted to Hybond N+ membranes(Amersham) using standard procedures. The DNA is crosslinked to the membranes using UV crosslinking. The filters are prehybridized and hybridized using the same conditions as those mentioned above.

Results and Discussion

1. Isolation of Multiple Copies of Laccase Gene

*P. pinsitus* genomic DNA is Digested with several different restriction enzymes for southern analysis. The blot is probed with the cDNA insert(isolated as a BamHI/SphI fragment from the pYES vector) which is labeled with α-P$^{32}$-dCTP. The blot is hybridized and washed as described above. The cDNA hybridizes to several restriction fragments for most of the enzymes suggesting that there are multiple laccase genes in the genome. Because the cDNA hybridizes to a BamHI fragment of ~5. 5 kb, a library of 5–6 kb BamHI fragments from *P. pinsitus* is constructed.

2. Screening of Genomic Libraries

The results from screening of the libraries are summarized in Table 2. The 5–6 kb BamHI size-selected library is screened with the original cDNA clone labeled with $^{32}$P. Approximately 30,000 colonies are screened with hybridizations done at 65° C. Plasmid DNA is isolated from two positive colonies and digested with BamHI to check for insert size. Both clones contain an ~5. 5 kb BamHI insert. The cloned insert(LCC3) is sequenced from either end; the sequence has homology to the cDNA, but is clearly not the cDNA encoded laccase. The partial DNA sequence of LCC3 also indicates that the LCC3 pUC118 clone does not contain the full gene.

From a southern blot of BamHI/EcoRI double digested DNA it is demonstrated that the cDNA hybridizes to an ~7. 7 kb fragment. A size-selected library in pUC118 is constructed containing 7–8 BamHI/EcoRI fragments. A total of ~8000 independent colonies are obtained and screened by hybridization with a $^{32}$P labeled insert. Plasmid DNA is isolated from the positive colonies and digested with BamHI and EcoRI. Restriction analysis of the plasmids demonstrate that they fall into two classes. One class (LCC4) contains four clones which are all identical and have an ~7. 7 kb BamHI/EcoRI insert which hybridizes to the cDNA. A second class(LCC1) contains two clones which are identical and have inserts of ~7. 2 kb which hybridize to the cDNA.

Partial DNA sequencing of clones LCC1 and LCC4 demonstrate that clone 21 is the genomic clone of the original cDNA, while LCC4 codes for another laccase. The partial DNA sequence of LCC1 shows that the pUC118 clone does not contain the full gene and that a fragment upstream of the EcORI site is needed.

At the same time the size selected 7–8 BamHI/EcoRI library is being constructed, a *P. pinisitus* genomic bank in EMBL4 is constructed containing ~35,000 independent recombinant phage. Ten positive plaques are picked and purified. DNA is isolated from the purified phage lysates. Restriction digests of EMBL DNAs demonstrates that there are three classes of clones. The first class(11GEN) is defined by two sibs whose inserts contain a BamHI/EcoRI fragment of the same size as LCC1 which hybridizes to the LCC1 insert. The second class(12GEN) contains one clone which has a different restriction pattern than the 11GEN class and whose insert contains a different restriction pattern than the 11GEN class and whose insert contains an ~5. 7 kb BamHI/EcoRI fragment. The third class is defined by a single clone whose insert contains an ~3. 2 kb BamHI/EcoRI fragment which hybridizes to the LCC1 insert. DNA sequence analysis demonstrates that clone 11GEN contains the LCCI BamHI/EcoRI fragment and both 5' and 3" flanking regions. It is also demonstrated that clone 12GEN contains a portion of the LCC1 insert.

The *P. pinisitus* EMBL genomic bank is also screened with the LCC3 BamHI insert in order to clone the full gene. Approximately 30,000 plaques are plated and lifted from hybridization. Five plaques which hybridize to the LCC3 (BamHI/EcoRI) insert are identified and purified. DNA is isolated from the purified phage stocks. Southern analysis of *P. pinisitus* genomic DNA demonstrates that the LCC3 BAmHI insert hybridizes to an ~7kb EcoRI fragment. Restriction digests and southerns demonstrate that 4 of the clones contain restriction fragments which hybridize to the EcoRI/BamHI(1. 6 kb) fragment and that the clones fall into three classes. Class one is defined by a single clone(LCC5) whose insert contains a 3 kb EcoRI fragment which hybridizes to the LCC3 BamHI/EcoRI fragment. Another class is defined by clone(LCC2) whose insert contains an ~11 kb EcoRI fragment which hybridizes to the LCC3 BamHI/EcoRI insert. The third class is defined by two clones which are not identical but contain many of the same restriction fragments; these clones both contain an ~7. 5 kb EcoRI fragment which hybridizes to the LCC3 insert. Further analysis of this third class indicates that they are identical to clone LCC4. Partial DNA sequencing of LCC5 and LCC2 indicates that both of these clones code for laccases; however, neither is identical to any of the above mentioned laccase genes(LCC1, LCC3, or LCC4). At this point, five unique laccase genes are cloned; however, the fragments subcloned from LCC5 and LCC2 do not contain the full genes.

From the DNA sequencing of the 3 kb EcoRI fragment from clone LCC5 it is determined that ~200 base pairs of the N-terminus are upstream of the EcORI site. A 380 bp EcoRI/MluI fragment from LCC5 is used to identify for subcloning a MluI fragment from the LCC5 EMBL clone. An ~4. 5 MluI fragment from the LCC5 EMBL clone is subcloned for sequencing and shown to contain the N-terminal sequence.

To clone the N-terminal half of the LCC3 laccase gene, the *P. pinisitus* EMBL genomic bank is probed with an ~750 bp BamHI/StuI restriction fragment from the LCC3 pUC118 clone. Approximately 25,000 plaques are screened and five plaques appear to hybridize with the probe. Upon further purification only three of the clones are still positive. Two of the clones give very strong signals and the restrictions digests of DNA isolated from these phage demonstrate that both contain an ~750 bp BamHI/StuI fragment in their inserts and that the two clones are not identical but overlapped. Based on results of Southern analysis, an ~8. 5 kb fragment from these clones are subcloned for sequencing. The EcoRI fragment is shown to contain the entire gene.

To clone the N-terminal half of the LCC2 laccase gene, the *P. pinsitus* genomic bank in EMBL4 is probed with an ~680 bp EcoRI/PvuI of the EMBL LCC2 clone. Thirty thousand plaques are screened by hybridization at 65° C. , and 15 plaques appear to hybridize with the probe. All fifteen are purified, and DNA is isolated. The clones can be placed in four classes based on restriction patterns, Seven of the clones are all sibs, and are identical to the original EMBL clone of LCC2. The second class is defined by 3 clones which are sibs. An ~4 kb HindIII fragment is subcloned from this class for sequencing and is shown to contain the N-terminal half of LCC2. A third class is defined by a single clone and is not characterized further.

3. DNA Sequencing

The complete DNA sequences of the five genomic clones is determined as described in Materials and Methods. Sequencing of clone LCC2 demonstrate that it probably codes for the second form of laccase(neutral pI) isolated from culture broth from an induced *P. pinsitus* culture as described above. The N-terminal protein sequence from the neutral pI laccase and the predicted N-terminus for the protein coded for by LCC2 are compared, and show identity. The predicted pI for the protein coded for by clone LCC2 is 5. 95, which is in good agreement with the experimental pI determined for the second form of laccase being between 5. 0 and 6. 5. FIGS. 1–5 (SEQ ID NOS. 1–5) show the DNA sequences and predicted translation products for the genomic clones. For LCC1, the N-terminus of the mature protein as determined by protein sequencing and predicted by Von Heijne rules is Gly at position 22. The N-terminus is Gly-Ile-Gly-Pro-Val-Ala-. For LCC2 the N-terminal amino acid of the mature protein as determined by protein sequencing is Ala at position 21. The N-terminus is Ala-Ile-Gly-Pro-Val-Ala-. For LCC3 the predicted N-terminal amino acid of the mature protein is Ser at position 22, with the N terminus being Ser-Ile-Gly-Pro-Val-Thr-Glu-Leu-. For LCC4, the predicted N-terminal amino acid is Ala at position 23 with the N-terminus being Ala-Ile-Gly-Pro-Val-Thr-. For LCC5 the predicted N-terminal amino acid is Ala at position 24 with the N-terminus being Ala-Ile-Gly-Pro-Val-Thr-Asp.

A comparison of the structural organization of the genes and the predicted proteins they code for is presented in Table 2. It will be seen that the five genes have different structural organizations and code for proteins of slightly different sizes. Comparisons between the predicted proteins of the genomic clones and other fungal laccase are also done. Table 3 shows a comparison of the predicted laccase to each other and to other fungal laccases. Clone LCC1(the induced laccase first characterized) has the most identity(90%) to the *Coriolus hirsutus* laccase and the PM1 basidiomycete laccase(Coll et al. , supra). The other four laccases have between 64 and 80% identity to the *C. hirsutus* laccase. The laccase coded for by LCC3 has the least identity to the LCC1 laccase and the other fungal laccases shown in Table 3. LCC2 appears to be the second wild-type laccase isolated as described above; based on the N-terminal sequences of the isolated clones, it also appears that the "neutral" and acidic neutral" wild-type laccases are the same enzyme which is encoded by the LCC2 sequence.

TABLE 2

Comparison of Structural Organization and Predicted Proteins of the *P. pinsitis* Genomic Clones.

| Gene | # Introns | Size of Predicted Precursor Protein | Size of Predicted Mature Protein | Predicted Isolelectric Point |
|---|---|---|---|---|
| 21GEN | 8 | 520 | 499 | 4.49 |
| 23GEN | 10 | 519 | 498 | 5.95 |
| 24GEN | 12 | 516 | 495 | 5.23 |
| 31GEN | 11 | 510 | 488 | 4.06 |
| 41GEN | 11 | 527 | 504 | 4.07 |

TABLE 3

Amino Acid Identity Between *P. pinsitis* Laccases and Other Fungal Laccases.

|  | 21GEN | 23GEN | 24GEN | 31GEN | 41GEN | CRIPHA | CRIPHE | PBILAC | PM1 |
|---|---|---|---|---|---|---|---|---|---|
| 21GEN | — | 79% | 64% | 70% | 72% | 90% | 91% | 64% | 80% |
| 23GEN | 79% | — | 65% | 66% | 69% | 80% | 81% | 62% | 74% |
| 24GEN | 64% | 65% | — | 61% | 65% | 64% | 65% | 61% | 63% |
| 31GEN | 70% | 66% | 61% | — | 75% | 69% | 70% | 64% | 69% |
| 41GEN | 72% | 69% | 65% | 75% | — | 71% | 72% | 64% | 71% |
| CRIPHA | 90% | 80% | 64% | 69% | 71% | — | 99% | 64% | 80% |
| CRIPHE | 91% | 81% | 65% | 70% | 72% | 99% | — | 65% | 81% |
| PBILAC | 64% | 62% | 61% | 64% | 64% | 64% | 65% | — | 65% |
| PM1 | 80% | 74% | 63% | 69% | 71% | 80% | 81% | 65% | — |

21GEN, 23GEN, 24GEN, 31GEN and 41GEN = *P. pinsitis* laccase clones
CRIPHA = *Coriolus hirsutis* laccase A
CRIPHE = *C. hirsutis* laccase B
PBILAC = *Phlebia radiata* laccase
PM1 = Basidiomycete PM1 laccase (CECT2971)

5. Northern Blots

RNA is isolated from mycelia from both a xylidine-induced culture and an uninduced culture. RNA is blotted to membrane after electrophoresis, and the blot is probed with the CDNA insert, or a small fragment containing ~100 bp of the 23GEN promoter and the first 100 bp of the coding region. A transcript of about 1. 8 kb hybridizes to both the induced and uninduced RNA samples; however, transcription of this message is clearly induced by the addition of xylidine to the culture.

III. EXPRESSION OF *P. PINSITUS* LACCASE IN ASPERGILLUS MATERIALS AND METHODS

1. Strains

*A. oryzae* A1560, *A. oryzae* HowB104(fungamyl delete, pyrg), *A. oryzae* HowB101pyrg, *A. niger* Bo-1, *A. niger* Bo-80, *A. niger* ATCC1040, *A. niger* NRRL337, *A. niger* NRRL326, *A. niger* NRRL326, *A. niger* NRRL2295, *A. niger* ATCC11358, *A. niger* NRRL322, *A. niger* AT10864, *A. japonicus* A1438, *A. phoenicis*, *A. foetidus* N953.

2. Media

For the shake flask cultivation of the *A. niger, A. foetidus*, and *A. phoenicis* MY50 (per liter: 50 g maltodextrin, 2 g $MgSO_4 \cdot H_2O$, 10 g $KH_2PO_4$, 2 g $K_2SO_4$, 2 g citric acid, 10 g yeast extract, 0. 5 ml trace metals, 2 g urea, pH 6. 0) media is used. For the shake flask cultivation of the *A. oryzae* A1560 and HowB101 strains MY51(per liter: 30 g maltodextrin, 2 mg $MgSO_4$, 10 g $KH_2PO_4$, 2 g $K_2SO_4$, 2 g citric acid, 10 g yeast extract, 0. 5 ml trace metals, 1 g urea, 2 g$(NH_4)_2SO_4$, pH 6. 0) is used. For the shake flask analysis of the *A. oryzae* HowB104 strains, MY51 maltose(same as MY51 but with 50 g of maltose instead of maltodextrin) media is used. For the shake flask analysis of the *A. japonicus* strains M400 media(per liter: 50 g maltodextrin, 2 g $MgSO_4$, 2 g $KH_2PO_4$, 4 g citric acid, 8 g yeast extract, 0. 5 ml trace metals, 2 g urea, pH 6. 0.

Cultures grown overnight for protoplast formation and subsequent transformation are grown in YEG(0. 5% yeast extract, 2% dextrose). For strains that are pyrg, uridine is supplemented to 10 mM final concentration.

3. Screening for Laccase Production

Primary transformants are screened first on a minimal medium plates containing 1% glucose as the carbon source and 1 mM ABTS to test for production of laccase. Transformants that give green zones on the plates are picked and spore purified before shake flask analysis is done.

Shake flask samples are centrifuged to clear the broth. Dilute or undiluted broth samples are assayed with ABTS Results and Discussion

1. Expression in Shake Flasks

Figure 7:
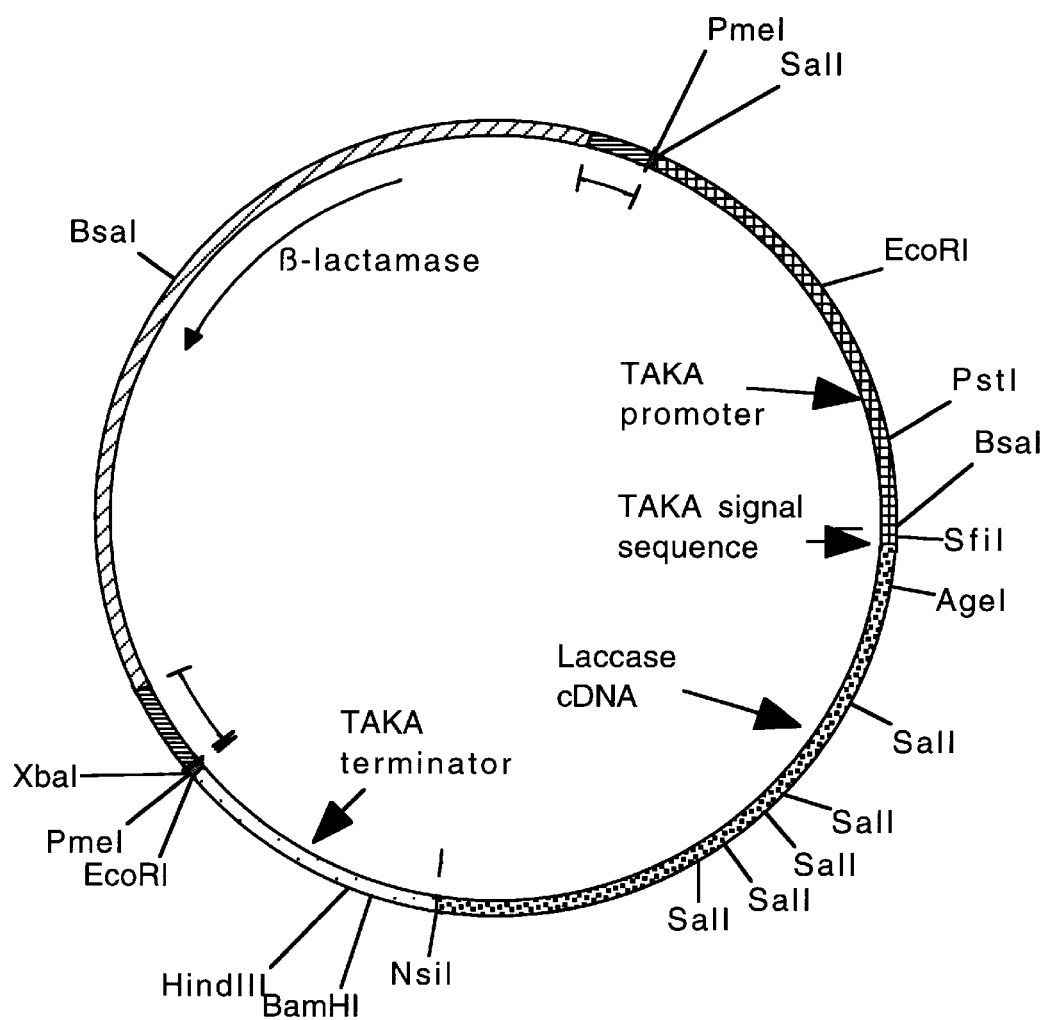
FIG. 7 shows the structure of vector pDSY1

The first expression vector constructed is pDSY1, which contains the TAKA promoter, TAKA signal sequence, *P. pinisitus* laccase cDNA beginning at the mature N-terminus and the AMG terminator. The TAKA signal sequence: laccase insert is constructed in 2 steps. First by site directed mutagenesis, an AgeI site beginning at bp 107 of the laccase mature coding region is created by a single base change and a NsiI site is created ~120 bp downstream of the laccase stop codon(ACG GGT→ACC GGT and TTC GCT→ATG CAT, respectively). A small PCR fragment beginning with an SfiI site and ending with the AgeI site at 107 bp in laccase is PCR amplified. This fragment contains a piece of the TAKA signal sequence and the first ~107 bp of the mature laccase cDNA. Further DNA sequencing of this fragment shows it has a single base change that leads to a substitution of Asn for Thr at position 9 in mature laccase. This substitution creates a potential N-linked glycosylation site. The PCR fragment and AgeI/NsiI fragments are cloned into pMWR1 (FIG. 6) which has been digested with SfiI/NsiI. The vector pMWRI contains the TAKA promoter, a portion of the TAKA signal sequence which ends with an SfiI site, and the TAKA terminator with a NsiI site inserted directly 5' to the terminator. The resulting expression vector (FIG. 7) is used to cotransform several hosts. Methods for co-transformation of Aspergillus strains are as described in Christensen et al. , supra.

In the second laccase expression vector, the base change in DSY1 which leads to the substitution of Asn for Thr at amino acid 9 is reverted back to wild type by a PCR reaction. The second expression vector pDSY2 is identical to PDSY1 except for this single base change. Three different *A. oryzae* strains and several *A. niger* strains are cotransformed with pDSY2 and either pTOC90(WO 91/17243) which carries the *A. nidulans* amds gene or pSO2 which carries the *A. oryzae* pyrG gene.

Expression of laccase is observed in all hosts tested, with both DSY1 and DSY2. Yields range from 0. 1–12. 0 Δabs/min/ml, with highest yields being observed with *A. niger* strains.

Figure 8:
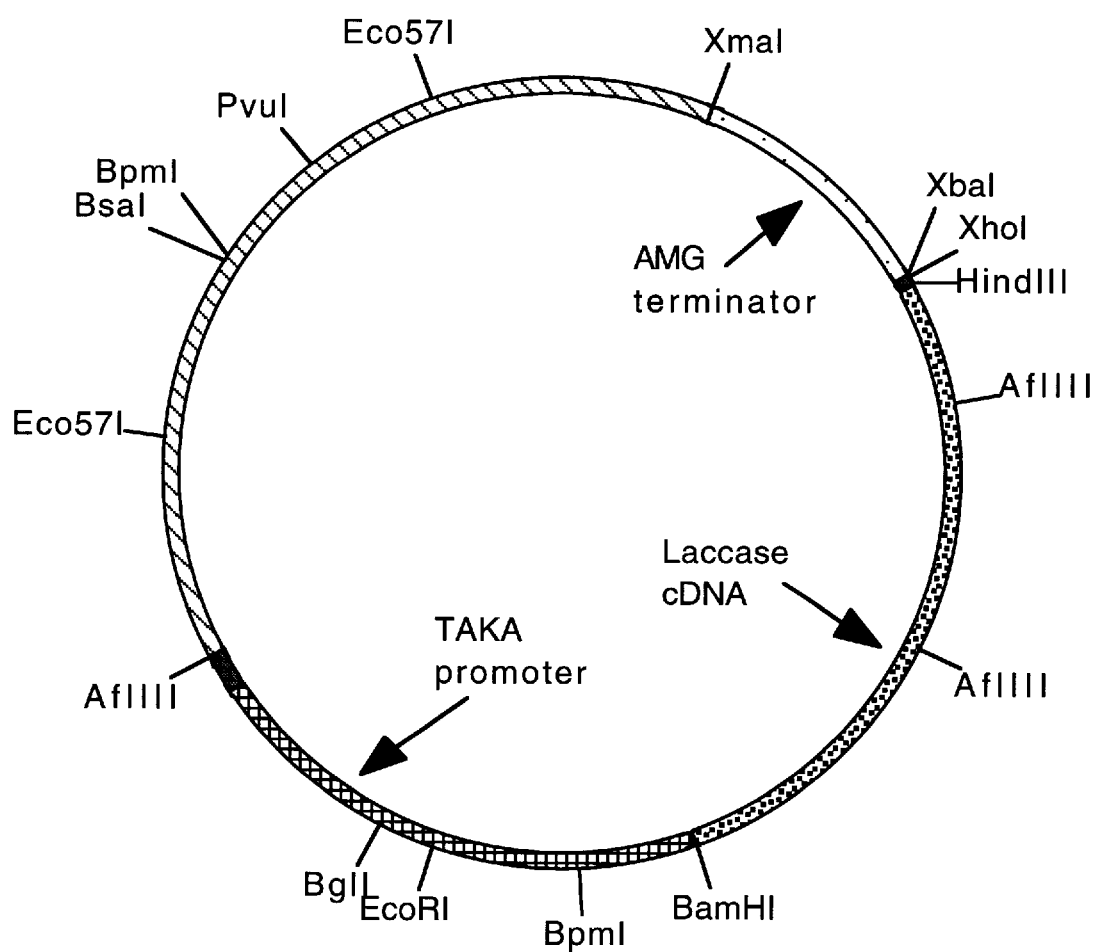
FIG. 8 shows the structure of vector pDSY10

A construct pDSY10 is made which contains the TAKA promoter, laccase full-length cDNA including its own signal sequence and the AMG terminator. A 200 bp BamHI/AgeI fragment which has a BamHI site immediately 5' to the ATG of the initiation codon and an AgeI site at the same position as in pDSY1 is PCR amplified using lacI as template. A MluI/HindIII fragment is PCR amplified using pDSY2 as template and begins with the MluI site present in the cDNA and ends with a HindII site directly 3' to the stop codon of laccase. The above two fragments and the AgeI/MluI fragment from pDSY2 are ligated into pHD414 to yield pDSY10 (FIG. 8).

The vector pHD414 used in expression of laccase is a derivative of the plasmid p775(EP 238 023). In contrast to this plasmid, pHD414 has a string of unique restriction sites between the TAKA promoter and the AMG terminator. The plasmid is constructed by removal of an approximately 200 bp long fragment (containing undesirable RE sites) at the 3' end of the terminator, and subsequent removal of an approximately 250 bp long fragment at the 5' end of the promoter, also containing undesirable sites. The 200 bp region is removed by cleavage with NarI (positioned in the pUC vector) and XbaI (just 3' to the terminator), subsequent filling in the generated ends with Klenow DNA polymerase+ dNTP, purification of the vector fragment on a gel and religation of the vector fragment. This plasmid is called pHD413. pHD413 is cut with StuI (positioned in the 5' end of the promoter) and PvuII (in the pUC vector), fractionated on gel-and religated, resulting in pHD414. Cotransformation of *A. oryzae* HowB104 and *A. niger* Bo-1 are done using pToC90 for selection. Yields in shake flask are comparable to those seen with pDSY2.

2. Expression in Fermentors

A 1 ml aliquot of a spore suspension of *Aspergillus niger* transformant Bo-1-pDSY10-4(approximately $10^9$ spores/ ml) is added aseptically to a 500 ml shake flask containing 100 ml of sterile shake flask medium (glucose, 75 g/l; soya meal, 20 g/l; $MgSO_4 \cdot 7H_2O$, 2 g/l; $KH_2PO_4$, 10 g/l; $K_2SO_4$, 2 g/l; $CaCl_2 \cdot 2H_2O$ 0. 5 g/l; Citric acid, 2 g/l; yeast extract, 10 g/l; trace metals[$ZnSO_4 \cdot 7H_2O$, 14. 3 g/l; $CuSO_4 \cdot 5H_2O$, 2. 5 g/l; $NiCl_2 \cdot 6H_2O$, 0. 5. g/l; $FeSO_4 \cdot 7H_2O$, 13. 8 g/l, $MnSO_4 \cdot H_2O$, 8. 5 g/l; citric acid, 3. 0 g/l], 0. 5 ml/l; urea, 2 g/l, made with tap water and adjusted to pH 6. 0 before autoclaving), and incubated at 37° C. on a rotary shaker at 200 rpm for 18 hours. 50 ml of this culture is aseptically transferred to a 3 liter fermentor containing 1. 8 liters of the fermentor media (maltodextrin MD01 300 g/l; $MgSO_4 \cdot 7H_2O$, 2 g/l; $KH_2PO_4$, 2 g/l; citric acid 2 g/l; $K_2SO_4$, 2. 7 g/l; $CaCl_2 \cdot 2H_2O$, 2 g/l; trace metals, 0. 5 ml/l; pluronic antifoam, 1 ml/l; made with tap water and pH adjusted to 6. 0 before autoclaving). The fermentor temperature is maintained at 34° C. by the circulation of cooling water through the fermentor jacket. Sterile air is sparged through the fermentor at a rate of 1. 8 liter/min (1 v/v/m). The agitation rate is maintained at 800 rpm for the first 24 hours after inoculation and at 1300 rpm for the remainder of the fermentation. The pH of the fermentation is kept at 4. 0 by the automatic addition of 5N NaOH or H₃PO4. Sterile feed (urea, 50 g/l; pluronic antifoam, 1. 5 ml/l, made up with distilled water and autoclaved) is added to the fermentor by use of a peristaltic pump. The feed rate profile during the fermentation is as follows: 40 g of feed is added initially before inoculation; after inoculation, feed is at a constant rate of 2. 5 g/l h.

Copper is made as a 400× stock in water or a suitable buffer, filter sterilized and added aseptically to the tank to a final level of 0. 5 mM. Samples for enzyme activity determination are withdrawn and filtered through Miracloth to remove mycelia. These samples are assayed for laccase activity by a LACU assay. Laccase activity is found to increase continuously during the course of the fermentation, with a value of approximately 55 LACU/ml is achieved after 190 hours. This corresponds to approximately 350 mg/l of recombinant laccase expressed.

IV. PURIFICATION OF RECOMBINANT LACCASE

Materials and Methods

1. Materials

Chemicals used as buffers and substrates are commercial products of at least reagent grade. Endo/N-glycosidase G is from Boehringer-Mannheim. Chromatography is performed on either a Pharmacia's FPLC or a conventional open column low pressure system. Spectroscopic assays are conducted on a Shimadzu PC160 spectrophotometer.

2. Purification (a) DSY2

2. 8 liters cheese-cloth filtered broth(pH 7, 19 mS) obtained from an A. oryzae pDSY2 transformant as described above is filtered on 0. 45 μ Corning filter and concentrated on Spiral Concentrator(Amicon) with S1Y30 membrane to 200 ml. The concentrate pH is adjusted to 7. 5, diluted with 4. 8 l water to achieve 1. 2 mS, and concentrated on S1Y30 to 200 ml. 50 ml of this broth solution is applied onto a Q-Sepharose column(XKI6, 34 ml gel), pre-equilibrated with 10 mM Tris, pH 7. 5, 0. 7 mS(Buffer A). The blue laccase band that migrates slowly during loading is eluted by a linear gradient of Buffer B(Buffer A plus 0. 5M NaCl). 24 ml of pooled laccase fractions are concentrated on Centricon-100(Amicon) to 4. 5 ml and-applied onto a Superdex 200 column(HiLoad 16/60, 120 ml gel). During the development with Buffer C(Buffer A plus 0. 15M NaCl, 14. 4 mS), the blue laccase fractions elute followed by brownish contaminant fractions. only the first half of the elution band(detected by Abs₆₀₀) show a high laccase to contaminant ratio and are pooled. The pooled fractions are dialyzed in 10 mM Bis-Tris, pH 6. 8, 0. 6 mS(Buffer D), applied onto a Mono-Q column(Mono-Q 5/5, 1 ml) equilibrated with Buffer D, and eluted with Buffer E(Bufer D plus 0. 5M NaCl) using a linear gradient. The laccase fractions, which ome out round 27% Buffer E, are pure as judged by SDS-PAGE. At each step, the laccase fractions are routinely checked by ABTS oxidation, SDS-PAGE, and Western Blot.

(b) DSY10

2. 8 liters cheese-cloth filtered broth(pH 7. 3, 24 mS) obtained from HowB104-pDSY10 is filtered on Whatman #2 paper and concentrated on Spiral Concentrator(Amicon) with S1Y100 membrane to 210 ml. The concentrate pH is diluted with water to achieve 1. 2 mS, and concentrated on S1Y100 to 328 ml. This broth solution is applied onto a Q-Sepharose column(XK26, 120 ml gel), pre-equilibrated with 10 mM Tris, pH 7. 5, 0. 7 mS(Buffer A). The blue laccase band that migrates slowly during loading is eluted by a linear gradient of Buffer B(Buffer A plus 2M NaCl). 120 ml of pooled laccase fractions are diluted with water to achieve 1. 1 mS and then concentrated on SIY100 to 294 ml and applied onto a Mono-Q column(HiLoad 16/10, 40 ml gel) pre-equilibrated with Buffer A. The laccase slowly passes through the column during loading and washing with Buffer A. The pooled fractions which have a pH reading of 5. 6, are loaded on a Mono-Q column(HiLoad 16/10, 40 ml gel), pre-equilibrated with Buffer C(10 mM MES, pH 5. 5, 0. 1 mS). The laccase fractions elute by a very shallow gradient of Buffer D(Buffer C+1M NaCl). Enzymatic assays are conducted as described above.

3. Protein Analysis

Total amino acid analysis, N-terminal sequencing, deglycosylation, SDS-PAGE, IEF, and Western blots are performed as decribed above.

B. Results and Discussion

1. Purification and Characterization

Overall a 256-fold purification and a yield of 37% are achieved for DSY10, and a 246-fold purification and a yield of 14% are achieved for DSY2 In terms of electorphoretic pattern, spectral properties and activity, purified DSY2 and DSYlO are indistinguishable. Purified recombinant laccases behave as a dimer on gel filtration, and exhibit subunit molecular weight which is somewhat larger than that of the wild type laccase, indicating a post-translational processing in A. oryzae that results in the extra glycosylation on the recombinants. Deglycosylation has confirmed the difference in mass arising from extra sugars(Table 4).

TABLE 4

Molecular and spectral properties of recombinant and wild-type laccase

| | MW, kDa | | Carbohydrate | | |
|---|---|---|---|---|---|
| | Native | subunit | w/w % | pI | $\lambda_{max}$, nm($\epsilon$, 1/g* cm) |
| WT | ~130 | ~63 | ~7 | 3.5 | 275(1.8)615(0.12) |
| Rec. | ~130 | ~67 | ~13 | 3.5 | 275(1.7)615(0.11) |

Figure 9A:
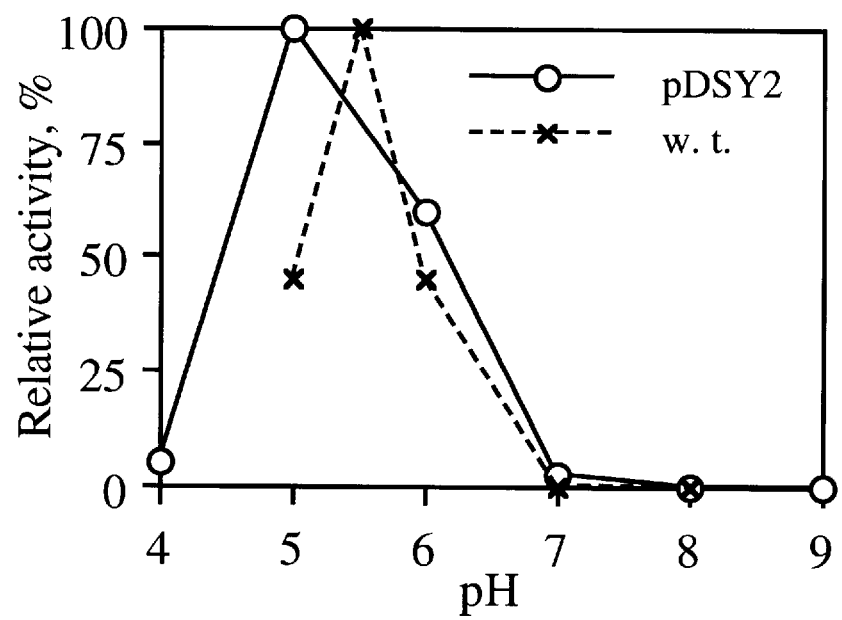
FIGS. 9A and 9B show the pH profile of the laccase produced by pDSY2; (A) syringaldazine oxidation; (B) ABTS oxidation.
Figure 9B:
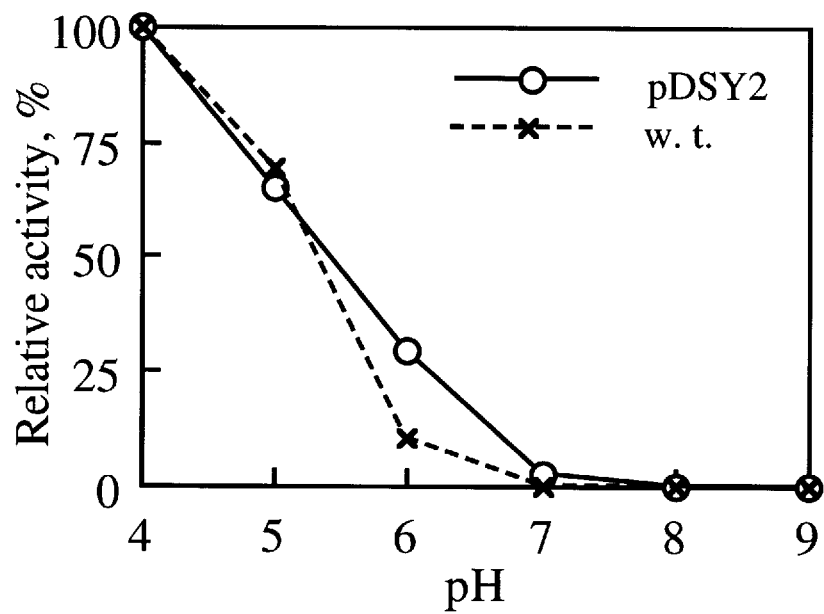

The spectra of the purified laccases have maxima of 615 nm and 275, with the ratio of absorbance at 275 nm to that at 615 nm being 16, indicating one Type I Cu per subunit. The ratio of absorbance at 330 nm to that at 615 nm is 1. 0, close to the 0. 75 value of Rhus vernicefera laccase, suggesting the presence of one Type II and two Type III copper ions per subunit. The extinction coefficient determined by amino acid analysis is 1. 71/(g*cm), 3. Activity The laccase activity is measured by syringaldazine and ABTS oxidations. Expressed per $A_{275}$, the laccase has a value of 83 for LACU. Expressed per mg, it has a LACU of 141. The pH profile of the laccase is provided in FIG. 9.

V. Use of Polyporus Laccase to Dye Hair

The dyeing effect of Polyporus pinsitus laccase is tested and compared to the dyeing effect of 3% $H_2O_2$ on various dye precursors (listed below) and further on 0. 1% p-phenylenediamine compared with a number of modifiers.

Materials:

Dye precursors:

0. 1% p-phenylene-diamine in 0. 1M K-phosphate buffer, pH 7. 0. (pPD)

0. 1% p-toluylene-diamine in 0. 1M K-phosphate buffer, pH 7. 0.

0. 1% chloro-p-phenylenediamine in 0. 1M K-phosphate buffer, pH 7. 0.

0. 1% p-aminophenol in 0. 1M K-phosphate buffer, pH 7. 0.
0. 1% o-aminophenol in 0. 1M K-phosphate buffer, pH 7. 0.
0. 1% 3,4-diaminotoluene in 0. 1M K-phosphate, buffer pH 7. 0.

Modifiers:
0. 1% m-phenylene-diamine in 0. 1M K-phosphate buffer, pH 7. 0.
0. 1% 2,4-diaminoanisole in 0,1M K-phosphate buffer, pH 7. 0.
0. 1% α-naphthol in 0. 1M K-phosphate buffer, pH 7. 0.
0. 1% hydroquinone in 0. 1M K-phosphate buffer, pH 7. 0.
0. 1% pyrocatechol in 0. 1M K-phosphate buffer, pH 7. 0.
0. 1% resorcinol in 0. 1M K-phosphate buffer, pH 7. 0.
0. 1%-4-chlororesorcinol in 0. 1M K-phosphate buffer, pH 7. 0.

When a modifier is used, the dye precursor p-phenylenediamine is combined with one of the above indicated modifiers so that the final concentration in the dyeing solution is 0. 1% with respect to precursor and 0. 1% with respect to modifier. The enzyme used is a recombinant laccase from *Polyporus pinisitus*, at a concentration of 10 LACU/ml.

Other solutions used in the process are 3% $H_2O_2$ (in the final dye solution), and a commercial shampoo.

The quantitative color of the hair tresses is determined on a Datacolor Textflash 2000 (CIE-Lab) by the use of CIE-Lab parameters $L^*$ ("0"=black and "100"=white) combined with $a^*$ ("−"=green and ,"+"=red). $DL^*$ and $Da^*$ are the delta values of $L^*$ and $a^*$, respectively, of a sample when compared to $L^*$ and $a^*$ of untreated hair. The Light fastness is determined under a day light bulb (D65) at 1000 LUX.

Hair tresses of blond European hair (1 gram) are used. 4 ml dye precursor solution (including modifier)is mixed with 1 ml laccase or 1 ml $H_2O_2$ on a Whirley mixer, applied to the hair tresses and kept at 30° C. for 60 minutes. The hair tresses are then rinsed with running water, combed, and air dried.

Figure 10:
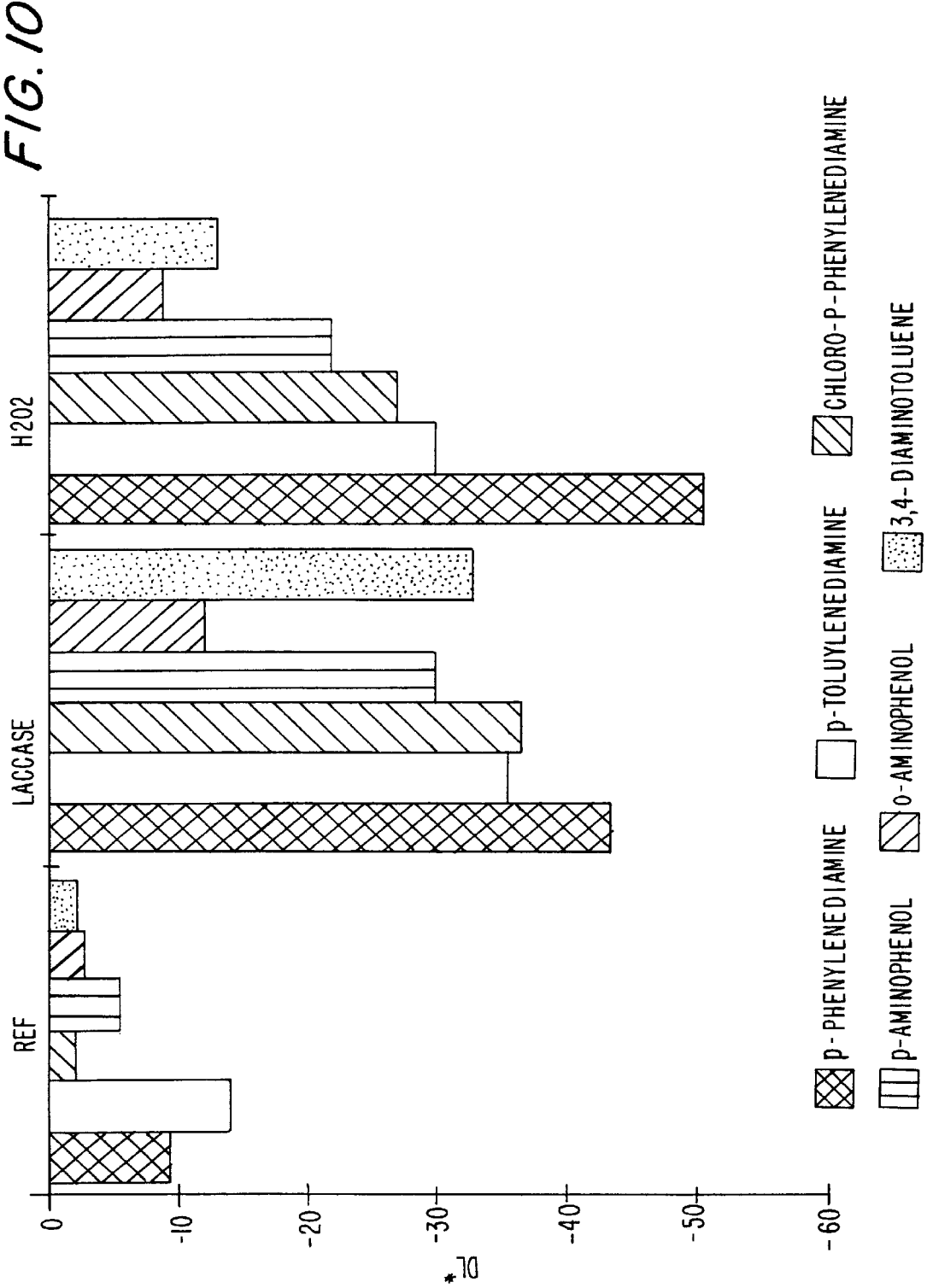
FIG. 10 illustrates a comparison of the use of laccase vs. $H_2O_2$, with various dye precursors, in hair dyeing, as a measurement of DL*.
Figure 11:
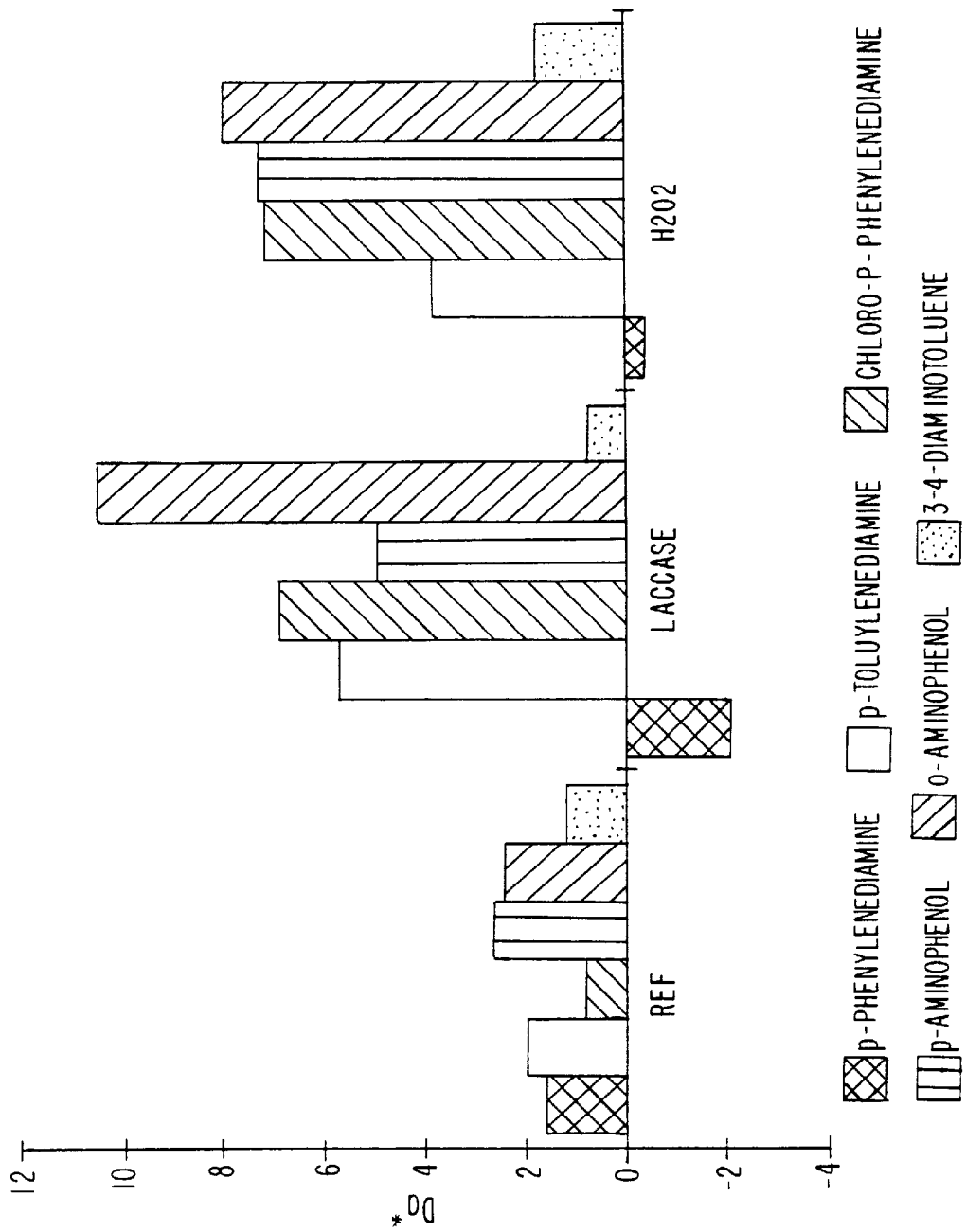
FIG. 11 illustrates a comparison of the use of laccase vs. $H_2O_2$, with various dye precursors, in hair dyeing, as a measurement of Da*.
Figure 12:
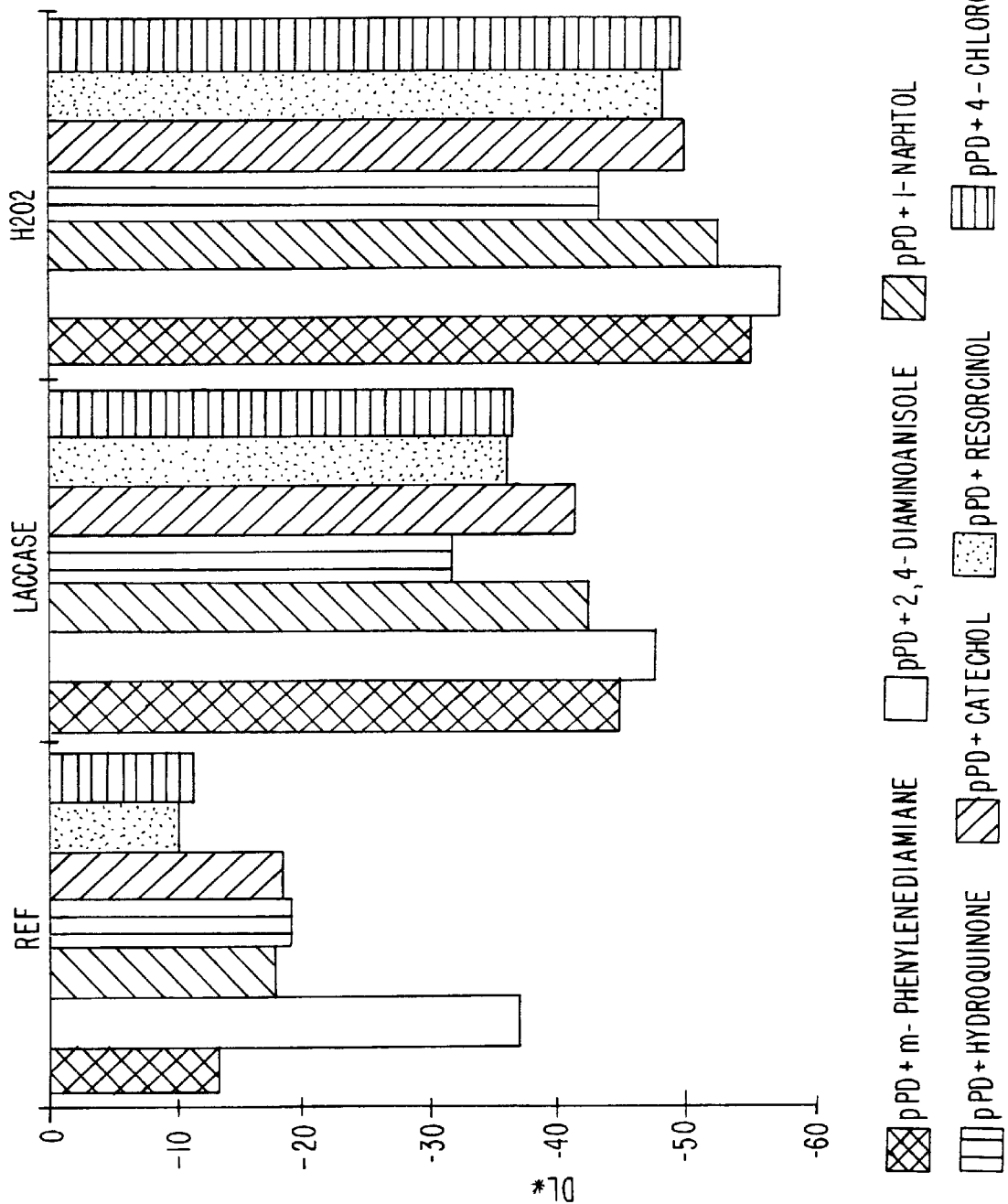
FIG. 12 illustrates a comparison of the use of laccase vs. $H_2O_2$, with various dye precursors and modifiers, in hair dyeing, as a measurement of DL*.

The results of the dyeing effect test are displayed below in Table 5–7 and further in the graphs in FIGS. 10 to 12.

TABLE 5

| Sample no. | Sample ID | $L^*$ | $a^*$ | $DL^*$ | $Da^*$ |
|---|---|---|---|---|---|
|  | Untreated blond hair | 72.25 | 2.42 |  |  |
| 1 | p-phenylenediamine (Reference) | 62.85 | 4.03 | −9.41 | 1,61 |
| 2 | p-phenylenediamine + Laccase | 28.70 | 0.33 | −43.56 | −2,10 |
| 3 | p-phenylenediamine + 3% $H_2O_2$ | 21.88 | 2.04 | −50.37 | −0,39 |
| 4 | p-Toluylenediamine (Reference) | 58.14 | 4.34 | −14.11 | 1.92 |
| 5 | p-Toluylenediamine + Laccase | 36.70 | 8.09 | −35.56 | 5.67 |
| 6 | p-Toluylenediamine + 3% $H_2O_2$ | 42.30 | 6.24 | −29.95 | 3.81 |
| 7 | chloro-p-phenylenediamine (Reference) | 69.82 | 3.23 | −2.43 | 0.81 |
| 8 | chloro-p-phenylenediamine + Laccase | 35.58 | 9.36 | −36.68 | 6.93 |
| 9 | chloro-p-phenylenediamine + 3% $H_2O_2$ | 45.42 | 9.59 | −26.84 | 7.17 |
| 10 | p-aminophenol (Reference) | 66.62 | 5.03 | −5.63 | 2.61 |
| 11 | p-aminophenol + Laccase | 42.42 | 7.38 | −29.84 | 4.95 |
| 12 | p-aminophenol + 3% $H_2O_2$ | 50.54 | 9.42 | −21.72 | 7.26 |
| 13 | o-aminophenol (Reference) | 69.39 | 4.82 | −2.89 | 2.39 |
| 14 | o-aminophenol + Laccase | 60.20 | 12.92 | −12.05 | 10.50 |
| 15 | o-aminophenol + 3% $H_2O_2$ | 63.49 | 10.38 | −8.77 | 7.96 |
| 16 | 3,4-diaminotoluene (Reference) | 69.62 | 3.57 | −2.63 | 1.15 |
| 17 | 3,4-diaminotoluene + Laccase | 39.51 | 3.15 | −32.74 | 0.73 |
| 18 | 3,4-diaminotoluene + 3% $H_2O_2$ | 59.32 | 4.16 | −12.94 | 1.74 |

$L^*$: 0 = black, 100 = white
$a^*$: − = green, + = red

TABLE 6

| Sample no. | Sample ID | $L^*$ | $a^*$ | $DL^*$ | $Da^*$ |
|---|---|---|---|---|---|
|  | Untreated blond hair | 72.25 | 2.42 |  |  |
| 19 | p-phenylenediamine + m-phenylenediamin (Reference) | 58.82 | 0.43 | −13,44 | −1,99 |
| 20 | p-phenylenediamine + m-phenylenediamin + Laccase | 27.20 | 0.83 | −45,05 | −1,59 |
| 21 | p-phenylenediamine + m-phenylenediamine + 3% H2O2 | 16.96 | 0.13 | −55,29 | −2,59 |
| 22 | p-phenylenediamine + 2,4-diaminoanisole (Reference) | 35.37 | −0.02 | −36,89 | −2,45 |
| 23 | p-phenylenediamine + 2,4-diaminoanisole + Laccase | 24.56 | 2.99 | −47,70 | 0,57 |
| 24 | p-phenylenediamine + 2,4-diaminoanisole + 3% H2O2 | 15.06 | 2.21 | −57,20 | −0,21 |
| 25 | p-phenylenediamine + α-naphthol (Reference) | 54.33 | 2.54 | −17,93 | 0,12 |
| 26 | p-phenylenediamine + α-naphthol + Laccase | 29.53 | 4.03 | −42,72 | 1,60 |
| 27 | p-phenylenediamine + α-naphthol + 3% H2O2 | 19.58 | 3.90 | −52,68 | 1,47 |

TABLE 6-continued

| Sample no. | Sample ID | L* | a* | DL* | Da* |
|---|---|---|---|---|---|
| 28 | p-phenylenediamine + hydroquinone (Reference) | 53.25 | 4.08 | −19,01 | 1,65 |
| 29 | p-phenylenediamine + hydroquinone + Laccase | 40.48 | 5.00 | −31,77 | 2,58 |
| 30 | p-phenylenediamine + hydroquinone + 3% H2O2 | 29.06 | 4.96 | −43,20 | 2,53 |

L*: 0 = black, 100 = white
a*: − = green, + = red

TABLE 7

| Sample no. | Sample ID | L* | a* | DL* | Da* |
|---|---|---|---|---|---|
|  | Untreated blond hair | 72.25 | 2.42 |  |  |
| 31 | p-phenylenediamine + pyrocatechol (Reference) | 53.78 | 1.68 | −18.47 | −0.74 |
| 32 | p-phenylenediamine + pyrocatechol + Laccase | 30.77 | 2.64 | −41.49 | 0.22 |
| 33 | p-phenylenediamine + pyrocatechol + 3% $H_2O_2$ | 22.15 | 3.30 | −50.11 | 0.88 |
| 34 | p-phenylenediamine + resorcinol (Reference) | 62.12 | 4.23 | −10.14 | 1.81 |
| 35 | p-phenylenediamine + resorcinol + Laccase | 36.14 | 2.91 | −36.11 | 0.49 |
| 36 | p-phenylenediamine + resorcinol + 3% $H_2O_2$ | 23.94 | 3.16 | −48.31 | 0.74 |
| 40 | p-phenylenediamine + 4-chlororesorcinol (Reference) | 61.18 | 4.70 | −11.07 | 2.28 |
| 41 | p-phenylenediamine + 4-chlororesorcinol + Laccase | 36.00 | 2.76 | −36.26 | 0.34 |
| 42 | p-phenylenediamine + 4-chlororesorcinol + 3% $H_2O_2$ | 22.63 | 2.60 | −49.63 | 0.18 |

L*: 0 = black, 100 = white
a*: − = green, + = red

The above results demonstrate that the *Polyporus pinsitus* laccase can be used for oxidative dyeing of hair.

Tresses of blond european hair (1 gram) are used for testing the wash stability of hair dyed using *Polyporus pinsitus* laccase, compared with hair dyed using $H_2O_2$, and p-phenylene-diamine (pPD) as the dye precursor. Further the wash stability is compared with a commercial oxidative dye. The oxidative hair dyeing is carried out as described above, except that 50 LACU/ml *Polyporus pinsitus* laccase was used.

To test wash stability, the dyed hair tresses are wetted and washed for 15 seconds with 50 µl of commercial shampoo, and rinsed with water for 1 minute. The hair tresses are washed up to 20 times.

Figure 13:
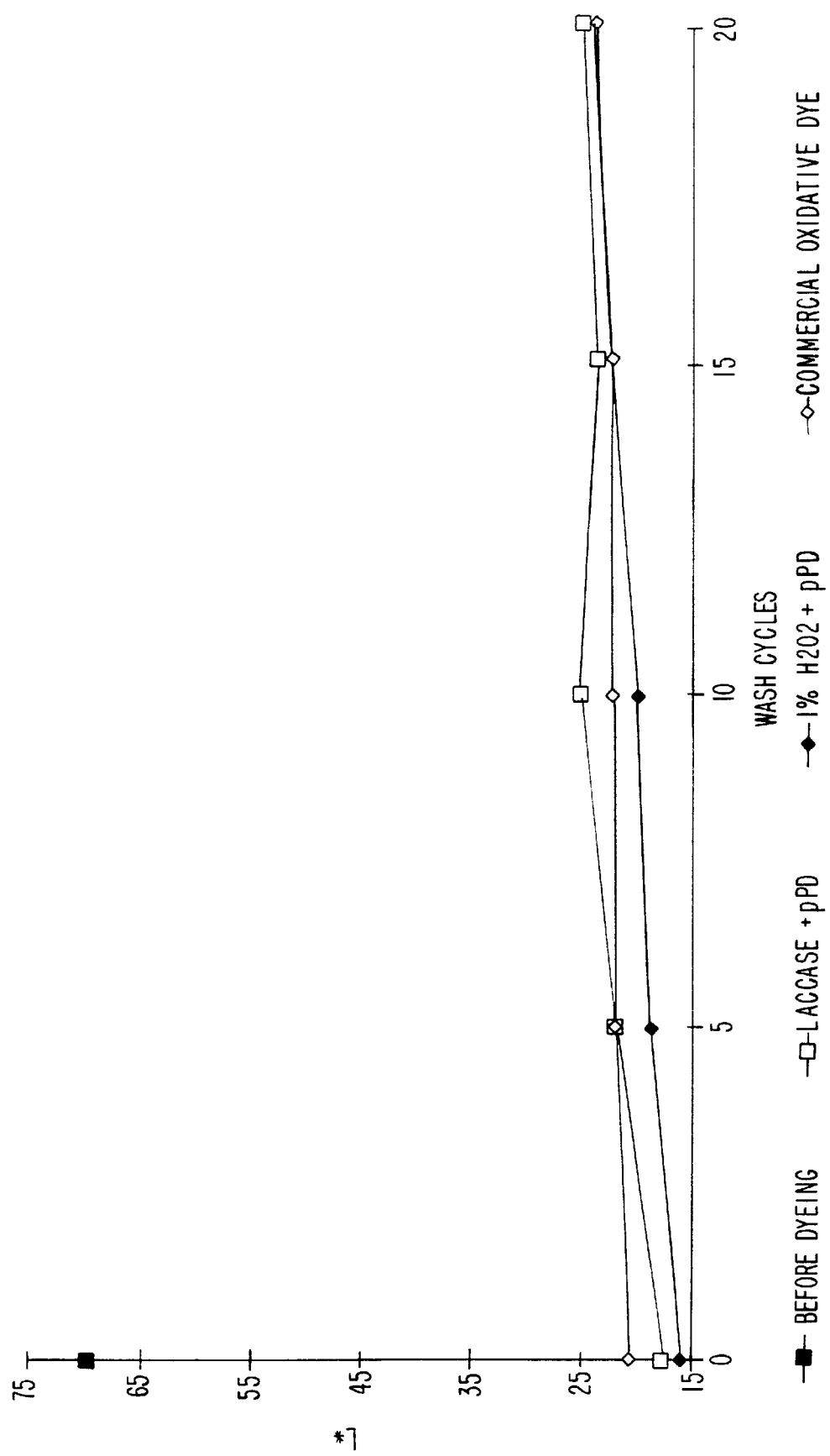
FIG. 13 illustrates a comparison of the wash stability of hair dyed with laccase vs. $H_2O_2$.

The results of the hair wash test are displayed in FIG. 13. It can be seen in FIG. 13 that the wash stability of hair washed up to 20 times is excellent, when using *Polyporus pinsitus* laccase for oxidative dyeing.

To test light fastness, tresses of blond european hair are used for testing the light fastness of hair dyed using *Polyporus pinsitus* laccase in comparison to hair dyed using $H_2O_2$. p-phenylene-diamine is the dye precursor. The dyeing of the hair is carried out as described above. One hair tress is kept dark, while an other is kept at day light (i. e. under a day light bulb (D65)), at approximately 1000 LUX) for up to 275 hours. The CIE-Lab-values are determined immediately after the dyeing of the hair, and further during exposure to day light.

The results of the test are displayed in FIG. 14. FIG. 14 shows that the hair dyed with p-phenylene-diamine using *Polyporus pinsitus* laccase has the same light fastness as hair dyed using $H_2O_2$.

Deposit of Biological Materials

The following biological materials have been deposited under the terms of the Budapest Treaty with the Agricultural Research Service Patent Culture Collection, Northern Regional Research Center, 1815 University Street, Peoria,

| Deposit | Accession Number |
|---|---|
| *E. coli* DH5α containing pDSY22 (41GEN; an ~3.0 kb EcoRI insert) | NRRL B-21263 |
| *E. coli* DH5α containing pDSY23 (41GEN; an ~4.5 kb MluI insert; insert contains a small portion of the EcoRI fragment of pDSY22 and sequences 5' to the EcoRI fragment) | NRRL B-21268 |
| *E. coli* XL-1 Blue containing pDSY21 (31GEN; an ~7.7 kb EcoRI/BamHI insert) | NRRL B-21264 |
| *E. coli* XL-1 Blue containing pDSY18 (21GEN; an ~8.0 kb BamHI insert) | NRRL B-21265 |
| *E. coli* DH5α containing pDSY19 (23GEN; an ~4 kb HindIII insert) | NRRL B-21266 |
| *E. coli* DH5α containing pDSY20 (24GEN; an ~8.5 kb EcoRI insert) | NRRL B-21267 |

What we claim is:

1. A DNA cunstluct oimprising a nucleic acid sequence encoding a Polyponis laccase selected from the group consisting of:
   (a) a nucleic acid scquence which encodes the amino acid sequence of SEQ ID NO:2, SEQ ID NO:4, SEQ ID NO:6, SEQ ID NO:8, or SEQ ID NO: 10; and
   (b) a nucleic acid sequence endogenous to a Poyporus strain, which is capabic of hybridizing to (i) the nucleic acid sequence of SEQ ID NO: 1, SEQ ID NO: 3, SEQ ID NO:5, SEQ ID NO:7, or SEQ ID NO:9, or (ii) aiiy of their complementary strands, at 65° C. in 1. 5×SSPE, 1% SDS, 0. 5% non-fat dried milk, and 200 μg/ml salmon sperm DNA.

2. The DNA construct of claim 1, wherein the nucleic acid sequence encodes the amino acid sequence of SEQ ID NO:2.

3. The DNA construct of claim 2, wherein the nucleic acid sequencc is SEQ ID NOL:1.

4. The DNA construct of claim 1, wherein the nucleic acid sequence is contained in the plasmid pDSY18 contained in *Escherichia coli* NRRL B-21265.

5. The DNA construct of claim 1, wherein the nucleic acid sequence encodes the amino acid sequence of SEQ ID NO:4.

6. The DNA costruct of claim 5, wherein the nucleic acid sequence is SEQ ID NO:3.

7. The DNA construct of claim 1, wherein the nucleic acid sequence is contained in the plasmid pDSY19 cnntained in *Escherichia coli* NRRL B-21266.

8. The DNA construct of claim 1, whcrcin te nucleic acid sequence encodes the amino acid sequence of SEQ ID NO:6.

9. The DNA construct of claim 8, wherein the nucleic acid sequence is SEQ ID NO:5.

10. The DNA construct of claim 1, wherein thc nucleic acid sequence is coneairwd in the plasmid pDSY20 contained in *Eschcrichia coli* NRRL B-21267.

11. The DNA construct of claim 1, wherein the nucleic acid sequence encodes the amino acid sequence of SEQ ID NO:8.

12. The DNA construct of claim 11, wherein the nucleic acid scquence is SEQ ID NO:7.

13. The DNA construct of claim 1, wherein the nucleic acid sequence is contained in the plasmid pDSY21 contained in *Escherichia coli* NRRL B-21264.

14. The DNA construct of claim 1, wherein the nucleic acid sequence encodes the amino acid sequence of SEQ ID NO:10.

15. The DNA construct of claim 14, wherein the nucleic acid sequence is SEQ ID NO:9.

16. The DNA construct of claim 1, wherein the nucleic acid sequence is contained in the plasmid pDSY22 contained in *Escherichia coli* NRRL B-21263 and in the plasmid pDSY23 contained in *Escherichia coli* NRRL B-21268.

17. The DNA construct of claim 1, wherein the nucleic acid sequence is capable of hybridizing to the nuclcic acid sequence of SEQ ID NO:1.

18. The DNA constnict of claim 1, wherein the nucleic acid sequence is capable of hybridizing to the nucleic acid sequence of SEQ ID NO:3.

19. The DNA construct of claim 1, wherein the nucleic acid sequence is capable of hybridizing to the nucleic acid sequence of SEQ ID NO:5.

20. The DNA constnict of claim 1, wherein the nucleic acid sequence is capable of hybridizing to the nucleic acid sequence of SEQ ID NO:7.

21. The DNA construct of claim 1, wherein the nucleic acid sequence is capable of hybridizing to the nucleic acid sequence of SEQ ID NO:9.

22. The DNA construct of claim 1, wherein the nucleic acid sequence encodes a laccase obtained from *Polyporus pinsitus*.

23. A recombinant vector comprising the DNA construct of claim 1.

24. A recombinant host cell comprising the DNA construct of claim 1.

25. The ccll according to claim 24, wherein the host cell is a filamentous fungal cell.

26. The cell accordig to claim 25, wherein the filamentous fungal cell is an Aspergillus cell.

27. The cell according to claim 25, wherein the filamentous fungal cell is a Fusarium cell.

28. A method for producing a laccase comprising (a) cultivating a host cell of claim 24 under conditions conducive to expression of the laccase; and (b) recoveling the polypeptide.

* * * * *